(12) United States Patent
Parham et al.

(10) Patent No.: US 9,831,441 B2
(45) Date of Patent: Nov. 28, 2017

(54) ELECTRONIC DEVICE

(71) Applicant: Merck Patent GmbH, Darmstadt (DE)

(72) Inventors: Amir Hossain Parham, Frankfurt am Main (DE); Irina Martynova, Griesheim (DE); Elvira Montenegro, Weinheim (DE); Teresa Mujica-Fernaud, Darmstadt (DE); Frank Voges, Bad Duerkheim (DE); Arne Buesing, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 265 days.

(21) Appl. No.: 14/439,098

(22) PCT Filed: Oct. 11, 2013

(86) PCT No.: PCT/EP2013/003066
§ 371 (c)(1),
(2) Date: Apr. 28, 2015

(87) PCT Pub. No.: WO2014/067614
PCT Pub. Date: May 8, 2014

(65) Prior Publication Data
US 2015/0280133 A1  Oct. 1, 2015

(30) Foreign Application Priority Data
Oct. 31, 2012 (EP) .................... 12007456

(51) Int. Cl.
| *A61N 5/06* | (2006.01) |
| --- | --- |
| *H01L 51/00* | (2006.01) |
| *C07D 413/14* | (2006.01) |
| *C07D 333/76* | (2006.01) |
| *C07D 403/04* | (2006.01) |
| *C07D 405/04* | (2006.01) |
| *C07D 405/10* | (2006.01) |
| *C07D 491/14* | (2006.01) |
| *C07D 495/14* | (2006.01) |
| *C07D 209/86* | (2006.01) |
| *C07D 307/91* | (2006.01) |
| *C07C 211/54* | (2006.01) |
| *C07C 211/61* | (2006.01) |
| *C07C 225/22* | (2006.01) |
| *C07D 311/82* | (2006.01) |
| *C07D 405/14* | (2006.01) |
| *C07D 471/14* | (2006.01) |
| *C07F 7/08* | (2006.01) |
| *H01L 51/50* | (2006.01) |
| *H01L 51/52* | (2006.01) |

(52) U.S. Cl.
CPC ............ *H01L 51/0061* (2013.01); *A61N 5/06* (2013.01); *C07C 211/54* (2013.01); *C07C 211/61* (2013.01); *C07C 225/22* (2013.01); *C07D 209/86* (2013.01); *C07D 307/91* (2013.01); *C07D 311/82* (2013.01); *C07D 333/76* (2013.01); *C07D 403/04* (2013.01); *C07D 405/04* (2013.01); *C07D 405/10* (2013.01); *C07D 405/14* (2013.01); *C07D 413/14* (2013.01); *C07D 471/14* (2013.01); *C07D 491/14* (2013.01); *C07D 495/14* (2013.01); *C07F 7/0814* (2013.01); *H01L 51/006* (2013.01); *H01L 51/0059* (2013.01); *H01L 51/0072* (2013.01); *H01L 51/0073* (2013.01); *H01L 51/0074* (2013.01); *H01L 51/0094* (2013.01); *A61N 2005/0653* (2013.01); *C07C 2603/08* (2017.05); *C07C 2603/18* (2017.05); *H01L 51/0052* (2013.01); *H01L 51/0056* (2013.01); *H01L 51/0058* (2013.01); *H01L 51/506* (2013.01); *H01L 51/5012* (2013.01); *H01L 51/5016* (2013.01); *H01L 51/5056* (2013.01); *H01L 51/5206* (2013.01); *H01L 51/5221* (2013.01); *Y02E 10/549* (2013.01)

(58) Field of Classification Search
CPC .. C07D 487/00; C07D 209/86; C07D 307/91; C07D 311/82; C07D 333/76; C07D 403/04; H01L 51/0061; H01L 51/0059; A61N 5/06; C07C 211/54; C07C 211/61
See application file for complete search history.

(56) References Cited

U.S. PATENT DOCUMENTS

| 2011/0006670 A1 | 1/2011 | Katakura et al. |
| --- | --- | --- |
| 2011/0114185 A1* | 5/2011 | Kato et al. ............ C07C 211/54 136/263 |
| 2013/0200359 A1 | 8/2013 | Stoessel et al. |

FOREIGN PATENT DOCUMENTS

| CN | 101139317 A | 3/2008 |
| --- | --- | --- |
| DE | 102010048608 A1 | 4/2012 |
| EP | 2085382 A1 | 8/2009 |

OTHER PUBLICATIONS

International Search Report for PCT/EP2013/003066 dated Nov. 26, 2013.

\* cited by examiner

*Primary Examiner* — Nathan M Nutter
(74) *Attorney, Agent, or Firm* — Drinker Biddle & Reath LLP

(57) ABSTRACT

The invention relates to an electronic device containing at least one compound of formula (I) or (II) in an organic layer. The invention further relates to a method for producing the electronic device and the use of a compound of formula (I) or (II) in an electronic device.

15 Claims, No Drawings

ELECTRONIC DEVICE

CROSS-REFERENCE TO RELATED APPLICATIONS

This application is a national stage application (under 35 U.S.C. §371) of PCT/EP2013/003066, filed Oct. 11, 2013, which claims benefit of European Application No. 12007456.2, filed Oct. 31, 2012, both of which are incorporated herein by reference in their entirety.

The present application relates to an electronic device which comprises at least one compound of the formula (I) or (II) in an organic layer.

Electronic devices in the sense of this application are taken to mean, in particular, so-called organic electronic devices which comprise organic semiconductor materials as functional materials. Again in particular, they are taken to mean organic electroluminescent devices (OLEDs) and other electronic devices which are mentioned below.

The structure of OLEDs in which organic semiconductors are employed as functional materials is described, for example, in U.S. Pat. No. 4,539,507, U.S. Pat. No. 5,151,629, EP 0676461 and WO 98/27136. In general, the term OLED is taken to mean electronic devices which comprise organic material and emit light on application of an electrical voltage.

In the case of electronic devices, in particular OLEDs, there is considerable interest in improving the performance data, in particular lifetime and efficiency. An important role is played here by layers having a hole-transporting function in the electronic device, such as, for example, hole-injection layers, hole-transport layers, electron-blocking layers and emitting layers.

Novel materials having hole-transporting properties are continuously being sought for this purpose. They can be employed in the said layers as pure materials, as principal components or as secondary components in combination with further materials. In hole-injecting layers, hole-transport layers and electron-blocking layers, the materials having hole-transporting properties are typically employed as pure substances. However, they can also be employed in such layers as a mixture with a doped further material. In emitting layers, in particular in phosphorescent emitting layers, the materials having hole-transporting properties are preferably employed as the principal component of the layer in combination with further materials, for example emitter materials. In this case, they are called host materials of the emitting layer.

It is known from the prior art to employ triarylamines as materials having hole-transporting properties in the above-mentioned layers. These can be monotriarylamines, as described, for example, in JP 1995/053955, WO 2006/123667 and JP 2010/222268, or bis- or polyamines, as described, for example, in U.S. Pat. No. 7,504,163 or US 2005/0184657. Known examples of such triarylamine compounds are, inter alia, tris-p-biphenylamine, N,N'-di-1-naphthyl-N,N'-diphenyl-1,1'-biphenyl-4,4'-diamine (NPB) and 4,4',4''-tris-(3-methylphenylphenylamino)triphenylamine (MTDATA).

Also known is the use of triarylamine compounds having a relatively complex, asymmetrical structure as hole-transporting compounds in OLEDs (WO 2011/021520). These compounds contain a triarylamino group which is bonded to a dibenzofuran or similar aryl group. In all cases here, only a single triarylamino group is present in the compound.

The prior art furthermore discloses compounds in which two carbazole groups are bonded opposite one another to a dibenzofuran group, for example in WO 2011/004639. However, such compounds are less suitable as hole-transport materials, owing to the position of their HOMO.

In spite of these advances, there therefore continues to be a need for compounds having hole-transporting properties for use in electronic devices. In particular, there is a need for compounds which have excellent hole mobility and a suitable triplet level in order to be used in phosphorescent OLEDs. Furthermore, the compounds should have a high glass transition temperature, Compounds having the above-mentioned properties enable OLEDs to be obtained which have good performance data, in particular high efficiency and a long lifetime.

Surprisingly, it has now been found that compounds in which two triarylamino groups or one triarylamino group and one carbazole group are bonded "face-to-face", i.e. opposite one another, to a dibenzofuran or similar aryl group have excellent hole-transporting properties. Furthermore, they have excellent hole mobility and a suitable triplet level in order to be used in phosphorescent OLEDs. Again furthermore, they have a high glass transition temperature, which makes them particularly suitable for use in thin amorphous organic layers in OLEDs.

Individual compounds having a structure of this type are known in the prior art (G.-Q. Li et al., Tetrahedron, 2011, 67, 6804-6811), but the technical teaching therein is restricted to the synthesis of the compounds. There is no stimulus therein to employ the compounds as functional materials in electronic devices.

The invention thus relates to an electronic device, comprising anode, cathode and at least one organic layer, which comprises at least one compound of the formula (I) or (II)

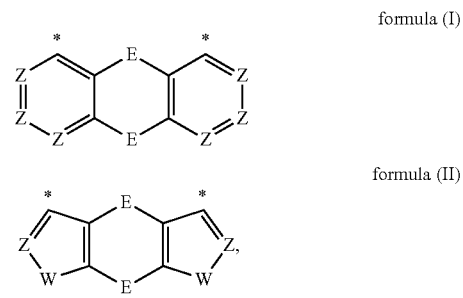

formula (I)

formula (II)

where a group selected from the groups of the formulae

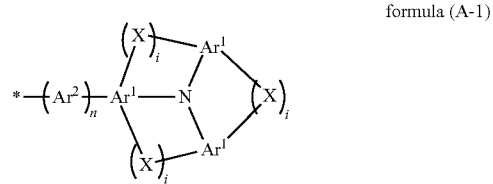

formula (A-1)

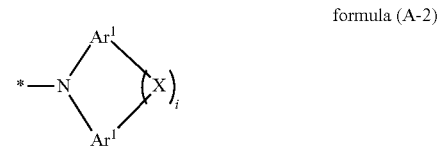

formula (A-2)

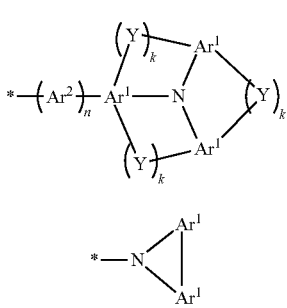

formula (C-1)

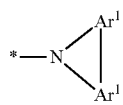

formula (C-2)

is bonded at the positions denoted by *,
where:
E is selected on each occurrence, identically or differently, from a single bond, $C(R^1)_2$, $Si(R^1)_2$, C=O, O, S, S=O, $SO_2$ and $NR^1$;
Z is on each occurrence, identically or differently, $CR^1$ or N;
W is selected on each occurrence, identically or differently, from C=O, O, S, S=O, $SO_2$ and $NR^1$;
$Ar^1$ is selected on each occurrence, identically or differently, from aryl or heteroaryl groups having 6 to 13 aromatic ring atoms, which may be substituted by one or more radicals $R^1$;
$Ar^2$ is selected on each occurrence, identically or differently, from aryl or heteroaryl groups having 6 to 13 aromatic ring atoms, which may be substituted by one or more radicals $R^1$;
X is selected on each occurrence, identically or differently, from $C(R^1)_2$, $Si(R^1)_2$, C=O, O, S, S=O, $SO_2$ and $NR^1$;
Y is a single bond;
$R^1$ is on each occurrence, identically or differently, H, D, F, $C(=O)R^2$, CN, $Si(R^2)_3$, $N(R^2)_2$, $P(=O)(R^2)_2$, $S(=O)R^2$, $S(=O)_2R^2$, a straight-chain alkyl or alkoxy group having 1 to 20 C atoms or a branched or cyclic alkyl, or alkoxy group having 3 to 20 C atoms or an alkenyl or alkynyl group having 2 to 20 C atoms, where the above-mentioned groups may each be substituted by one or more radicals $R^2$ and where one or more $CH_2$ groups in the above-mentioned groups may be replaced by —$R^2C=CR^2$—, —C≡C—, $Si(R^2)_2$, C=O, C=S, C=$NR^2$, —C(=O)O—, —C(=O)$NR^2$—, $NR^2$, $P(=O)(R^2)$, —O—, —S—, SO or $SO_2$ and where one or more H atoms in the above-mentioned groups may be replaced by D, F or CN, or an aromatic or heteroaromatic ring system having 5 to 30 aromatic ring atoms, which may be substituted by one or more radicals $R^2$, or an aryloxy or heteroaryloxy group having 5 to 30 aromatic ring atoms, which may be substituted by one or more radicals $R^2$, where two or more radicals $R^1$ may be linked to one another and may form a ring;
$R^2$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^2$ here may be linked to one another and may form a ring;
n is on each occurrence, identically or differently, 0, 1, 2, 3 or 4;
i is on each occurrence, identically or differently, 0 or 1;
k is on each occurrence, identically or differently, 0 or 1, where at least one index k per group of the formula (C-1) must be equal to 1;

and where a group selected from groups of the formulae (A-1) and (A-2) must be bonded at at least one of the positions denoted by *,
and where furthermore no condensed aryl or heteroaryl group having 14 or more aromatic ring atoms is present in the compound.

A condensed aryl group here is taken to mean an aryl group which contains two or more aromatic rings which are condensed with one another, i.e. share one or more aromatic bonds with one another. A corresponding definition applies to heteroaryl groups. Examples of condensed aryl groups, irrespective of the number of their ring atoms, are naphthyl, anthracenyl, pyrenyl, phenanthrenyl and perylenyl. Examples of condensed heteroaryl groups are quinolinyl, indolyl, carbazolyl, and acridinyl.

General definitions of chemical groups in the context of the present application follow:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cyclo-heptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alis, that the two radicals are linked to one another by a chemical bond. Furthermore, however, the above-mentioned formulation is also intended to be taken to mean that, in the case where one of the two radicals represents hydrogen, the second radical is bonded at the position to which the hydrogen atom was bonded, with formation of a ring.

The group E is preferably selected on each occurrence, identically or differently, from a single bond, C(R$^1$)$_2$, C=O, O, S and NR$^1$. It is particularly preferably selected from a single bond, O and S.

It is preferred for not more than two adjacent groups Z to be equal to N. Furthermore preferably, not more than two groups Z in an aromatic ring are equal to N. Z is generally particularly preferably equal to CR$^1$.

The group W is preferably selected on each occurrence, identically or differently, from O, S and NR$^1$. It is preferably selected from O and S.

The group Ar$^1$ is preferably selected, identically or differently, from aryl or heteroaryl groups having 6 to 10 aromatic ring atoms, which may be substituted by one or more radicals R$^1$. Ar$^1$ is particularly preferably selected from phenyl, naphthyl, pyridyl, pyrimidyl, pyridazyl, pyrazinyl and triazinyl, each of which may be substituted by one or more radicals R$^1$.

The group Ar$^2$ is preferably selected, identically or differently, from aryl or heteroaryl groups having 6 to 10 aromatic ring atoms, which may be substituted by one or more radicals R$^1$. Ar$^2$ is particularly preferably selected from phenyl, naphthyl, pyridyl, pyrimidyl, pyridazyl, pyrazinyl and triazinyl, each of which may be substituted by one or more radicals R$^1$.

The group X is preferably selected on each occurrence, identically or differently, from C(R$^1$)$_2$, C=O, O, S and NR$^1$.

R$^1$ is preferably on each occurrence, identically or differently, H, D, F, CN, Si(R$^2$)$_3$, N(R$^2$)$_2$, a straight-chain alkyl or alkoxy group having 1 to 20 C atoms or a branched or cyclic alkyl or alkoxy group having 3 to 20 C atoms, where the above-mentioned groups may each be substituted by one or more radicals R$^2$ and where one or more CH$_2$ groups in the above-mentioned groups may be replaced by —C≡C—, —R$^2$C=CR$^2$—, Si(R$^2$)$_2$, C=O, C=NR$^2$, —NR$^2$—, —O—, —S—, —C(=O)O— or —C(=O)NR²—, or an aromatic or heteroaromatic ring system having 5 to 20 aromatic ring atoms, which may be substituted by one or more radicals R², where two or more radicals R¹ may be linked to one another and may form a ring.

The index n is preferably on each occurrence, identically or differently, 0 or 1, particularly preferably 0.

The index I is preferably equal to 0.

For compounds of the formulae (I) and (II), it is furthermore preferred for a group selected from groups of the formula (A-1) and (A-2) to be bonded at the positions denoted by *.

It is furthermore preferred for compounds of the formulae (I) and (II) to contain no condensed aryl groups having more than 10 aromatic ring atoms.

It is furthermore preferred for compounds of the formulae (I) and (II) to contain no further arylamino groups in addition to the groups (A-1), (A-2), (C-1) and (C-2). They particularly preferably contain no further amino groups.

It is furthermore preferred for compounds of the formulae (I) and (II) to contain no further carbazole groups in addition to the groups (A-1), (A-2), (C-1) and (C-2).

It is furthermore preferred for compounds of the formulae (I) and (II) to contain no electron-deficient heteroaryl groups. For the purposes of the present invention, electron-deficient heteroaryl groups are taken to mean, in particular, heteroaromatic six-membered rings having one or more nitrogen atoms and heteroaromatic five-membered rings having two or more heteroatoms, in particular heteroatoms selected from N, O and S.

Compounds of the formula (I) are preferably compounds of the following formulae (I-1) to (I-4):

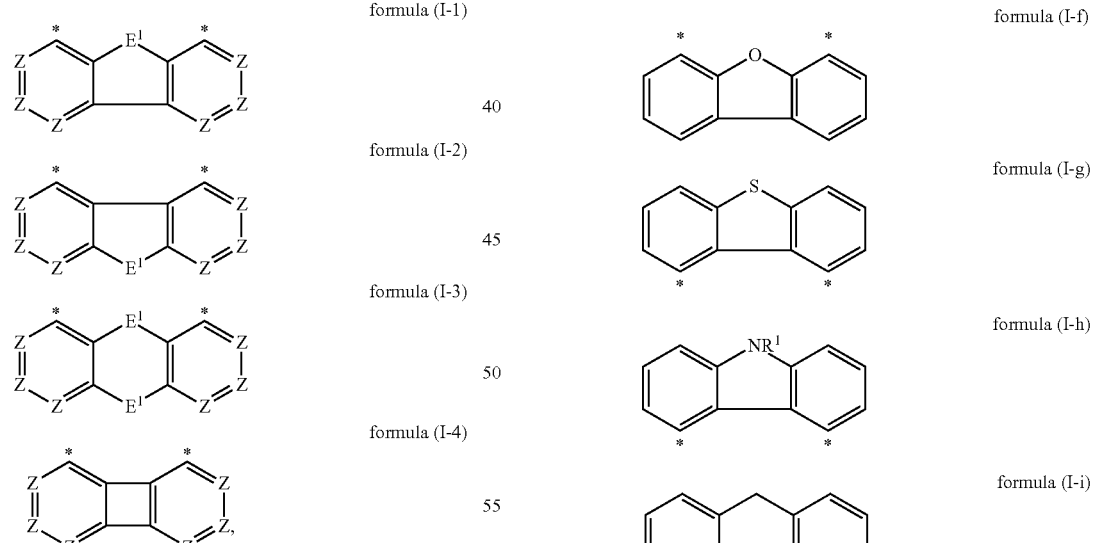

where $E^1$ is selected from $C(R^1)_2$, $Si(R^1)_2$, C=O, O, S, S=O, SO₂ and $NR^1$, where a group selected from the groups of the formulae (A-1), (A-2), (C-1) and (C-2) is bonded at the positions denoted by * and where a group selected from groups of the formulae (A-1) and (A-2) is bonded at at least one of the positions denoted by *, and where all other groups are defined as above.

The preferred embodiments of groups indicated in the application are likewise regarded as preferred.

$E^1$ is preferably selected from $C(R^1)_2$, C=O, O, S and $NR^1$.

Compounds of the formula (I) are particularly preferably compounds of the following formulae (I-a) to (I-w)

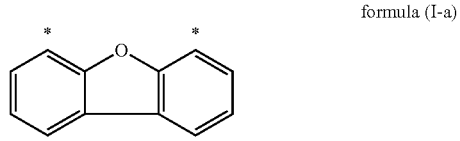
formula (I-a)

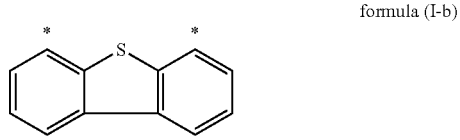
formula (I-b)

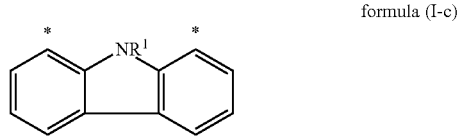
formula (I-c)

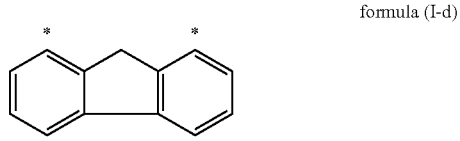
formula (I-d)

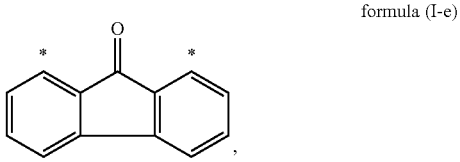
formula (I-e)

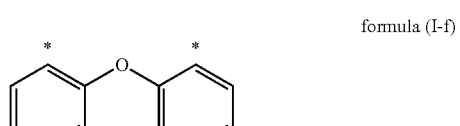
formula (I-f)

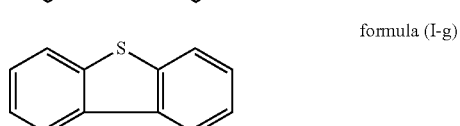
formula (I-g)

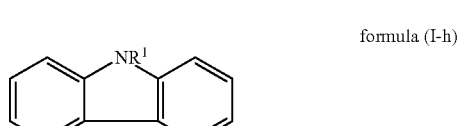
formula (I-h)

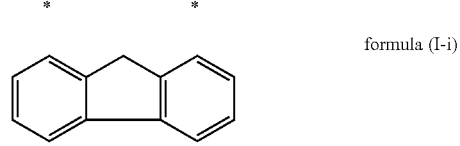
formula (I-i)

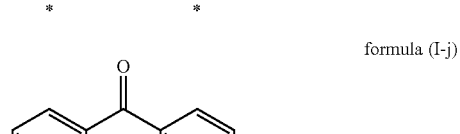
formula (I-j)

formula (I-k)
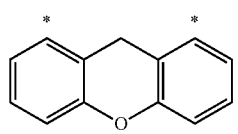

formula (I-l)
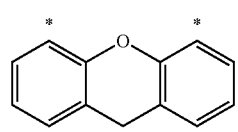

formula (I-m)
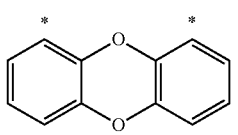

formula (I-n)
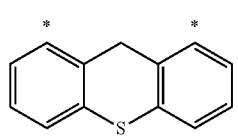

formula (I-o)
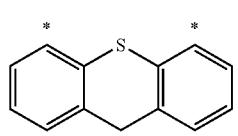

formula (I-p)
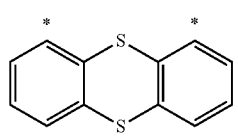

formula (I-q)
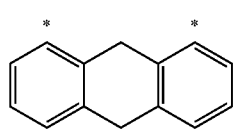

formula (I-r)
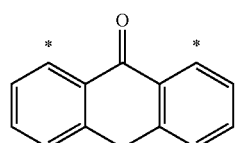

formula (I-s)
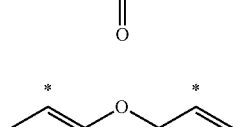

formula (I-t)
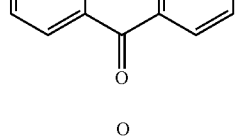

formula (I-u)
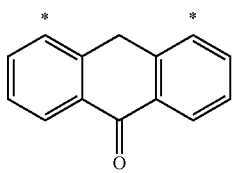

formula (I-v)
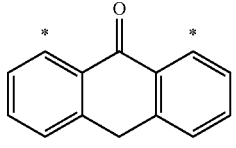

formula (I-w)
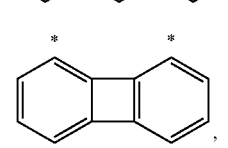

where the compounds may be substituted at all free positions by radicals $R^1$, and where a group selected from the groups of the formulae (A-1), (A-2), (C-1) and (C-2) is bonded at the positions denoted by * and where a group selected from groups of the formulae (A-1) and (A-2) is bonded at at least one of the positions denoted by *.

The preferred embodiments of groups indicated in the application are likewise preferred.

Particular preference is given to compounds of the formula (I-a) and (I-b).

Compounds of the formula (II) are preferably compounds of the formulae (II-1) to (II-3)

formula (II-1)
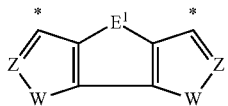

formula (II-2)
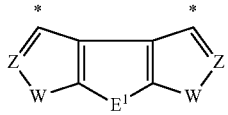

formula (II-3)
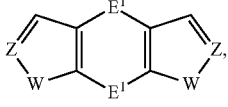

where $E^1$ is selected from $C(R^1)_2$, $Si(R^1)_2$, C=O, O, S, S=O, $SO_2$ and $NR^1$, where a group selected from the groups of the formulae (A-1), (A-2), (C-1) and (C-2) is bonded at the positions denoted by * and where a group selected from groups of the formulae (A-1) and (A-2) is bonded at at least one of the positions denoted by *, and where all other groups are defined as above.

The preferred embodiments of groups indicated in the application are likewise regarded as preferred.

$E^1$ is preferably selected from $C(R^1)_2$, C=O, O, S and $NR^1$.

Compounds of the formula (II) are particularly preferably compounds of the following formulae (II-a) and (II-b)

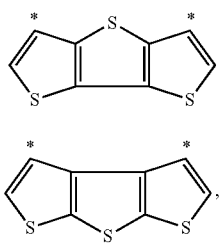

formula (II-a)

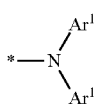

formula (II-b)

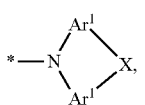

where the compounds may be substituted at all free positions by radicals $R^1$, where a group selected from the groups of the formulae (A-1), (A-2), (C-1) and (C-2) is bonded at the positions denoted by * and where a group selected from groups of the formulae (A-1) and (A-2) is bonded at at least one of the positions denoted by *.

The preferred embodiments of groups indicated in the application are likewise preferred.

The preferred embodiments of groups indicated in the application are likewise preferred.

A group of the formula (A-1) preferably corresponds to a group of the following formulae (A-1-1) to (A-1-6)

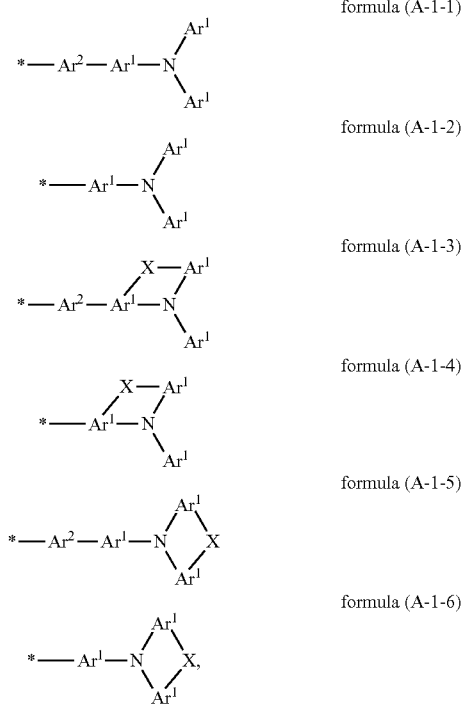

where the symbols occurring are defined as above. The preferred embodiments of groups indicated in the application are likewise regarded as preferred.

In particular, $Ar^1$ and $Ar^2$ in the formulae (A-1-1) to (A-1-6) are preferably selected, identically or differently, from phenyl, naphthyl, pyridyl, pyrimidyl, pyridazyl, pyrazinyl and triazinyl, each of which may be substituted by one or more radicals $R^1$. Furthermore, the group X is preferably selected on each occurrence, identically or differently, from $C(R^1)_2$, C=O, O, S and $NR^1$.

Particular preference is given to the formulae (A-1-1) and (A-1-2).

A group of the formula (A-2) preferably corresponds to a group of the following formulae (A-2-1) to (A-2-2)

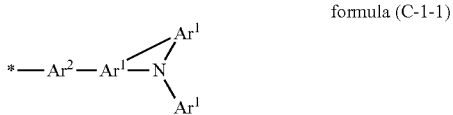

formula (A-2-1)

formula (A-2-2)

where the symbols occurring are defined as above. The preferred embodiments of groups indicated in the application are likewise regarded as preferred.

In particular, $Ar^1$ in the formulae (A-2-1) to (A-2-2) is preferably selected, identically or differently, from phenyl, naphthyl, pyridyl, pyrimidyl, pyridazyl, pyrazinyl and triazinyl, each of which may be substituted by one or more radicals $R^1$. Furthermore, the group X is preferably selected on each occurrence, identically or differently, from $C(R^1)_2$, C=O, O, S and $NR^1$.

Particular preference is given to the formula (A-2-1).

A group of the formula (C-1) preferably corresponds to a group of the following formulae (C-1-1) to (C-1-4)

formula (C-1-1)

formula (C-1-2)

formula (C-1-3)

formula (C-1-4)

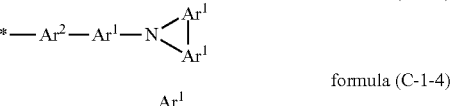

where the symbols occurring are defined as above. The preferred embodiments of groups indicated in the application are likewise regarded as preferred.

In particular, $Ar^1$ and $Ar^2$ in the formulae (C-1-1) to (C-1-4) are preferably selected, identically or differently, from phenyl, naphthyl, pyridyl, pyrimidyl, pyridazyl, pyrazinyl and triazinyl, each of which may be substituted by one or more radicals $R^1$.

A group of the formula (C-2) preferably corresponds to a group of the following formula (C-2-1)

formula (C-2-1)

where $Ar^1$ is selected, identically or differently, from phenyl, naphthyl, pyridyl, pyrimidyl, pyridazyl, pyrazinyl and triazinyl, each of which may be substituted by one or more radicals $R^1$.

The following structures are preferred in accordance with the present application (scheme below in combination with table):

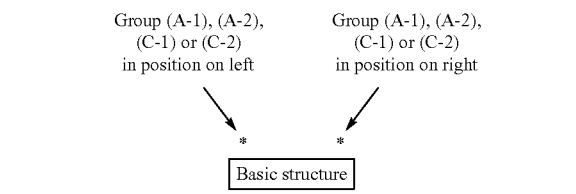

| Structure | Basic structure of the formula | Group in position * on left | Group in position * on right |
|---|---|---|---|
| (I-a-1) | (I-a) | (A-1) | (A-1) |
| (I-a-2) | " | (A-1) | (A-2) |
| (I-a-3) | " | (A-1) | (C-1) |
| (I-a-4) | " | (A-1) | (C-2) |
| (I-a-5) | " | (A-2) | (A-2) |
| (I-a-6) | " | (A-2) | (C-1) |
| (I-a-7) | " | (A-2) | (C-2) |
| (I-b-1) | (I-b) | (A-1) | (A-1) |
| (I-b-2) | " | (A-1) | (A-2) |
| (I-b-3) | " | (A-1) | (C-1) |
| (I-b-4) | " | (A-1) | (C-2) |
| (I-b-5) | " | (A-2) | (A-2) |
| (I-b-6) | " | (A-2) | (C-1) |
| (I-b-7) | " | (A-2) | (C-2) |
| (I-c-1) | (I-c) | (A-1) | (A-1) |
| (I-c-2) | " | (A-1) | (A-2) |
| (I-c-3) | " | (A-1) | (C-1) |
| (I-c-4) | " | (A-1) | (C-2) |
| (I-c-5) | " | (A-2) | (A-2) |
| (I-c-6) | " | (A-2) | (C-1) |
| (I-c-7) | " | (A-2) | (C-2) |
| (I-d-1) | (I-d) | (A-1) | (A-1) |
| (I-d-2) | " | (A-1) | (A-2) |
| (I-d-3) | " | (A-1) | (C-1) |
| (I-d-4) | " | (A-1) | (C-2) |
| (I-d-5) | " | (A-2) | (A-2) |
| (I-d-6) | " | (A-2) | (C-1) |
| (I-d-7) | " | (A-2) | (C-2) |
| (I-e-1) | (I-e) | (A-1) | (A-1) |
| (I-e-2) | " | (A-1) | (A-2) |
| (I-e-3) | " | (A-1) | (C-1) |
| (I-e-4) | " | (A-1) | (C-2) |
| (I-e-5) | " | (A-2) | (A-2) |
| (I-e-6) | " | (A-2) | (C-1) |
| (I-e-7) | " | (A-2) | (C-2) |
| (I-f-1) | (I-f) | (A-1) | (A-1) |
| (I-f-2) | " | (A-1) | (A-2) |
| (I-f-3) | " | (A-1) | (C-1) |
| (I-f-4) | " | (A-1) | (C-2) |
| (I-f-5) | " | (A-2) | (A-2) |
| (I-f-6) | " | (A-2) | (C-1) |
| (I-f-7) | " | (A-2) | (C-2) |
| (I-g-1) | (I-g) | (A-1) | (A-1) |
| (I-g-2) | " | (A-1) | (A-2) |
| (I-g-3) | " | (A-1) | (C-1) |
| (I-g-4) | " | (A-1) | (C-2) |
| (I-g-5) | " | (A-2) | (A-2) |
| (I-g-6) | " | (A-2) | (C-1) |
| (I-g-7) | " | (A-2) | (C-2) |
| (I-h-1) | (I-h) | (A-1) | (A-1) |
| (I-h-2) | " | (A-1) | (A-2) |
| (I-h-3) | " | (A-1) | (C-1) |
| (I-h-4) | " | (A-1) | (C-2) |
| (I-h-5) | " | (A-2) | (A-2) |
| (I-h-6) | " | (A-2) | (C-1) |
| (I-h-7) | " | (A-2) | (C-2) |
| (I-i-1) | (I-i) | (A-1) | (A-1) |
| (I-i-2) | " | (A-1) | (A-2) |
| (I-i-3) | " | (A-1) | (C-1) |
| (I-i-4) | " | (A-1) | (C-2) |
| (I-i-5) | " | (A-2) | (A-2) |
| (I-i-6) | " | (A-2) | (C-1) |
| (I-i-7) | " | (A-2) | (C-2) |
| (I-j-1) | (I-j) | (A-1) | (A-1) |
| (I-j-2) | " | (A-1) | (A-2) |
| (I-j-3) | " | (A-1) | (C-1) |
| (I-j-4) | " | (A-1) | (C-2) |
| (I-j-5) | " | (A-2) | (A-2) |
| (I-j-6) | " | (A-2) | (C-1) |
| (I-j-7) | " | (A-2) | (C-2) |
| (I-k-1) | (I-k) | (A-1) | (A-1) |
| (I-k-2) | " | (A-1) | (A-2) |
| (I-k-3) | " | (A-1) | (C-1) |
| (I-k-4) | " | (A-1) | (C-2) |
| (I-k-5) | " | (A-2) | (A-2) |
| (I-k-6) | " | (A-2) | (C-1) |
| (I-k-7) | " | (A-2) | (C-2) |
| (I-l-1) | (I-l) | (A-1) | (A-1) |
| (I-l-2) | " | (A-1) | (A-2) |
| (I-l-3) | " | (A-1) | (C-1) |
| (I-l-4) | " | (A-1) | (C-2) |
| (I-l-5) | " | (A-2) | (A-2) |
| (I-l-6) | " | (A-2) | (C-1) |
| (I-l-7) | " | (A-2) | (C-2) |
| (I-m-1) | (I-m) | (A-1) | (A-1) |
| (I-m-2) | " | (A-1) | (A-2) |
| (I-m-3) | " | (A-1) | (C-1) |
| (I-m-4) | " | (A-1) | (C-2) |
| (I-m-5) | " | (A-2) | (A-2) |
| (I-m-6) | " | (A-2) | (C-1) |
| (I-m-7) | " | (A-2) | (C-2) |
| (I-n-1) | (I-n) | (A-1) | (A-1) |
| (I-n-2) | " | (A-1) | (A-2) |
| (I-n-3) | " | (A-1) | (C-1) |
| (I-n-4) | " | (A-1) | (C-2) |
| (I-n-5) | " | (A-2) | (A-2) |
| (I-n-6) | " | (A-2) | (C-1) |
| (I-n-7) | " | (A-2) | (C-2) |
| (I-o-1) | (I-o) | (A-1) | (A-1) |
| (I-o-2) | " | (A-1) | (A-2) |
| (I-o-3) | " | (A-1) | (C-1) |
| (I-o-4) | " | (A-1) | (C-2) |
| (I-o-5) | " | (A-2) | (A-2) |
| (I-o-6) | " | (A-2) | (C-1) |
| (I-o-7) | " | (A-2) | (C-2) |
| (I-p-1) | (I-p) | (A-1) | (A-1) |
| (I-p-2) | " | (A-1) | (A-2) |
| (I-p-3) | " | (A-1) | (C-1) |
| (I-p-4) | " | (A-1) | (C-2) |
| (I-p-5) | " | (A-2) | (A-2) |
| (I-p-6) | " | (A-2) | (C-1) |
| (I-p-7) | " | (A-2) | (C-2) |
| (I-q-1) | (I-q) | (A-1) | (A-1) |
| (I-q-2) | " | (A-1) | (A-2) |
| (I-q-3) | " | (A-1) | (C-1) |
| (I-q-4) | " | (A-1) | (C-2) |
| (I-q-5) | " | (A-2) | (A-2) |
| (I-q-6) | " | (A-2) | (C-1) |
| (I-q-7) | " | (A-2) | (C-2) |
| (I-r-1) | (I-r) | (A-1) | (A-1) |
| (I-r-2) | " | (A-1) | (A-2) |
| (I-r-3) | " | (A-1) | (C-1) |
| (I-r-4) | " | (A-1) | (C-2) |
| (I-r-5) | " | (A-2) | (A-2) |
| (I-r-6) | " | (A-2) | (C-1) |
| (I-r-7) | " | (A-2) | (C-2) |
| (I-s-1) | (I-s) | (A-1) | (A-1) |
| (I-s-2) | " | (A-1) | (A-2) |
| (I-s-3) | " | (A-1) | (C-1) |
| (I-s-4) | " | (A-1) | (C-2) |
| (I-s-5) | " | (A-2) | (A-2) |
| (I-s-6) | " | (A-2) | (C-1) |
| (I-s-7) | " | (A-2) | (C-2) |
| (I-t-1) | (I-t) | (A-1) | (A-1) |
| (I-t-2) | " | (A-1) | (A-2) |
| (I-t-3) | " | (A-1) | (C-1) |

| Structure | Basic structure of the formula | Group in position * on left | Group in position * on right |
|---|---|---|---|
| (I-t-4) | " | (A-1) | (C-2) |
| (I-t-5) | " | (A-2) | (A-2) |
| (I-t-6) | " | (A-2) | (C-1) |
| (I-t-7) | " | (A-2) | (C-2) |
| (I-u-1) | (I-u) | (A-1) | (A-1) |
| (I-u-2) | " | (A-1) | (A-2) |
| (I-u-3) | " | (A-1) | (C-1) |
| (I-u-4) | " | (A-1) | (C-2) |
| (I-u-5) | " | (A-2) | (A-2) |
| (I-u-6) | " | (A-2) | (C-1) |
| (I-u-7) | " | (A-2) | (C-2) |
| (I-v-1) | (I-v) | (A-1) | (A-1) |
| (I-v-2) | " | (A-1) | (A-2) |
| (I-v-3) | " | (A-1) | (C-1) |
| (I-v-4) | " | (A-1) | (C-2) |
| (I-v-5) | " | (A-2) | (A-2) |
| (I-v-6) | " | (A-2) | (C-1) |
| (I-v-7) | " | (A-2) | (C-2) |
| (I-w-1) | (I-w) | (A-1) | (A-1) |
| (I-w-2) | " | (A-1) | (A-2) |
| (I-w-3) | " | (A-1) | (C-1) |
| (I-w-4) | " | (A-1) | (C-2) |
| (I-w-5) | " | (A-2) | (A-2) |
| (I-w-6) | " | (A-2) | (C-1) |
| (I-w-7) | " | (A-2) | (C-2) |
| (II-a-1) | (II-a) | (A-1) | (A-1) |
| (II-a-2) | " | (A-1) | (A-2) |
| (II-a-3) | " | (A-1) | (C-1) |
| (II-a-4) | " | (A-1) | (C-2) |
| (II-a-5) | " | (A-2) | (A-2) |
| (II-a-6) | " | (A-2) | (C-1) |
| (II-a-7) | " | (A-2) | (C-2) |
| (II-b-1) | (II-b) | (A-1) | (A-1) |
| (II-b-2) | " | (A-1) | (A-2) |
| (II-b-3) | " | (A-1) | (C-1) |
| (II-b-4) | " | (A-1) | (C-2) |
| (II-b-5) | " | (A-2) | (A-2) |
| (II-b-6) | " | (A-2) | (C-1) |
| (II-b-7) | " | (A-2) | (C-2) |

The preferred embodiments indicated in the application, in particular the preferred embodiments of the groups (A-1), (A-2), (C-1) and (C-2), apply to the structures from the above table.

The following compounds are examples of compounds of the formula (I) or (II).

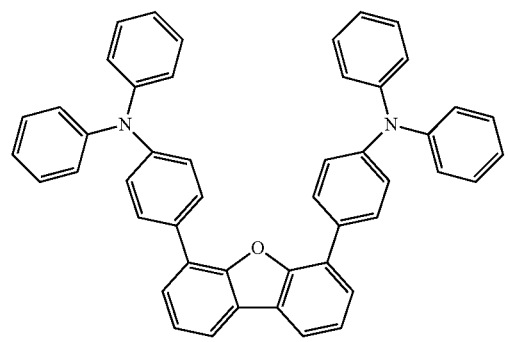

1

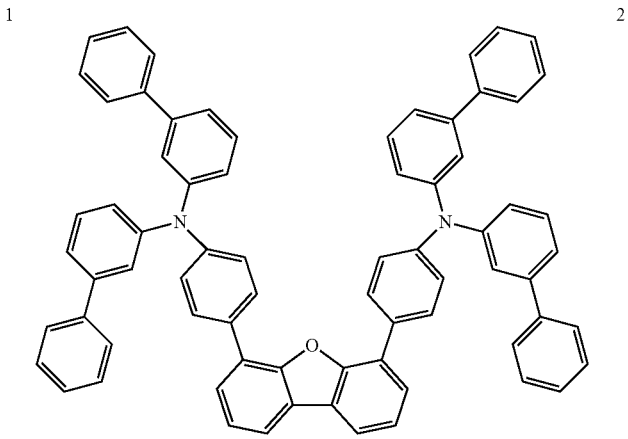

2

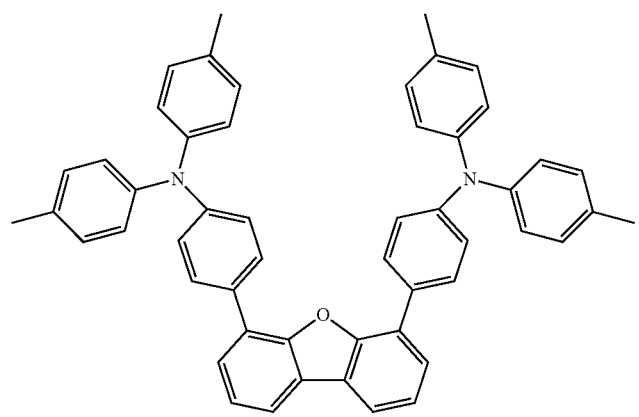

3

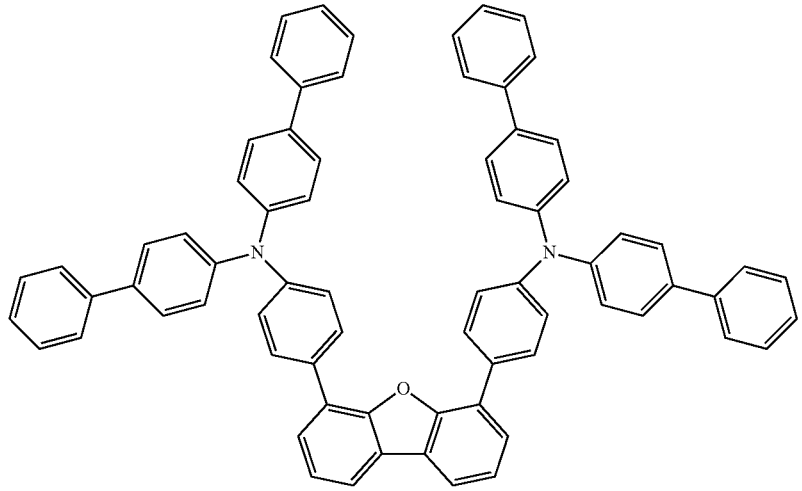
4
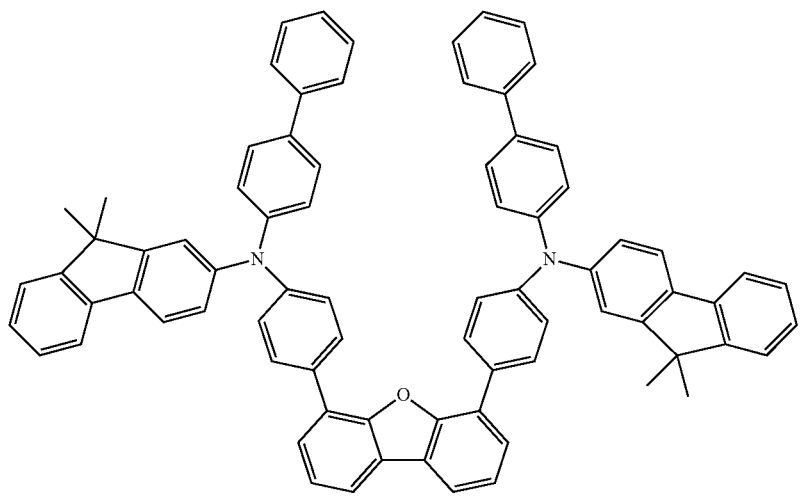
5
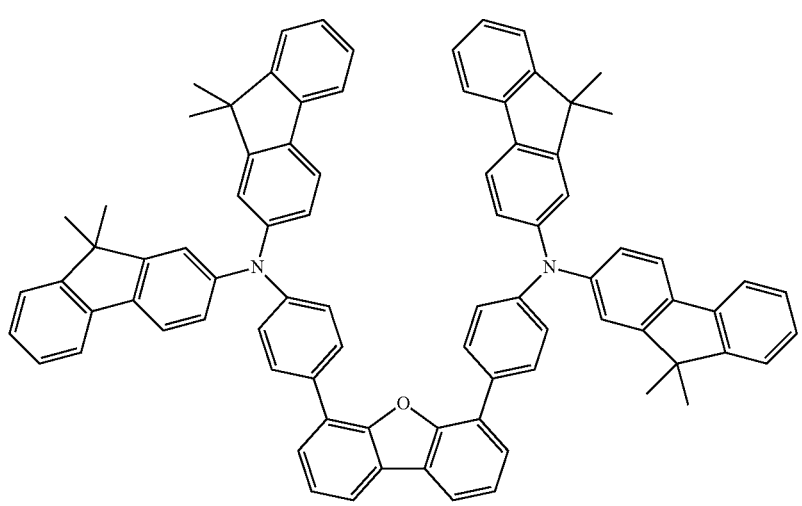
6

-continued
7
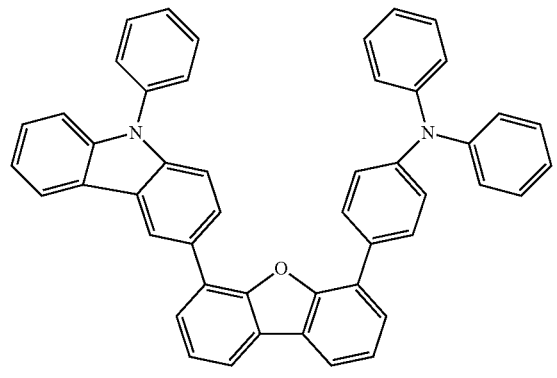
8
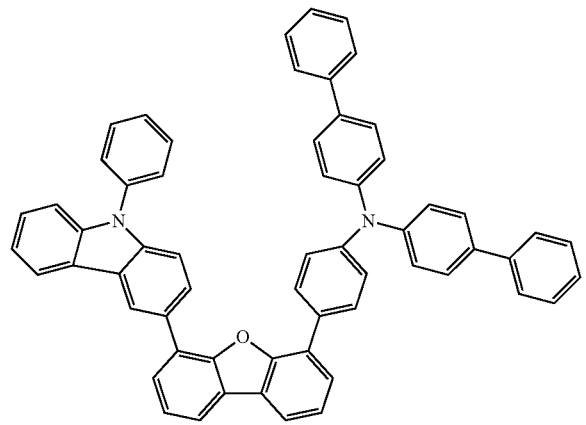
9
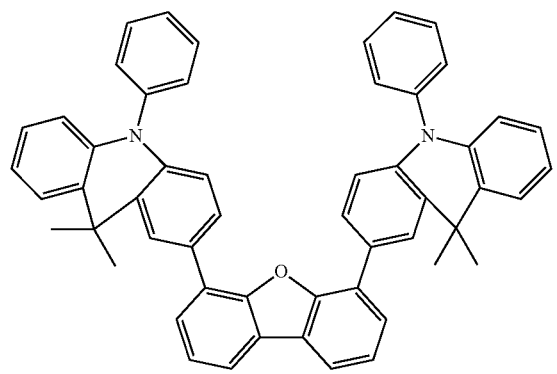
10
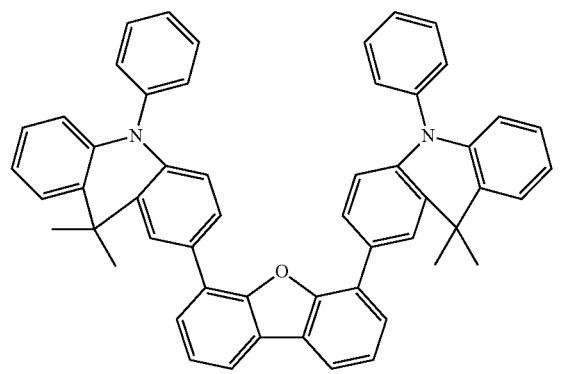
11
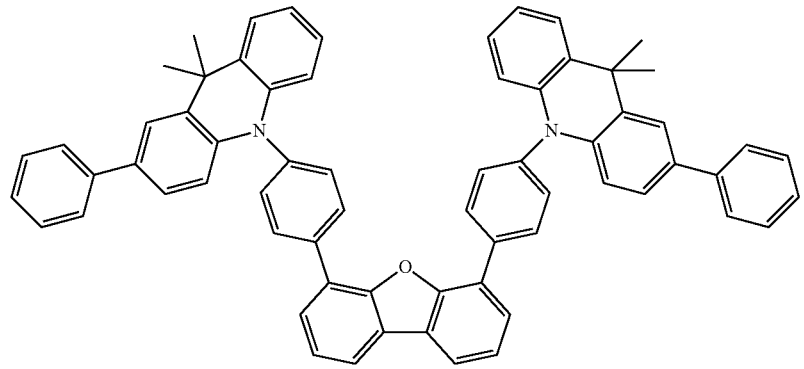
12
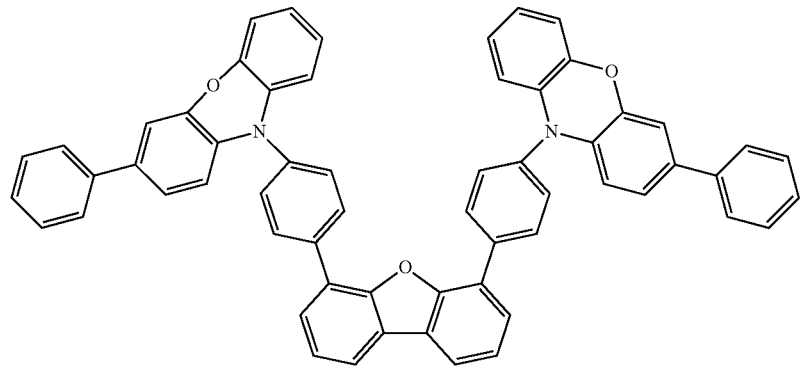

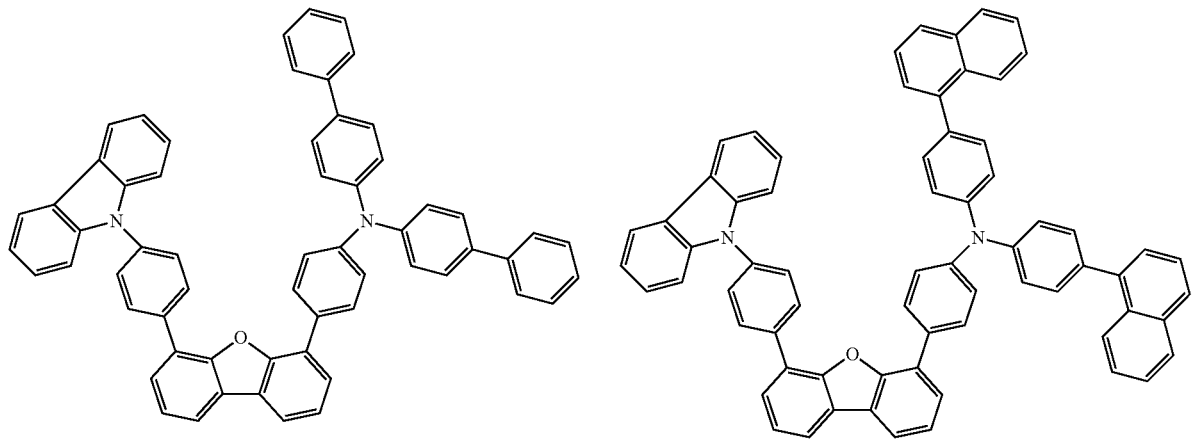
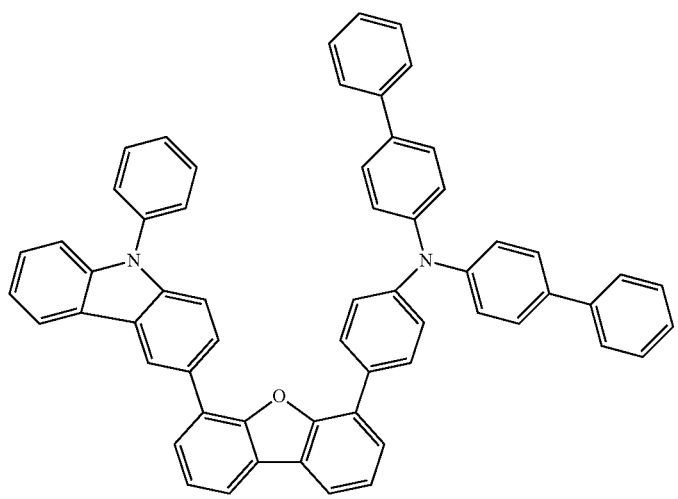
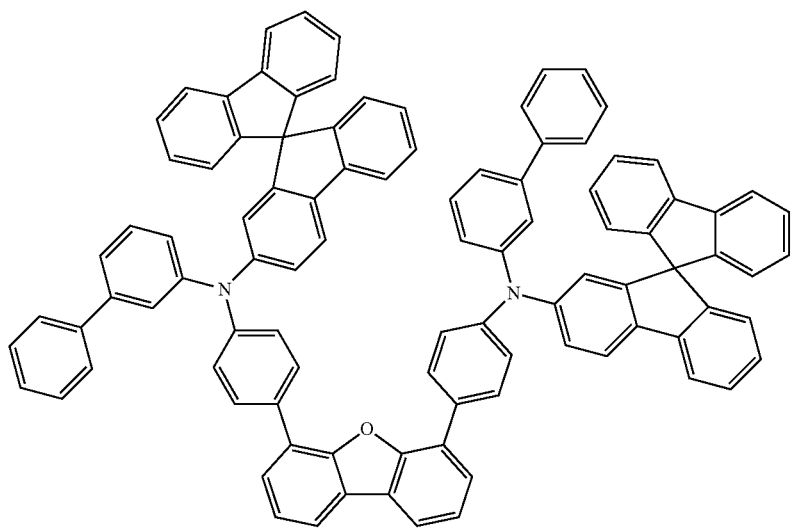

-continued
17
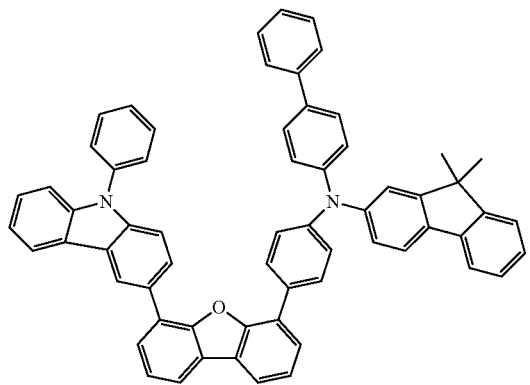
18
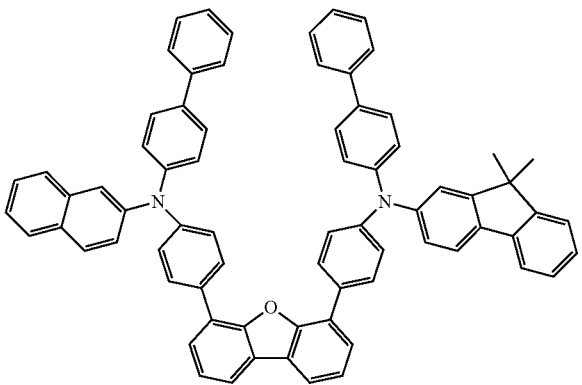
19
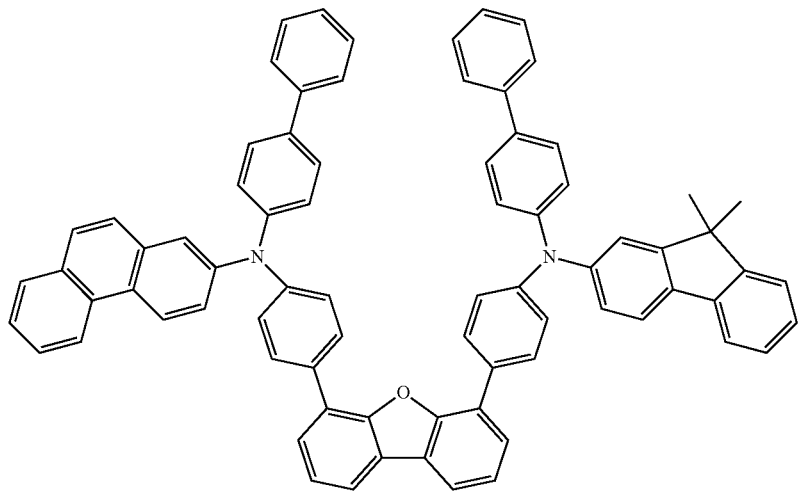
20
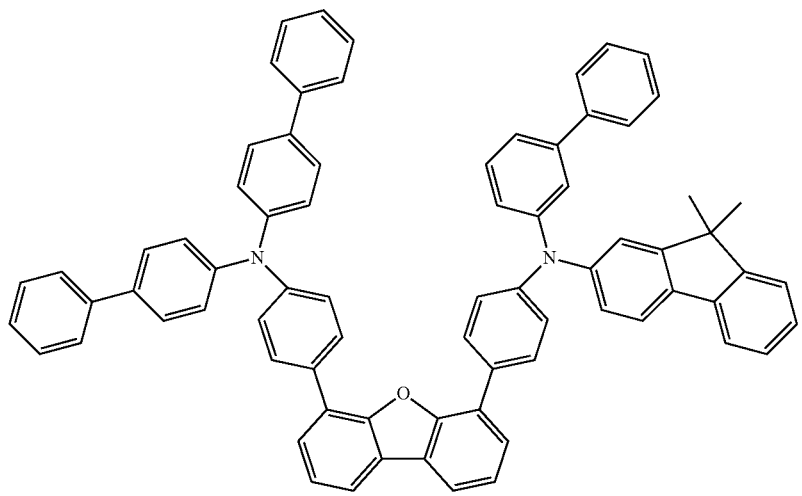

-continued
21
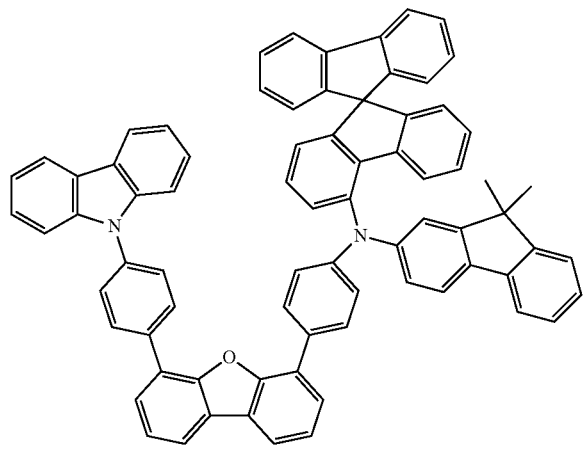
22
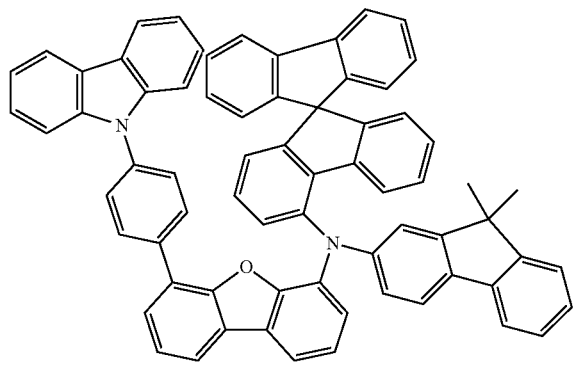
23
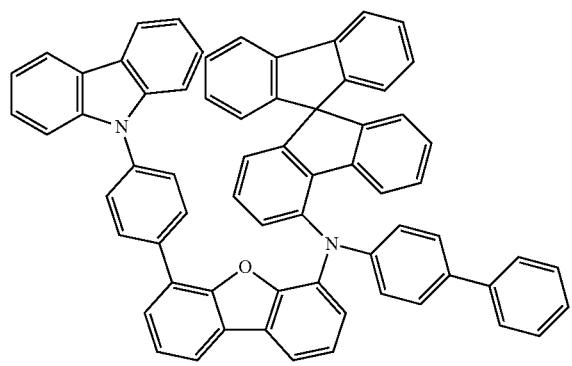
24
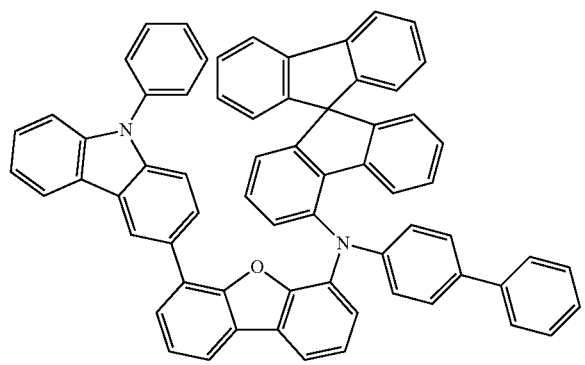
25
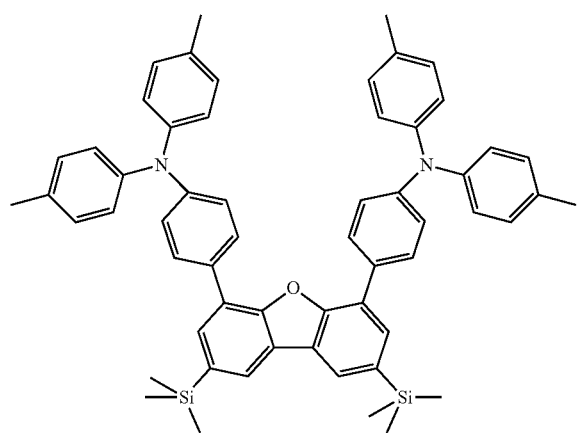

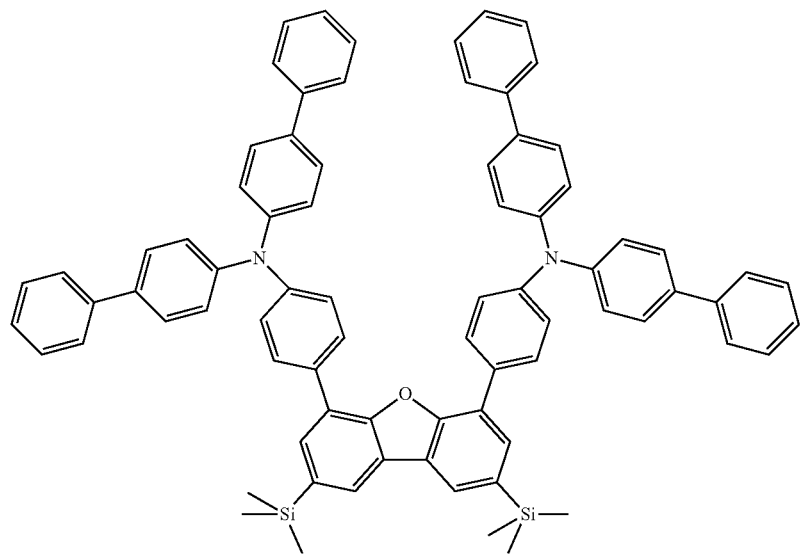
26
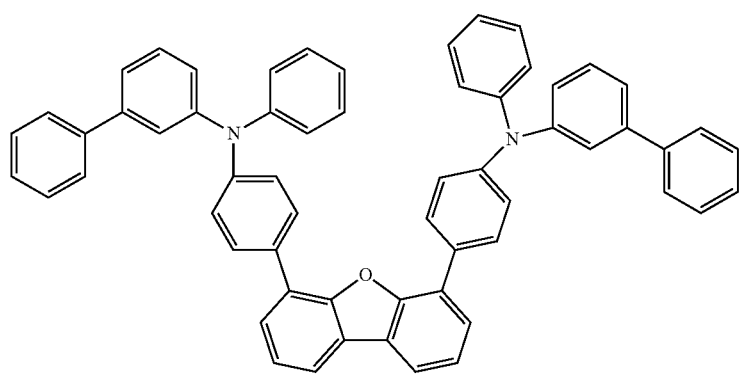
27
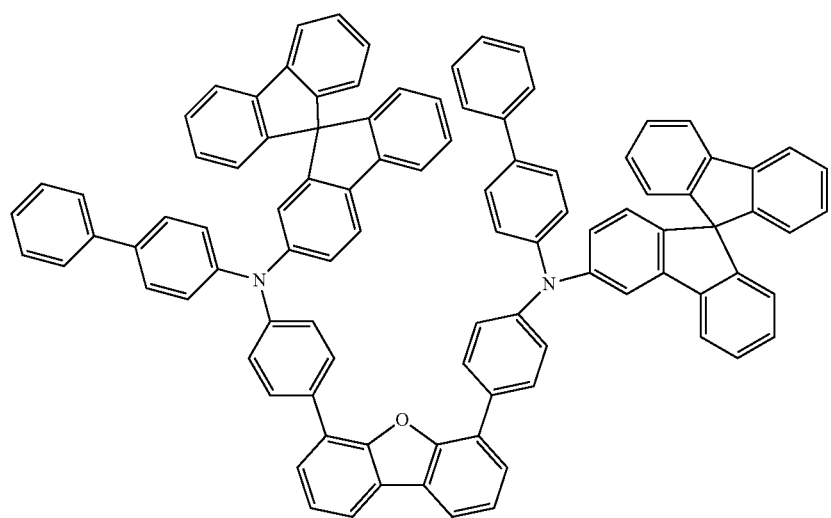
28

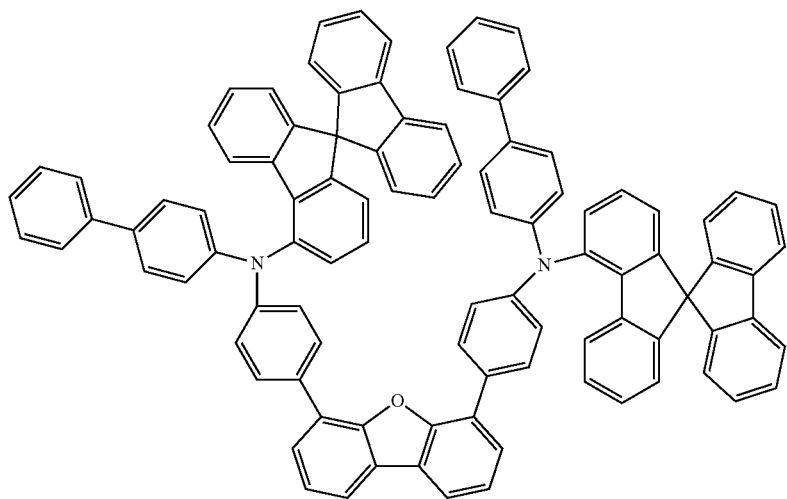
29
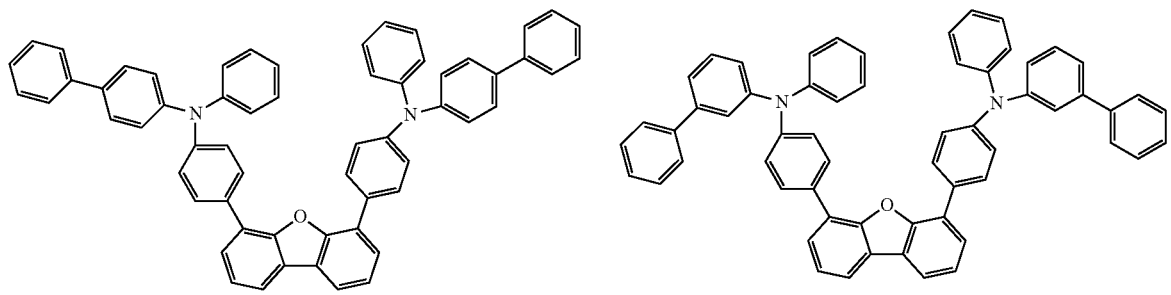
30
31
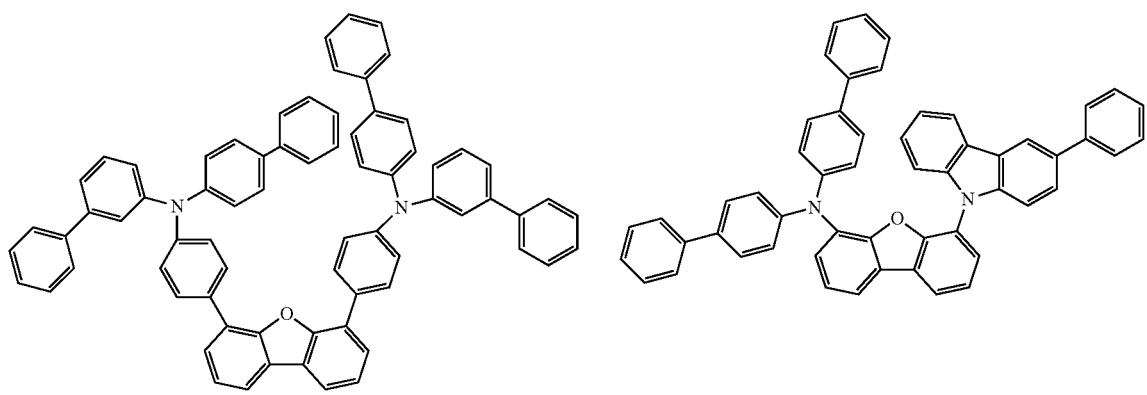
32
33

-continued
34
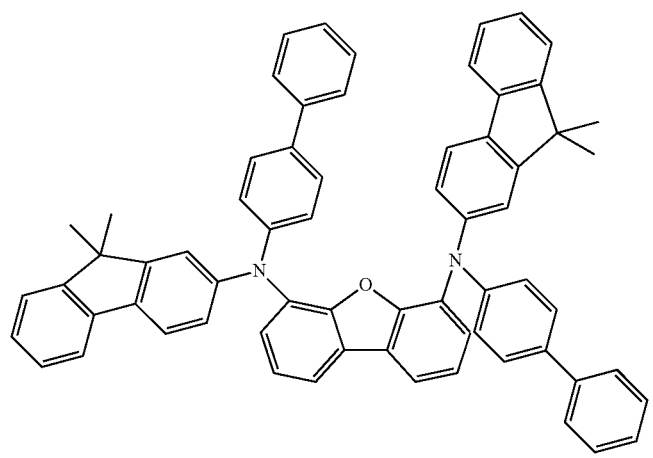
35
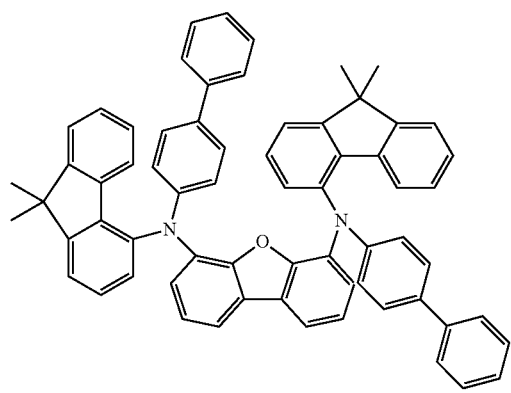
36
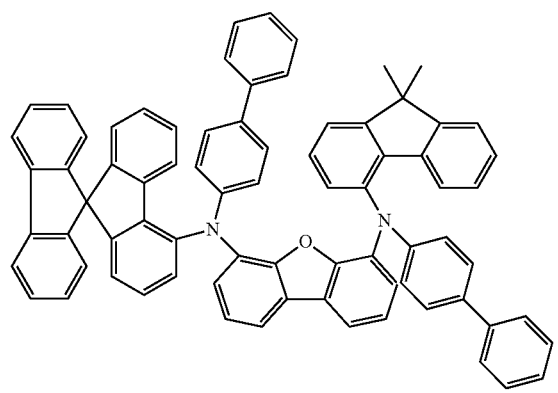
37
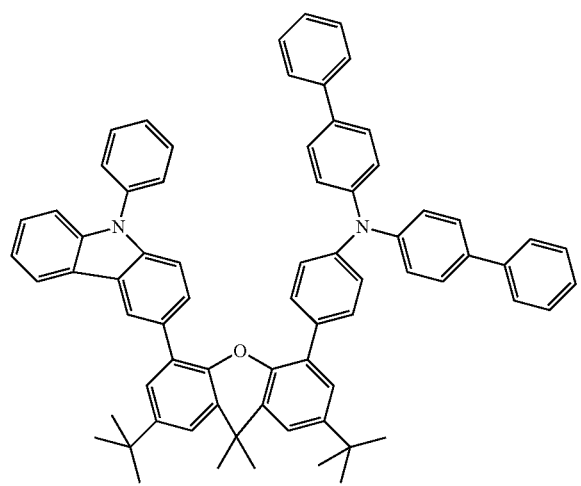
38
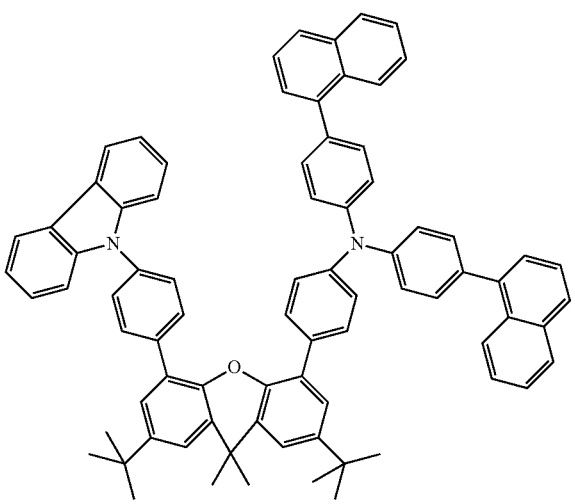

39
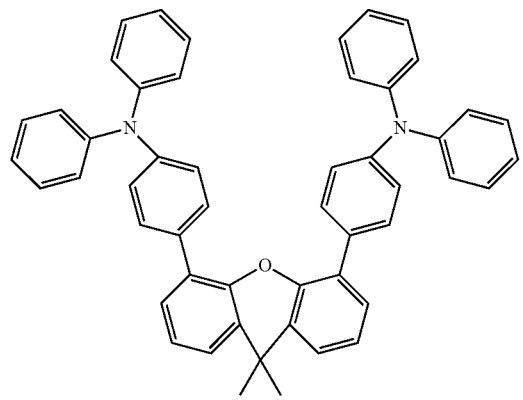
40
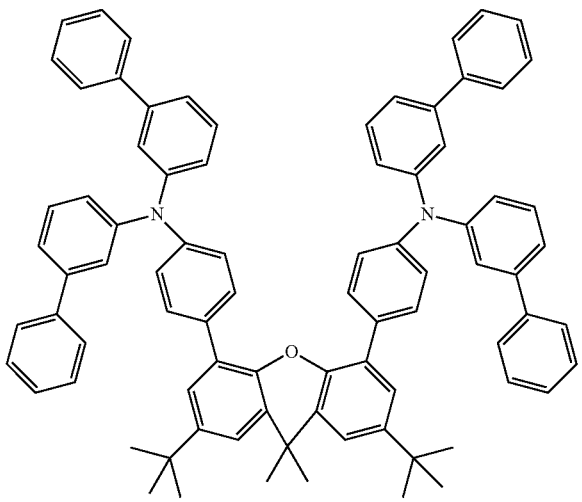
41
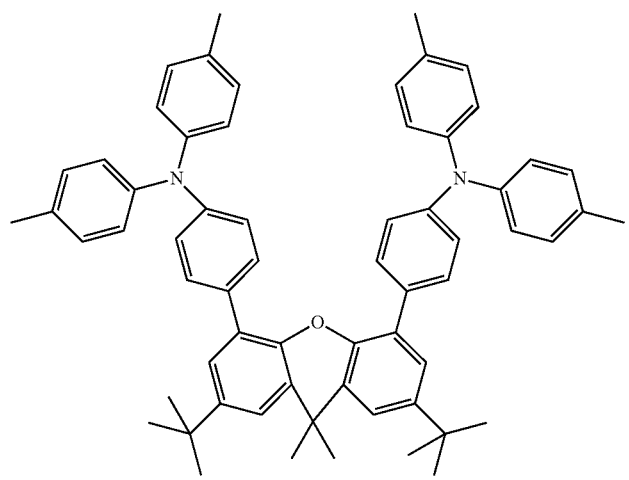
42
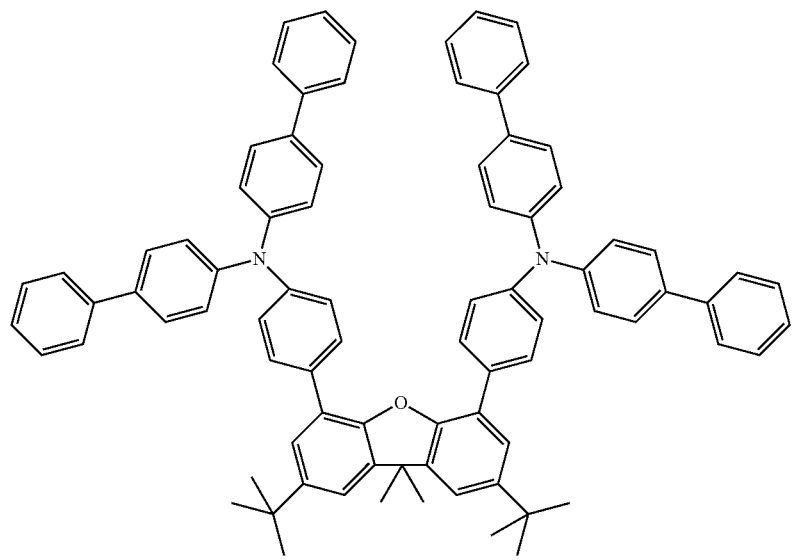

-continued
43
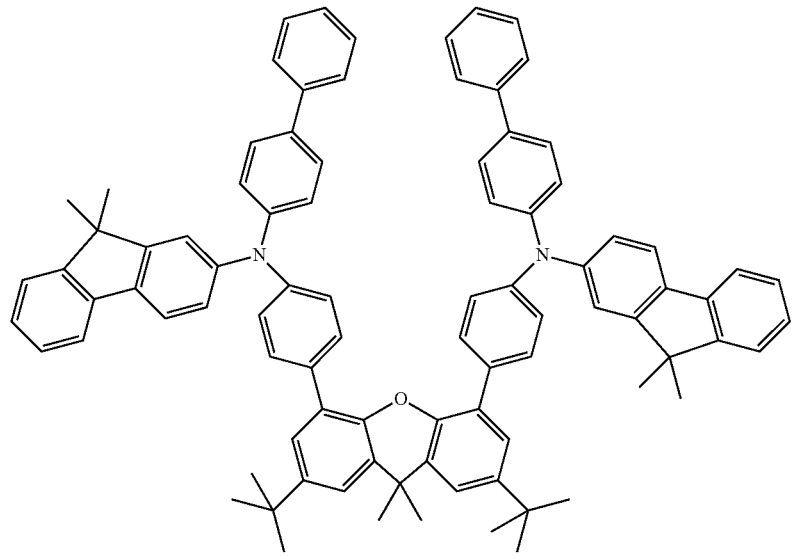
44
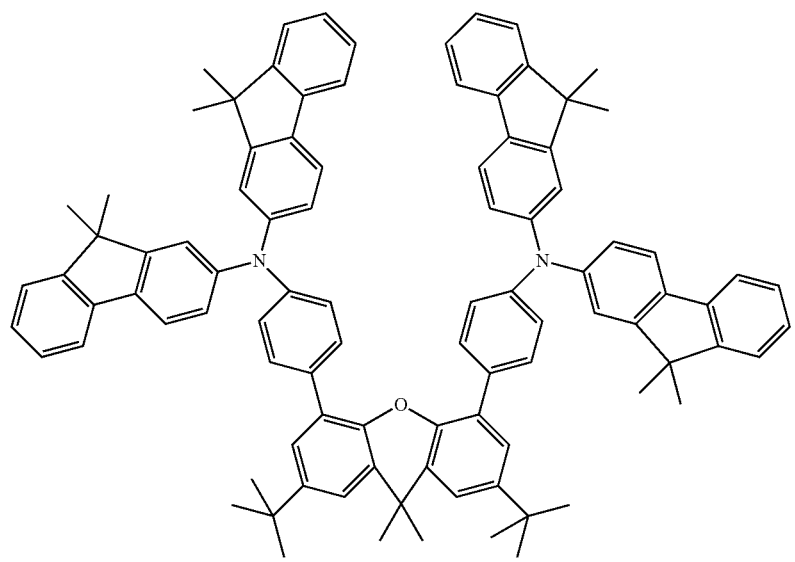
45 46
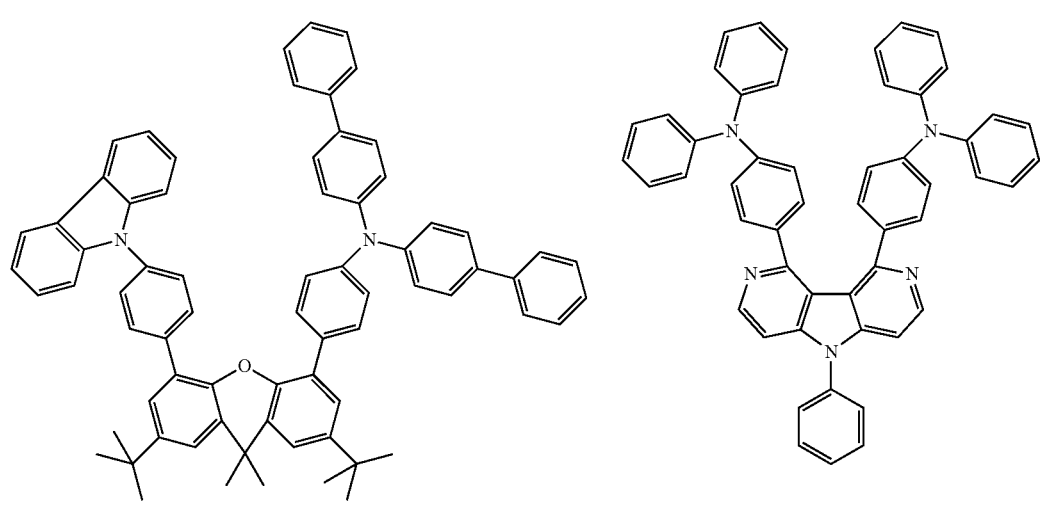

-continued
47
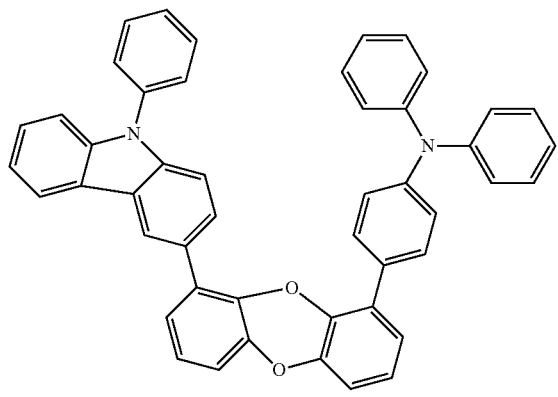
48
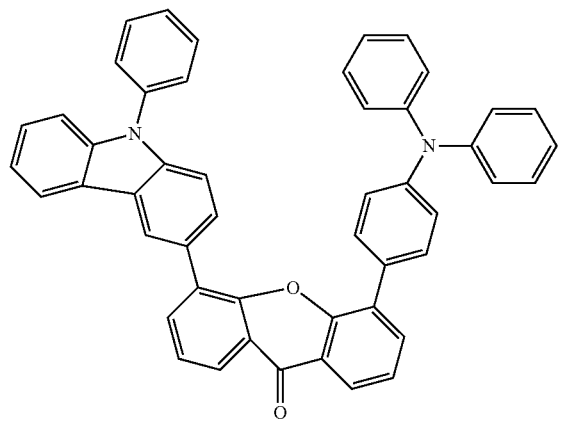
49
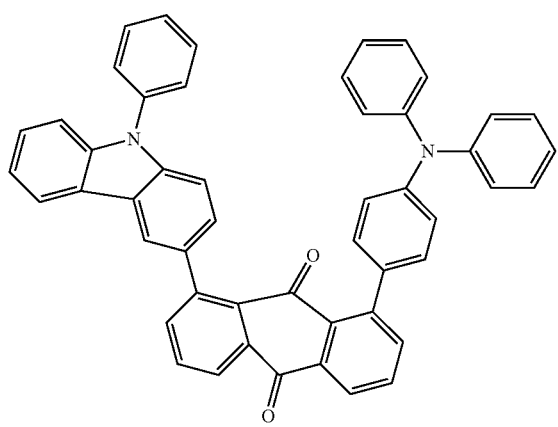
50
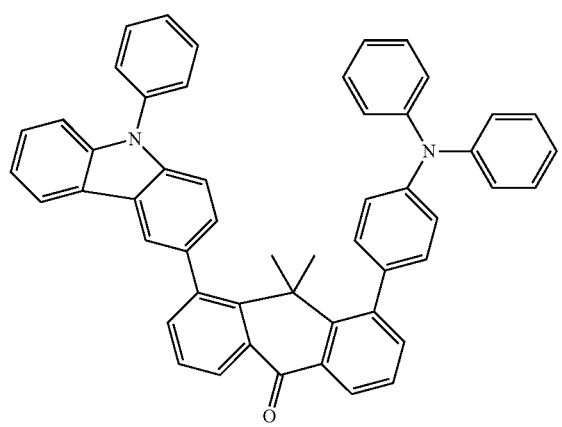
51
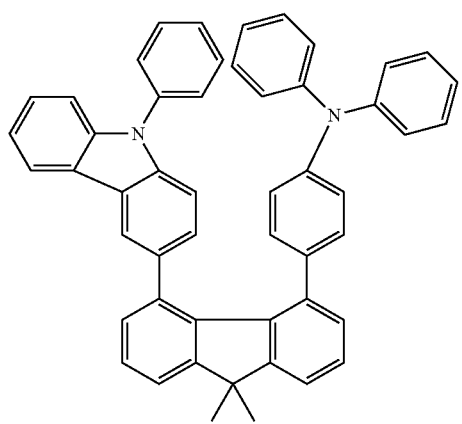
52
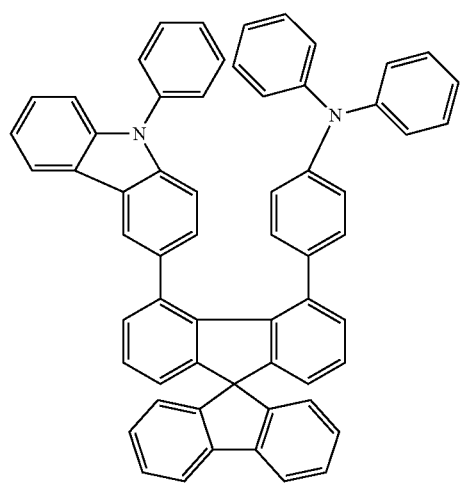

53
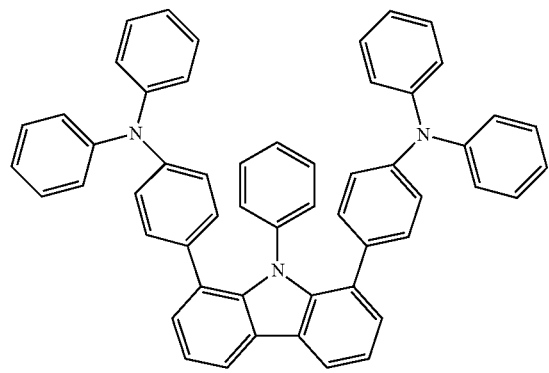
54
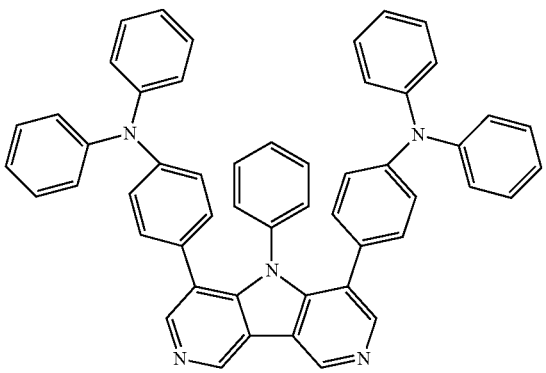
55
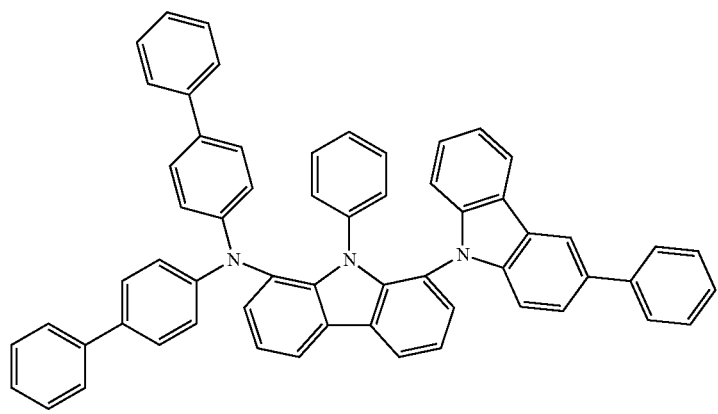
56
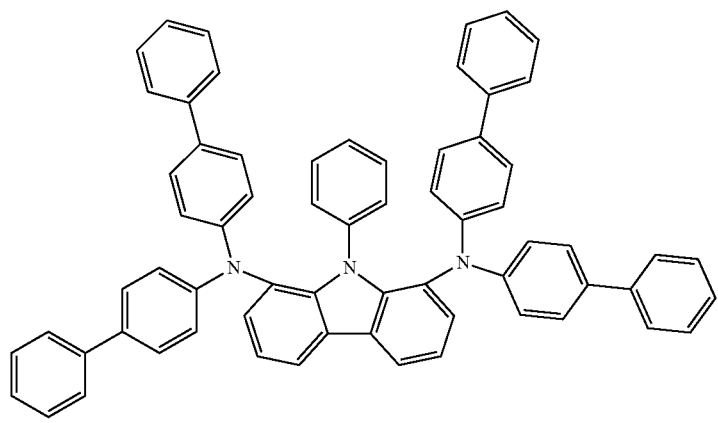
57
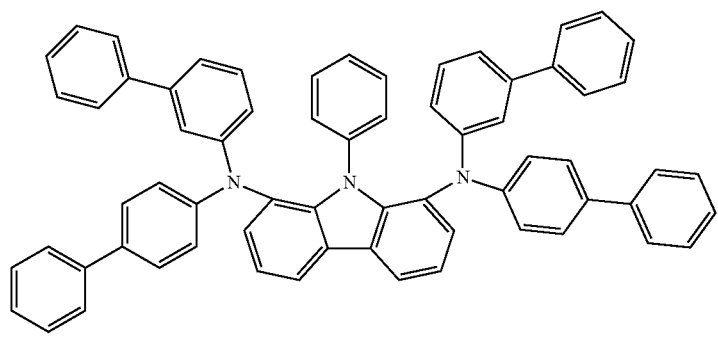

-continued
58
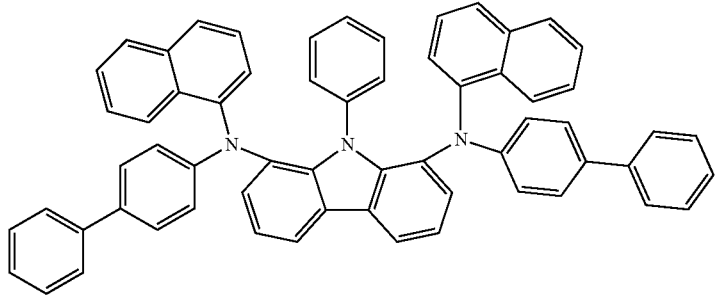
59
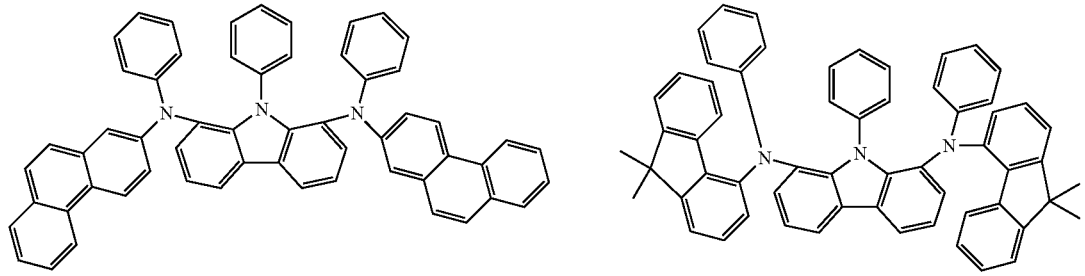
60
61
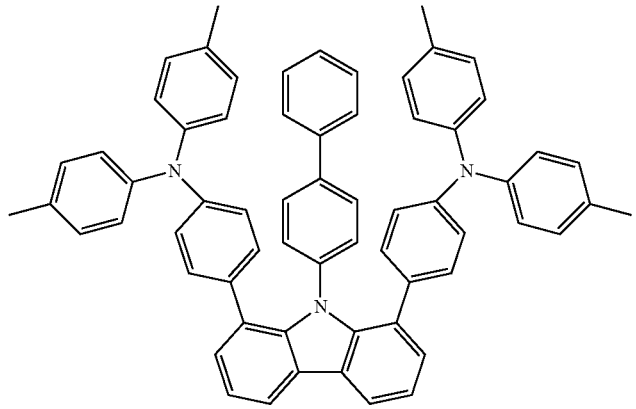
62
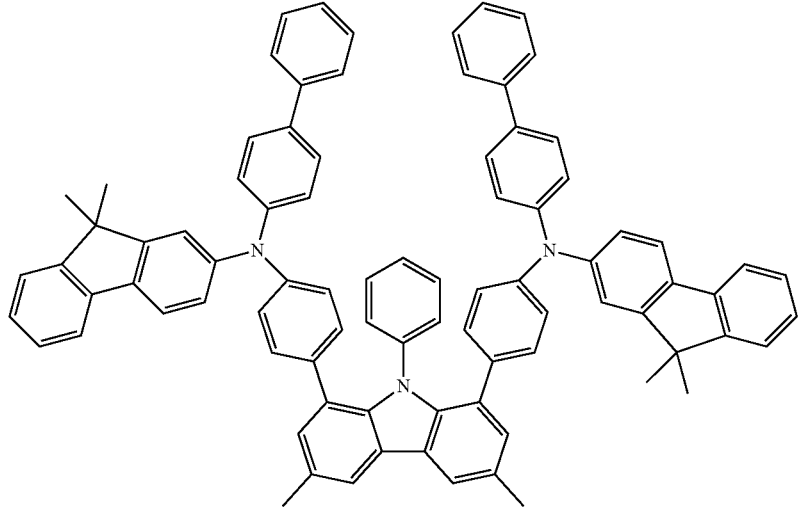

-continued
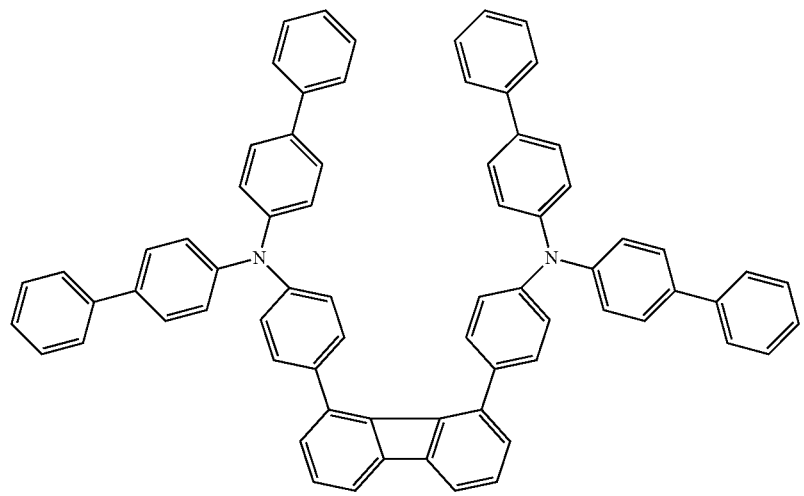
63
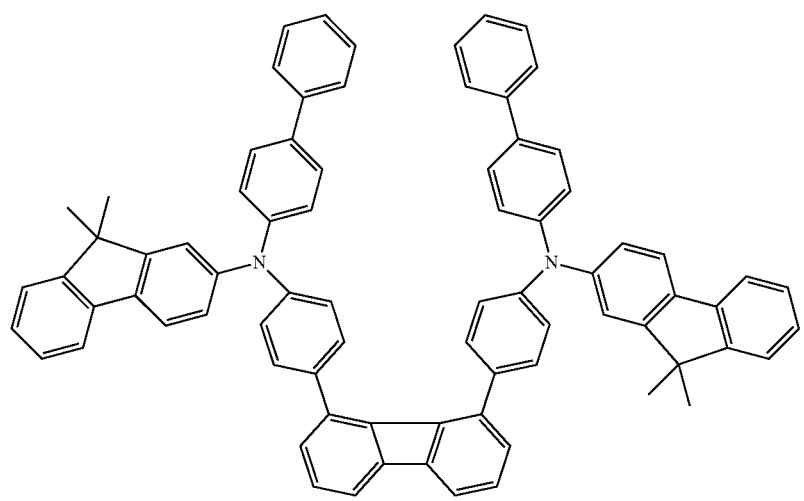
64
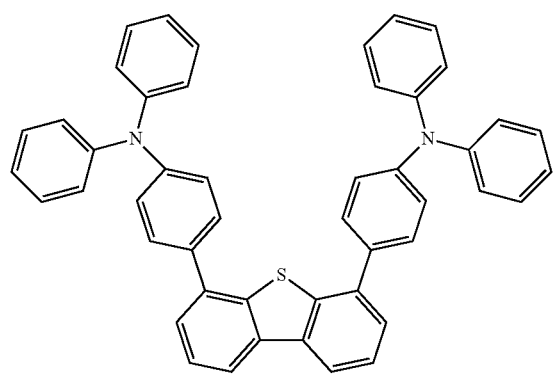
65

-continued
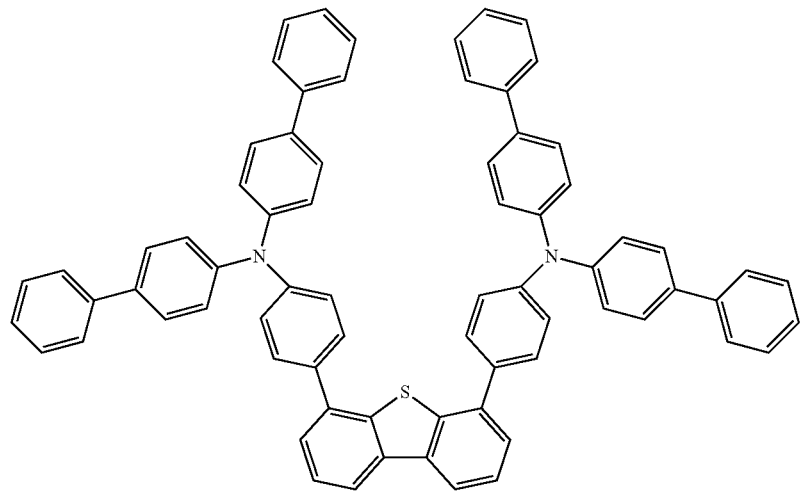
66
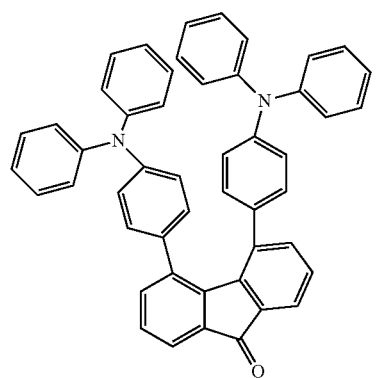
67
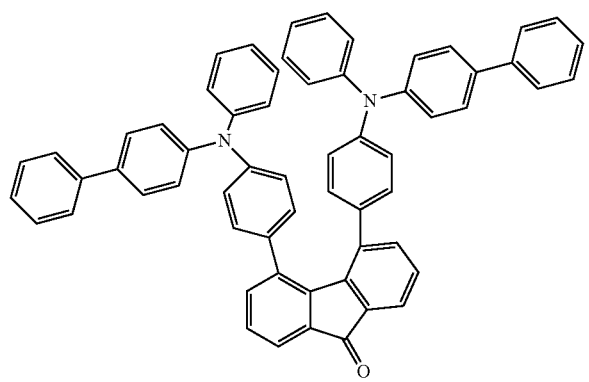
68
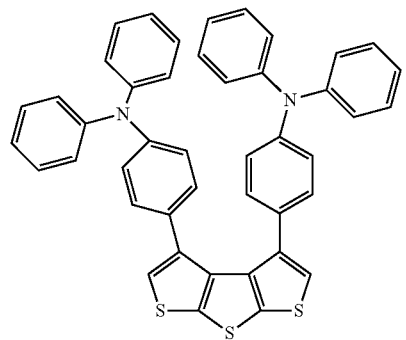
69
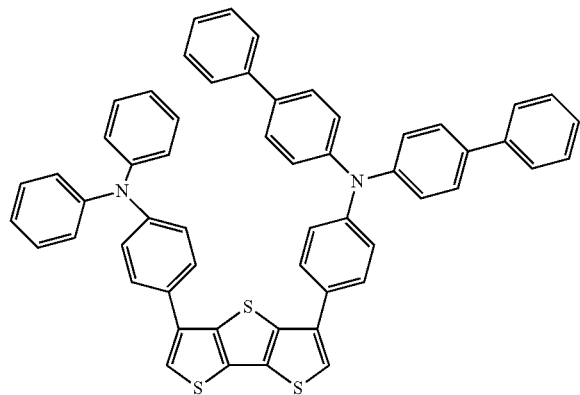
70
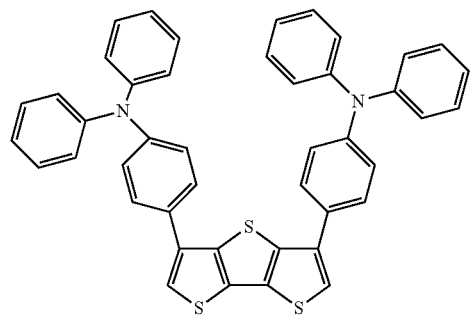
71

The compounds according to the invention can be prepared in accordance with Schemes 1-4.

The corresponding monoboronic acids can be prepared by Suzuki coupling (Scheme 1) or Buchwald coupling (Scheme 2) and subsequent silylation (a or b). Reaction of these monoboronic acids with corresponding aryl bromides or aryl chlorides by Suzuki coupling leads to corresponding target compounds.

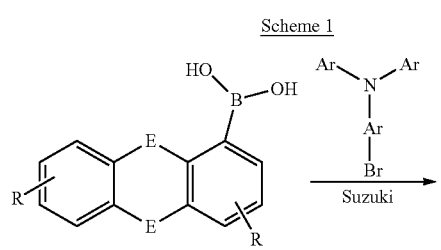

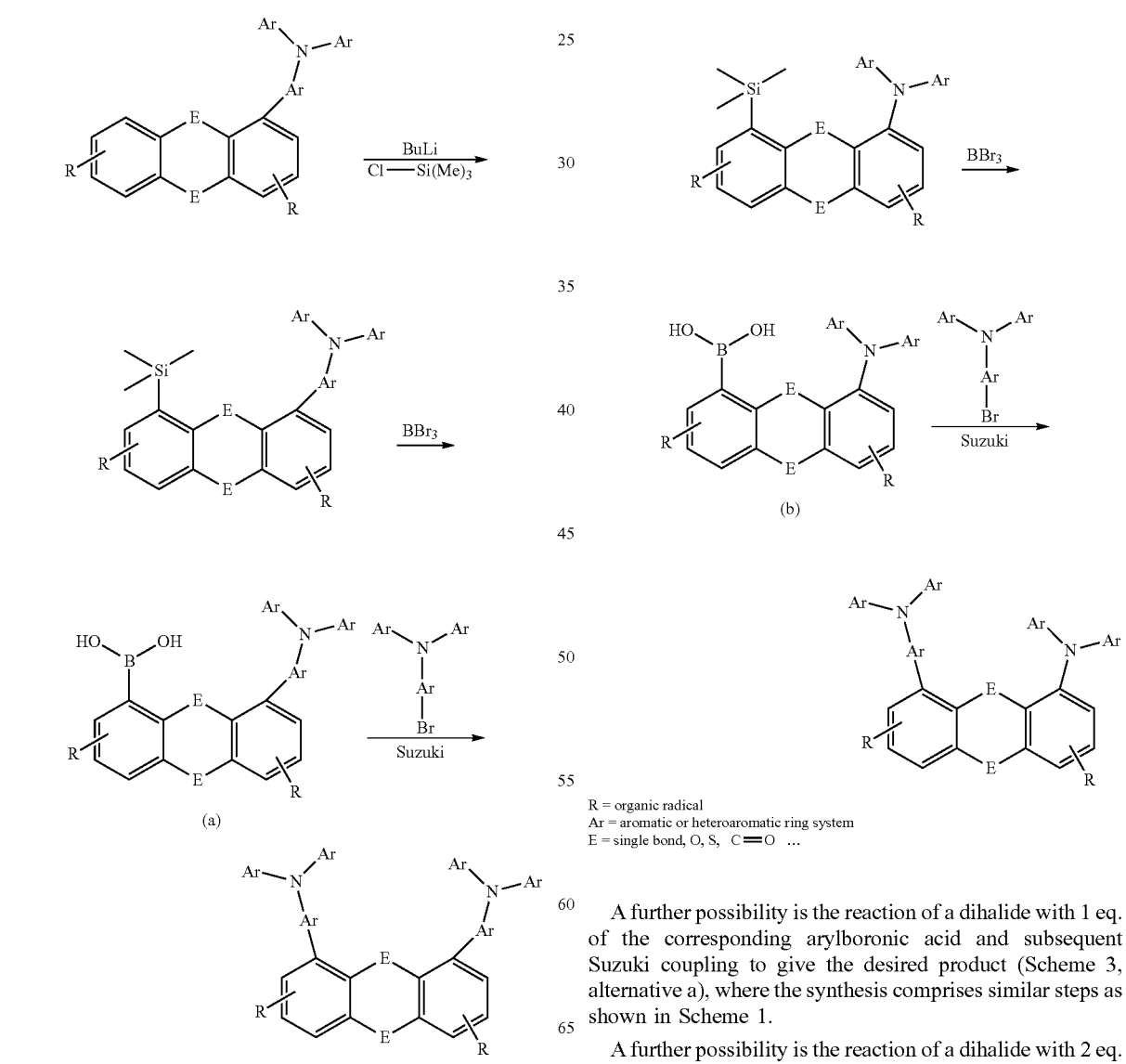

R = organic radical
Ar = aromatic or heteroaromatic ring system
E = single bond, O, S, C═O ...

A further possibility is the reaction of a dihalide with 1 eq. of the corresponding arylboronic acid and subsequent Suzuki coupling to give the desired product (Scheme 3, alternative a), where the synthesis comprises similar steps as shown in Scheme 1.

A further possibility is the reaction of a dihalide with 2 eq. of a corresponding boronic acid (Scheme 3, alternative b)

Scheme 3
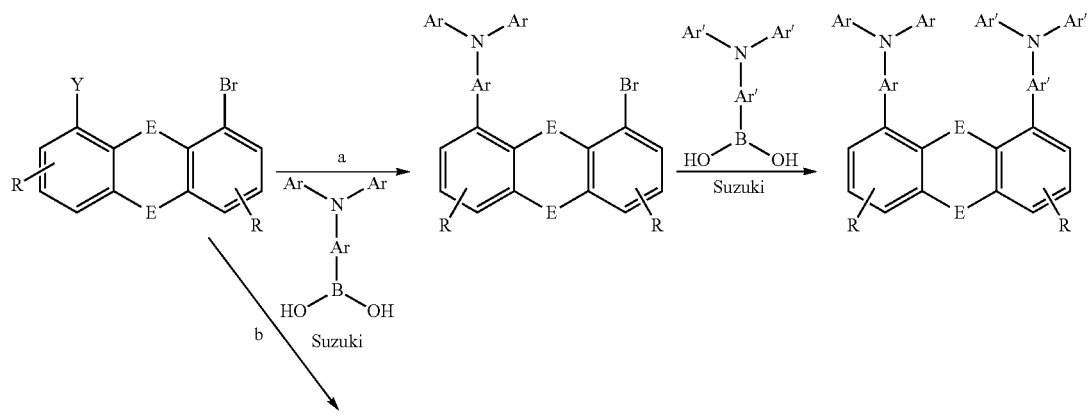
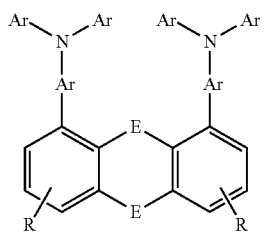
R = organic radical
Ar, Ar' = aromatic or heteroaromatic ring system
E = single bond, O, S, C=O ...
Y = I, Br, ...
A synthetic route starting from an unfunctionalised starting compound, such as, for example, a dibenzofuran derivative, is shown below (Scheme 4).
Scheme 4
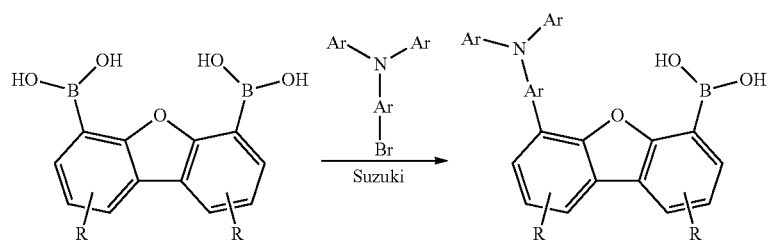

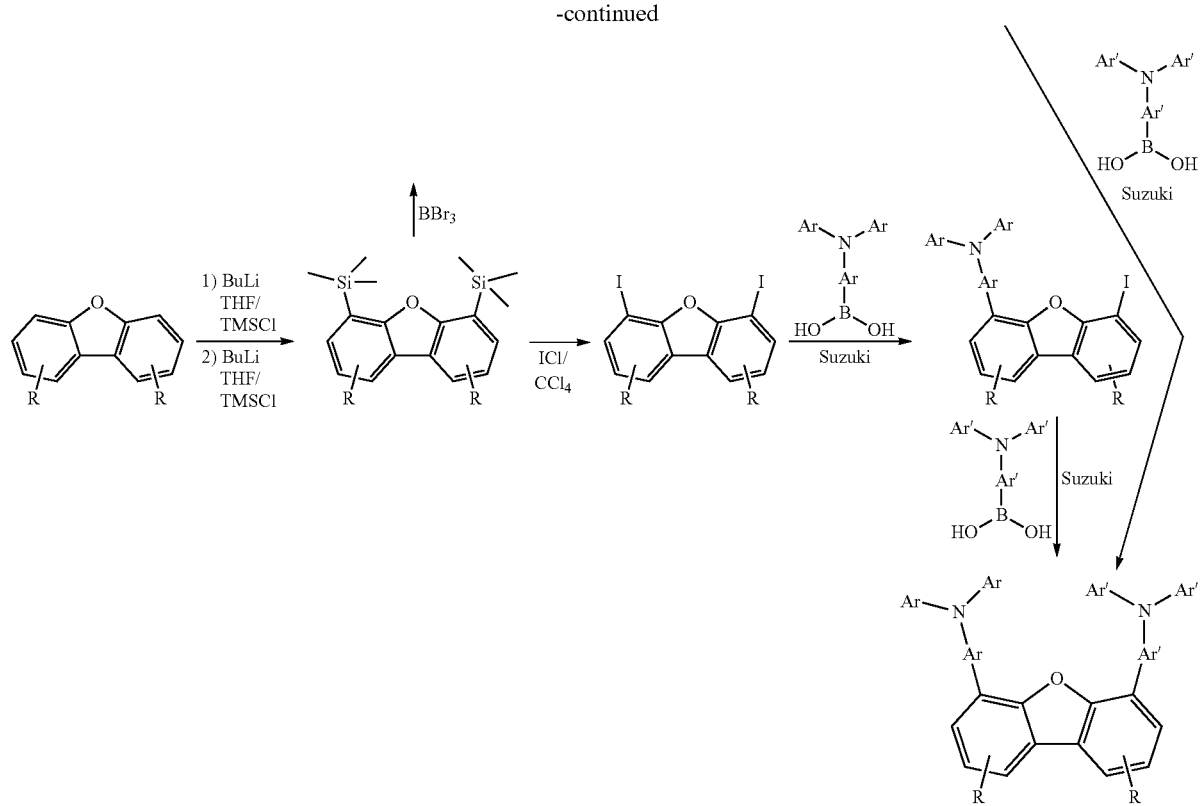

R = organic radical
Ar, Ar' = aromatic or heteroaromatic ring system

The processes shown for the synthesis of the compounds are to be understood as being illustrative. The person skilled in the art will be able to develop alternative synthetic routes within the bounds of his general expert knowledge, The invention furthermore relates to the use of a compound of the formula (I) or (II) in an electronic device, preferably in a hole-transporting and/or in an emitting layer.

The electronic device according to the invention is preferably selected from organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs). The electronic device is particularly preferably an OLED.

The organic layer comprising the compound of the formula (I) or (II) is preferably a layer having a hole-transporting function. It is particularly preferably a hole-injection layer, a hole-transport layer, an electron-blocking layer or an emitting layer.

A hole-transport layer in accordance with the present application is a layer having a hole-transporting function which is located between anode and emitting layer.

Hole-injection layers and electron-blocking layers in the sense of the present invention are taken to be specific embodiments of hole-transport layers. In the case of a plurality of hole-transport layers between anode and emitting layer, a hole-injection layer is a hole-transport layer which is directly adjacent to the anode or is only separated therefrom by a single coating of the anode. In the case of a plurality of hole-transport layers between anode and emitting layer, an electron-blocking layer is the hole-transport layer which is directly adjacent to the emitting layer on the anode side.

If the compound of the formula (I) or (II) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (I) or (II) then additionally comprises one or more p-dopants. In accordance with the present invention, the p-dopants employed are preferably organic electron-acceptor compounds which are able to oxidise one or more of the other compounds of the mixture. Particularly preferred embodiments of p-dopants are the compounds disclosed in WO 2011/073149, EP 1968131, EP 2276085, EP 2213662, EP 1722602, EP 2045848, DE 102007031220, U.S. Pat. No. 8,044,390, U.S. Pat. No. 8,057,712, WO 2009/003455, WO 2010/094378, WO 2011/120709, US 2010/0096600 and WO 2012/095143.

In a further preferred embodiment of the invention, the compound of the formula (I) or (II) is present in the electronic device as hole-transport material in a hole-transporting layer in combination with a hexaazatriphenylene derivative, as described in US 2007/0092755. The hexaazatriphenylene derivative here is particularly preferably employed in a separate layer.

Furthermore, the organic layer comprising the compound of the formula (I) or (II) is preferably an emitting layer.

In a further embodiment of the present invention, the compound of the formula (I) or (II) is present in the electronic device as matrix material in combination with one or more dopants, preferably phosphorescent dopants.

The term phosphorescent dopants typically encompasses compounds in which the light emission takes place through a spin-forbidden transition, for example a transition from an excited triplet state or a state having a higher spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present application, all luminescent iridium, platinum or copper complexes are regarded as phosphorescent compounds. Examples of phosphorescent dopants are indicated in a following section.

A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the greater.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the larger. In individual cases, however, the proportion of an individual matrix material in the system may be smaller than the proportion of an individual dopant.

In a further preferred embodiment of the invention, the compounds of the formula (I) or (II) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant is employed in the mixed-matrix system.

Preferred phosphorescent dopants for use in mixed-matrix systems are the preferred phosphorescent dopants indicated below.

Apart from cathode, anode and the layer comprising the compound of the formula (I) or (II), the electronic device may also comprise further layers. These are selected, for example, from in each case one or more hole-injection layers, hole-transport layers, hole-blocking layers, emitting layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, Multiphoton Organic EL Device Having Charge Generation Layer) and/or organic or inorganic p/n junctions. However, it should be pointed out that each of these layers does not necessarily have to be present.

The sequence of the layers of the organic electroluminescent device is preferably the following:

anode/hole-injection layer/hole-transport layer/emitting layer/electron-transport layer/electron-injection layer/cathode.

It should be pointed out again here that not all of the said layers have to be present, and/or that further layers may additionally be present.

The organic electroluminescent device according to the invention may comprise a plurality of emitting layers. In this case, these emission layers particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). It should be noted that, for the generation of white light, an emitter compound used individually which emits in a broad wavelength range may also be suitable instead of a plurality of emitter compounds emitting in colour.

Preferred embodiments of the functional layers and the functional materials of the device according to the invention follow:

Examples of phosphorescent dopants are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention.

Explicit examples of phosphorescent dopants are shown in the following table.

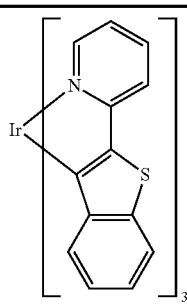
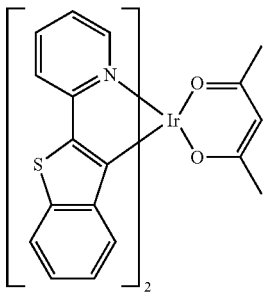
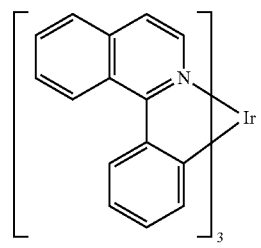
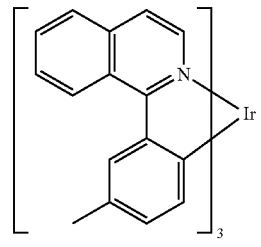
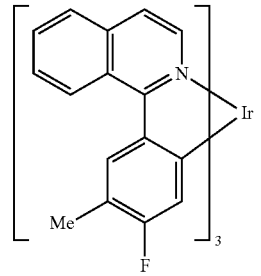
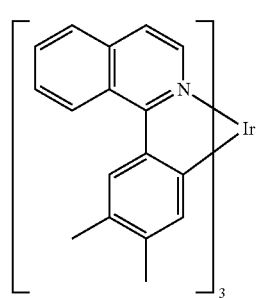
-continued
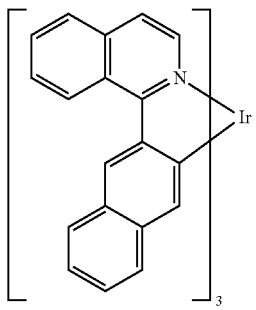
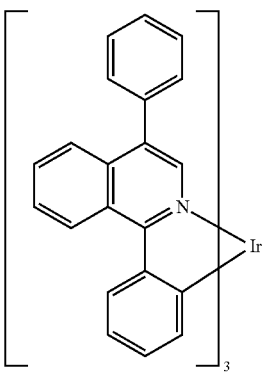
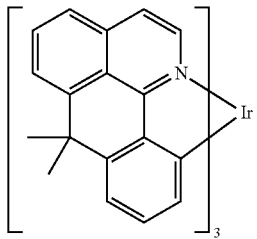
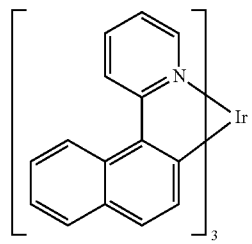
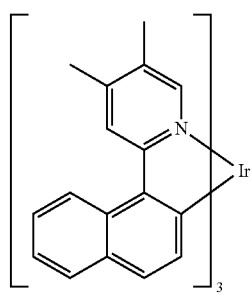

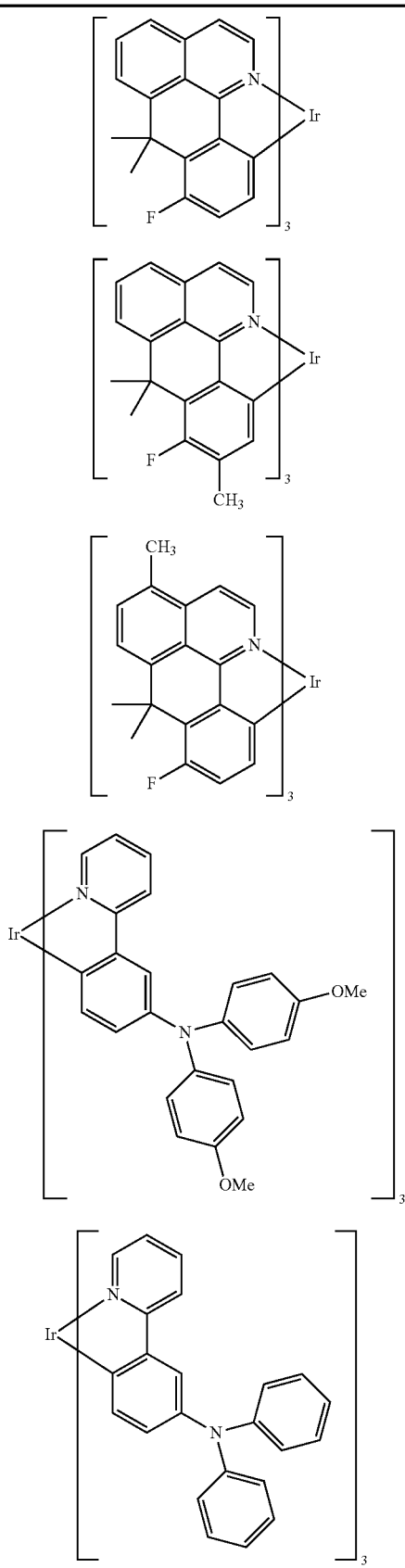
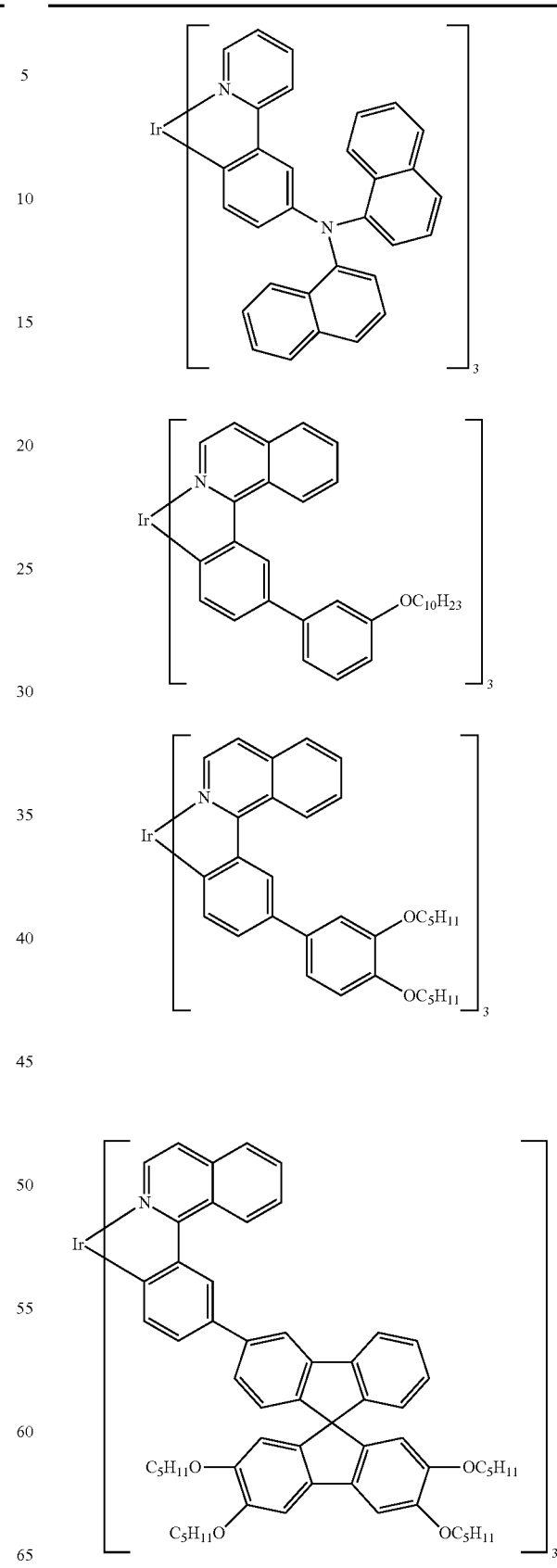

-continued
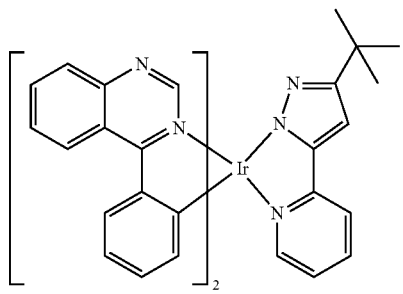
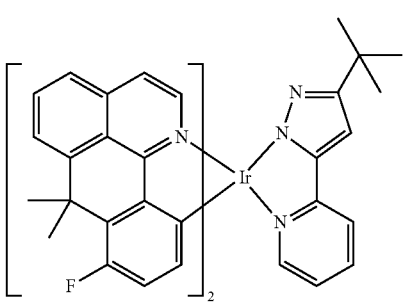
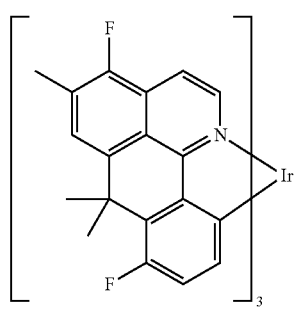
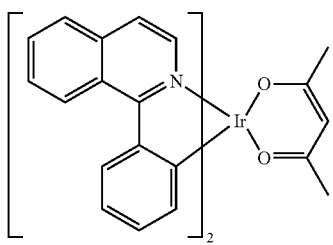
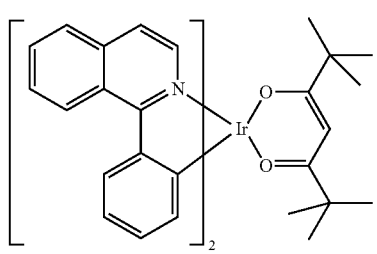
-continued
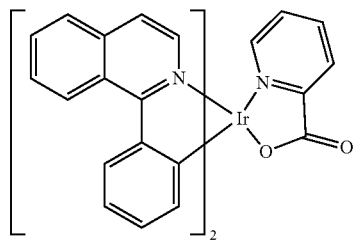
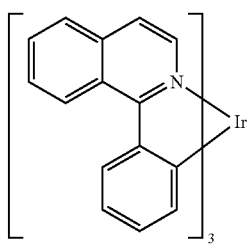
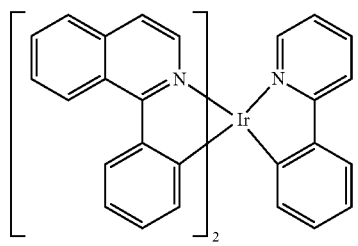
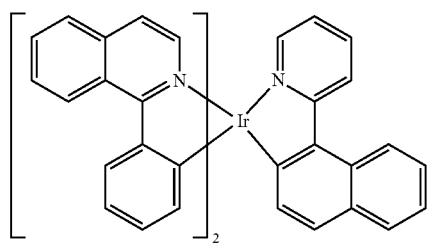
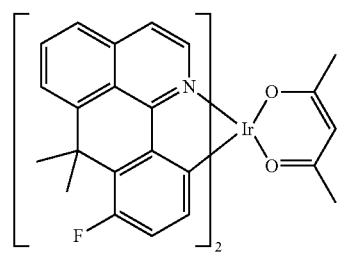
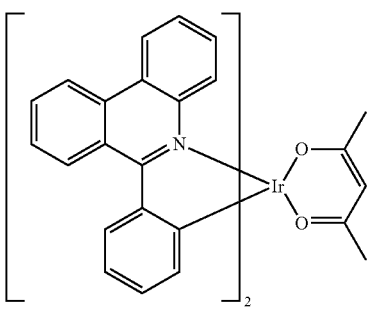

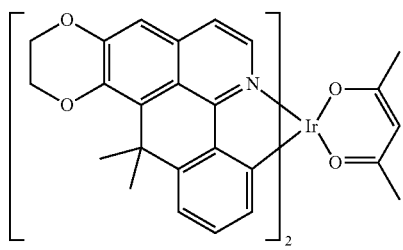
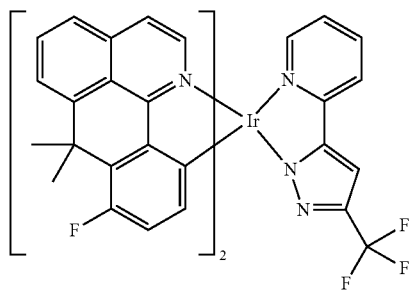
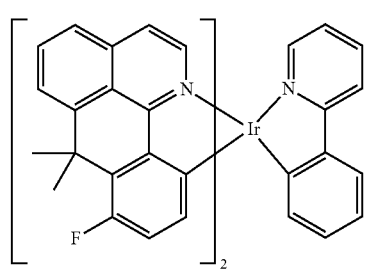
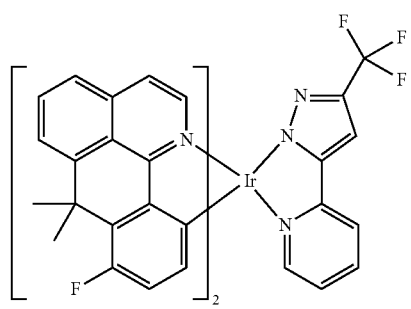
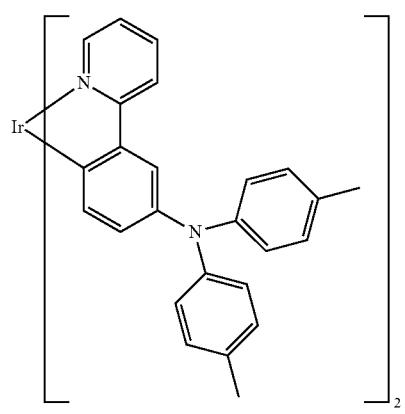
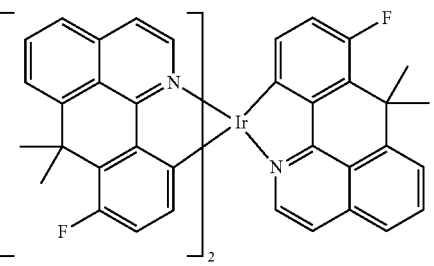
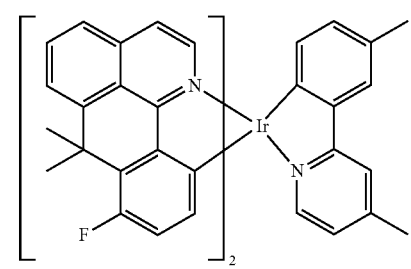
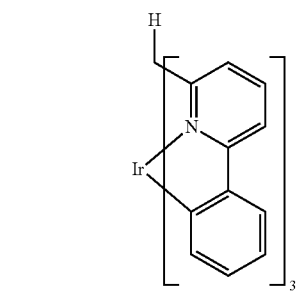
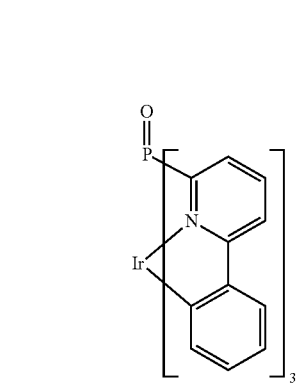
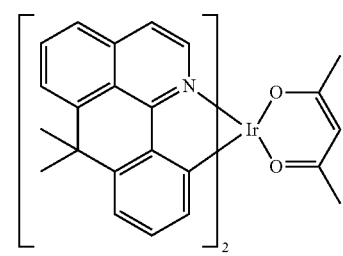

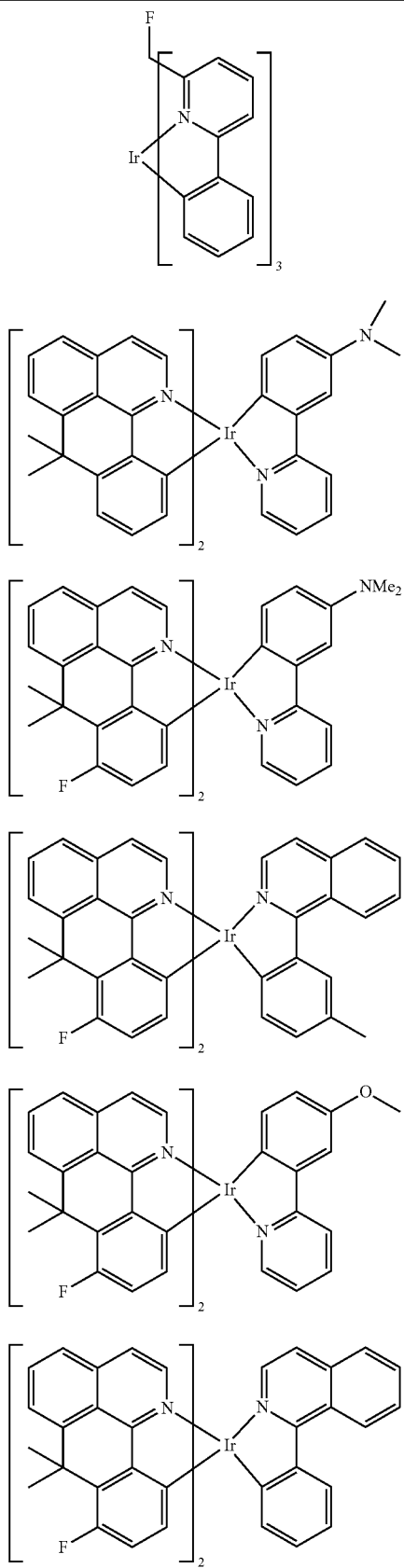
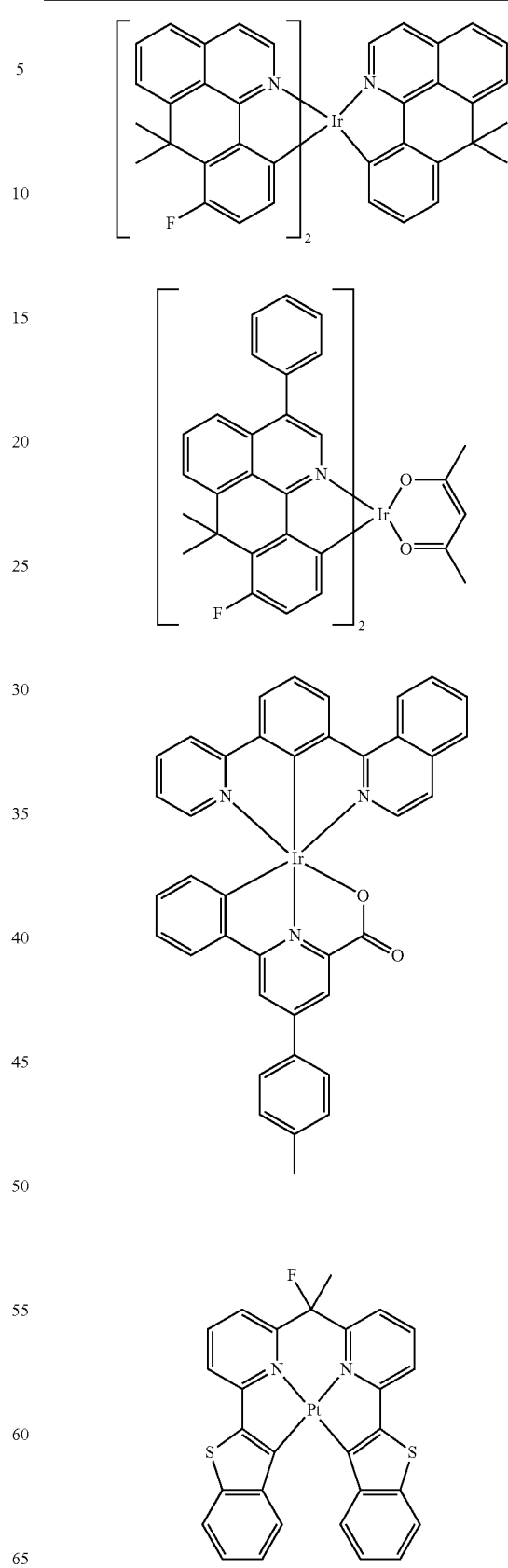

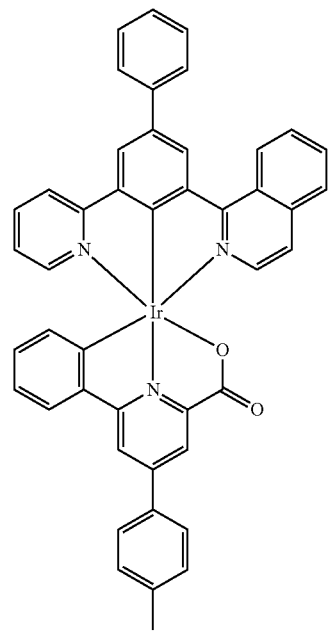
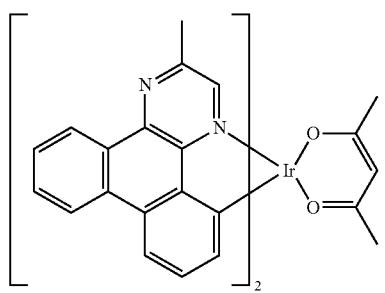
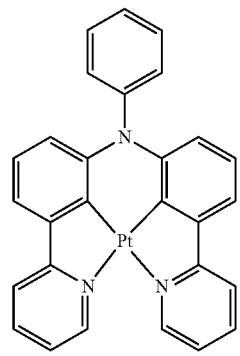
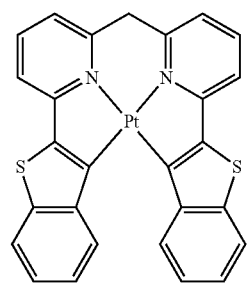
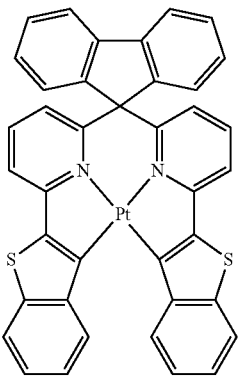
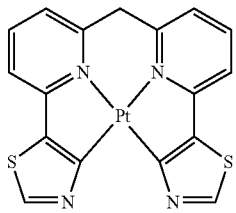
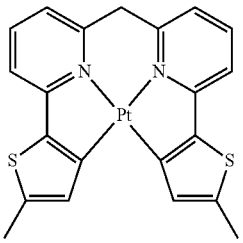
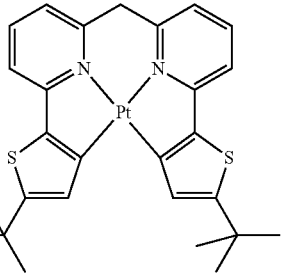
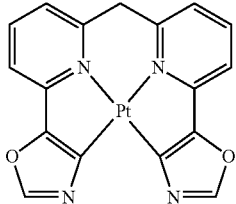
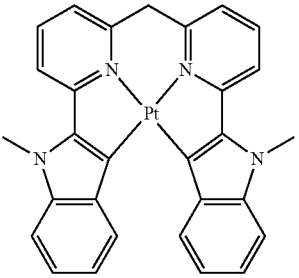

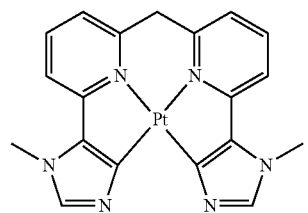
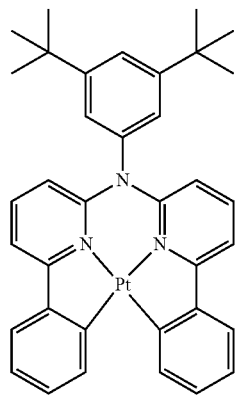
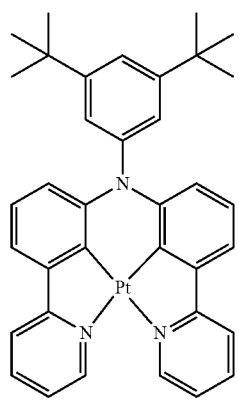
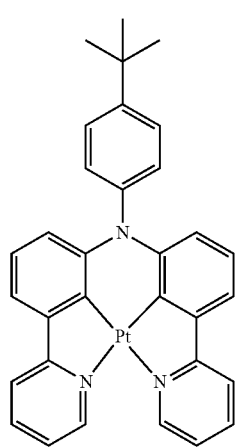
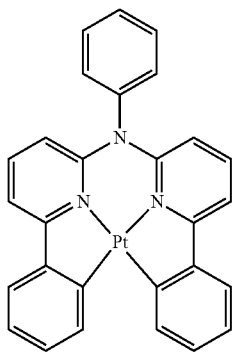
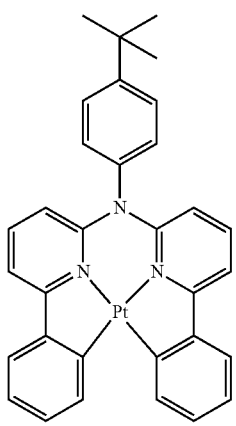
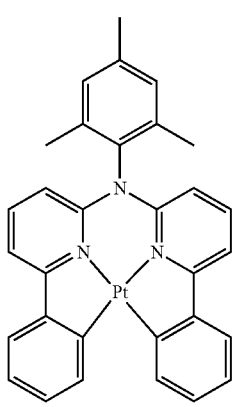
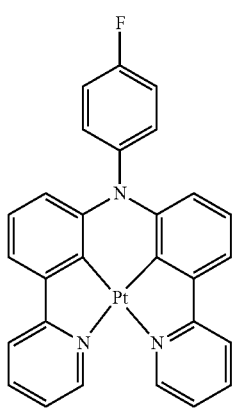

69
-continued
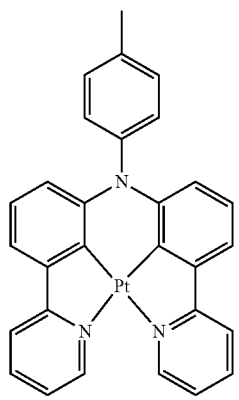
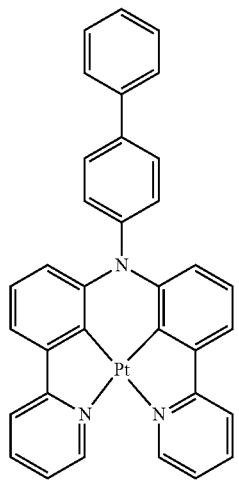
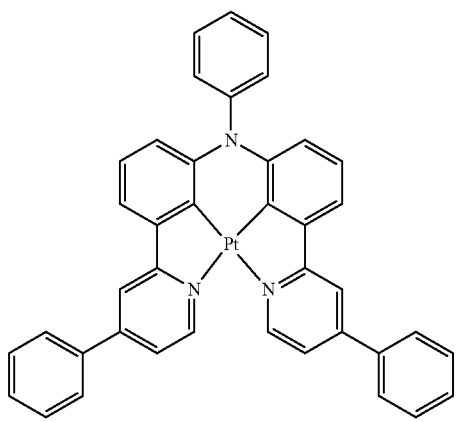
70
-continued
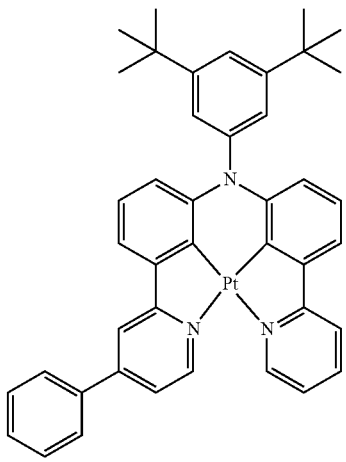
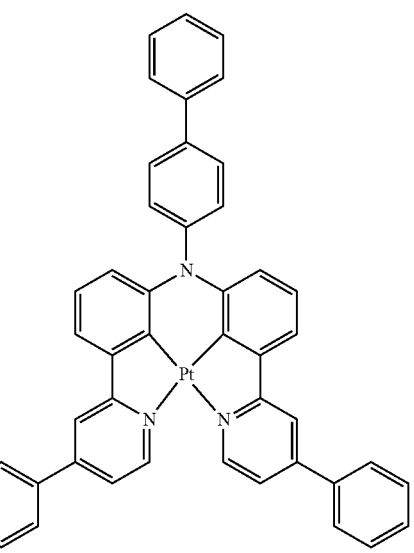
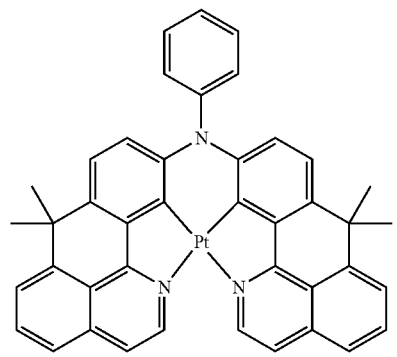

| 71 -continued | 72 -continued |
|---|---|
| 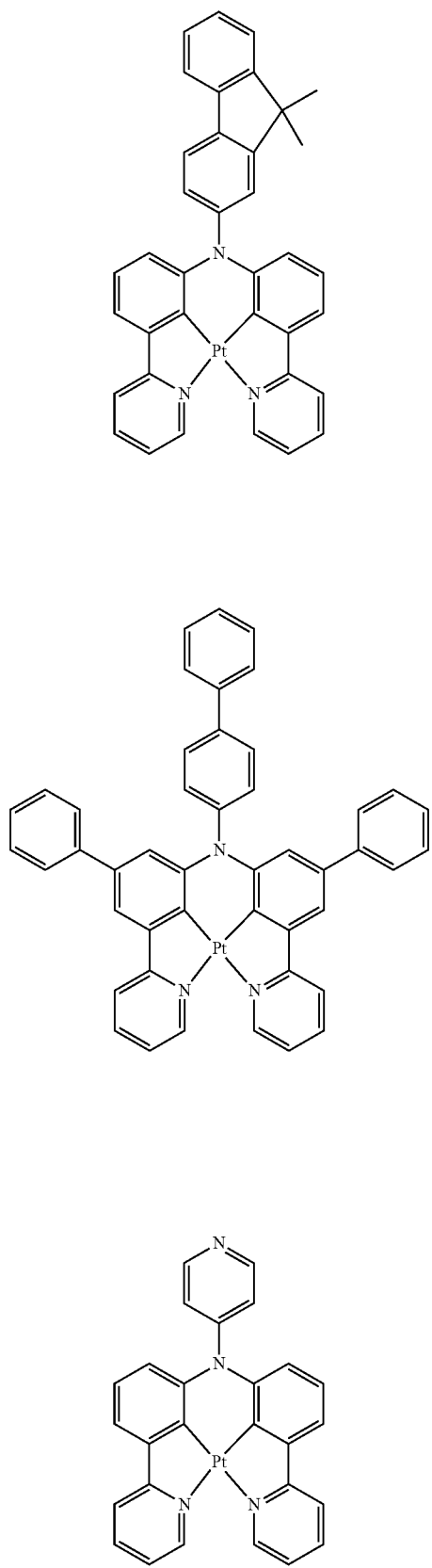 | 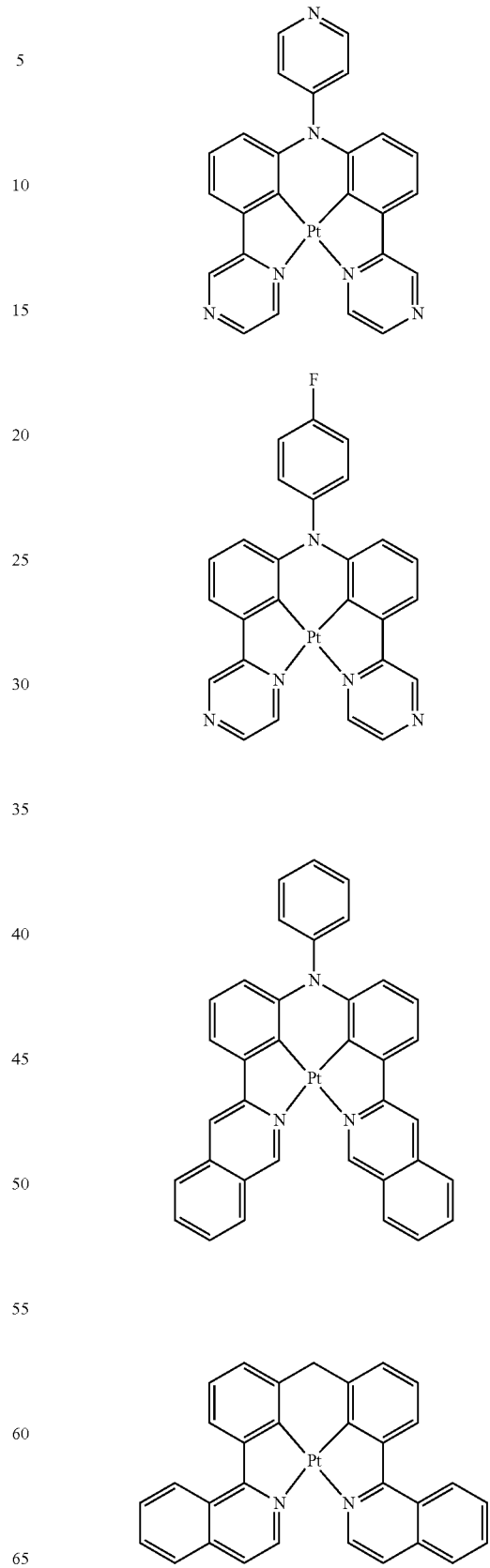 |

73
-continued
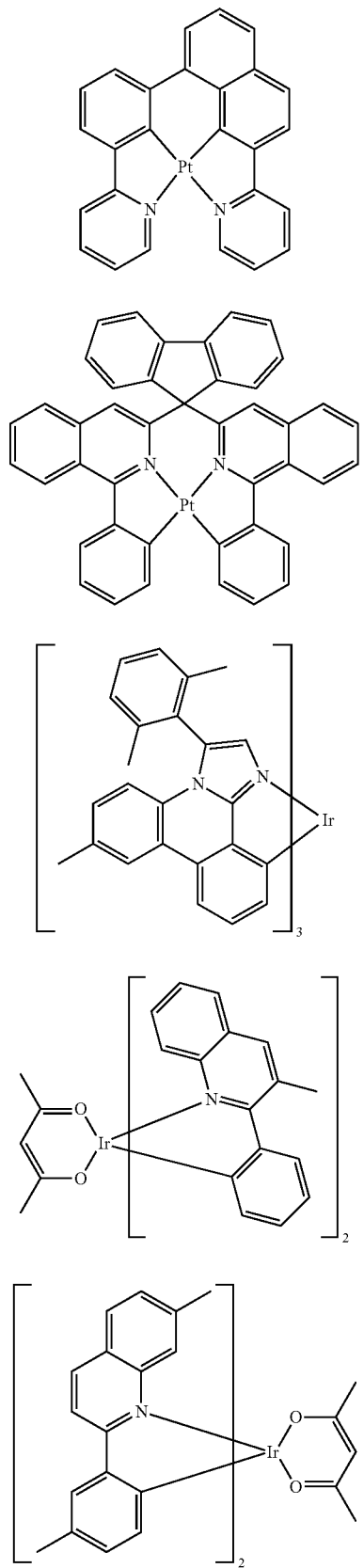
74
-continued
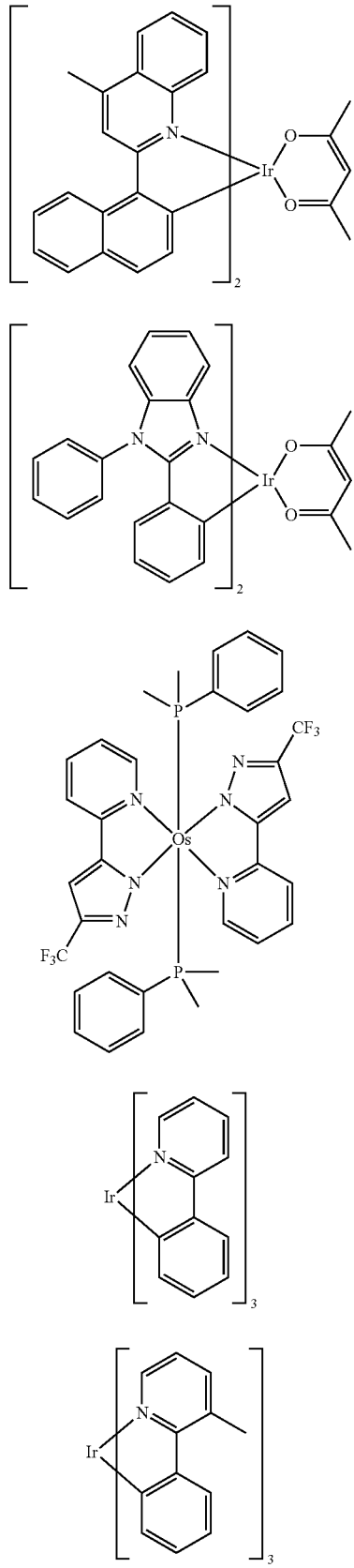

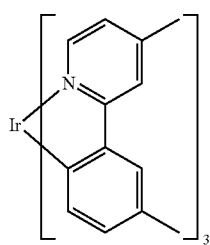
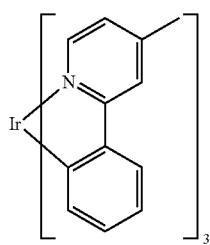
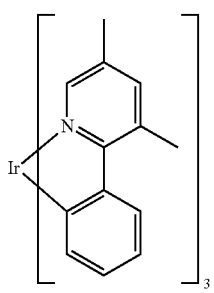
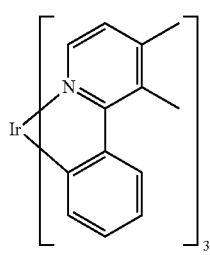
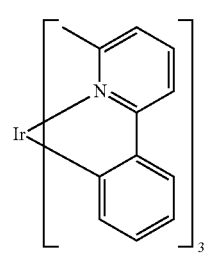
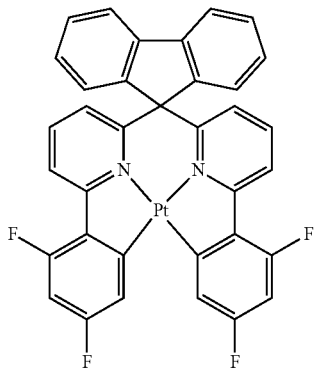
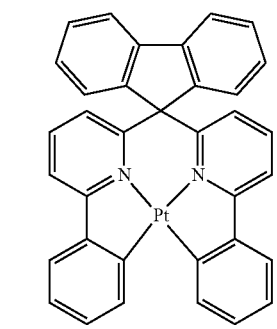
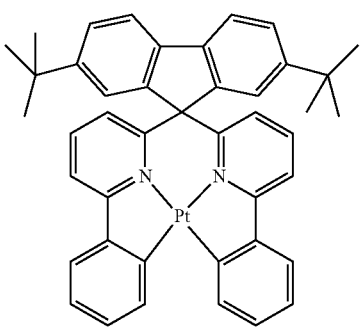
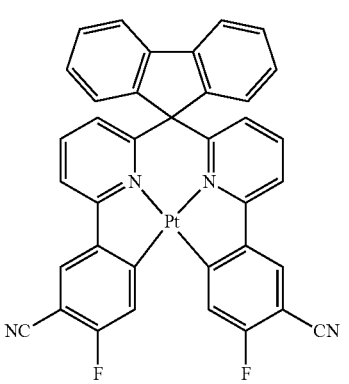

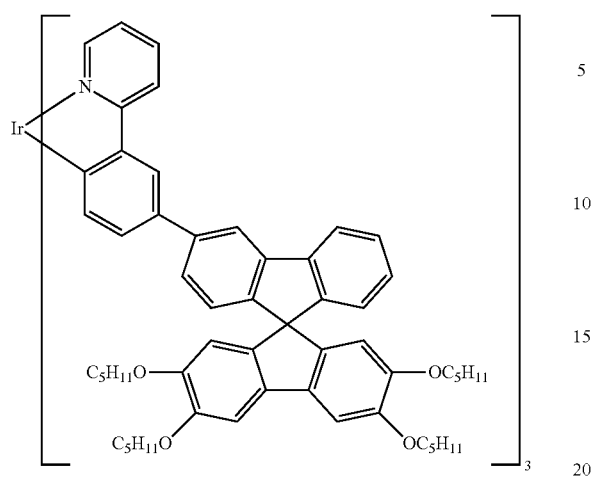
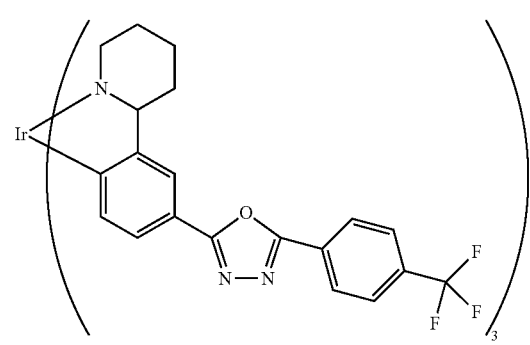
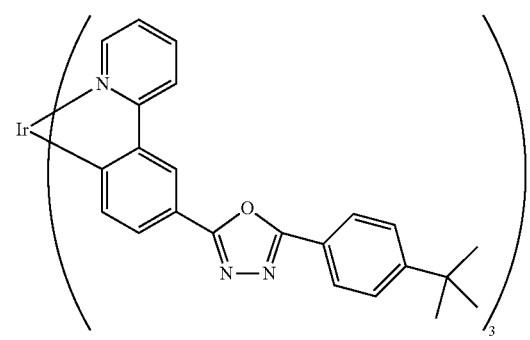
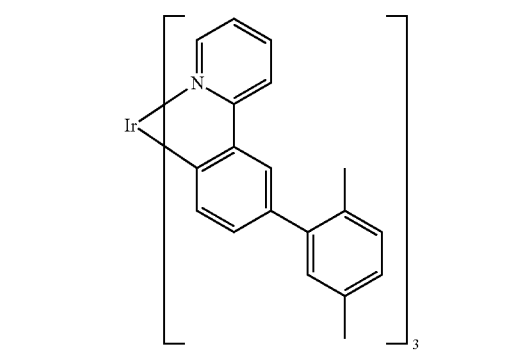
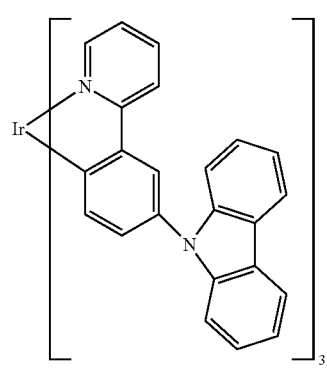
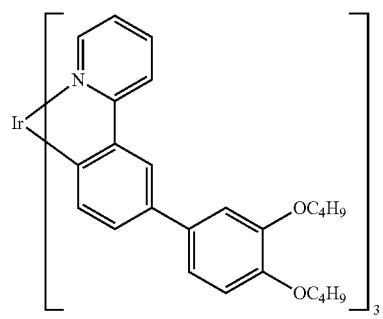
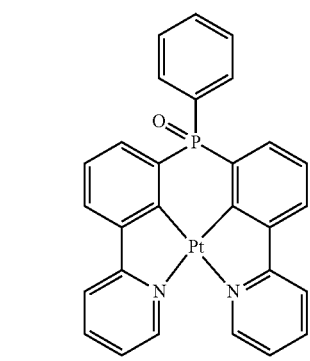
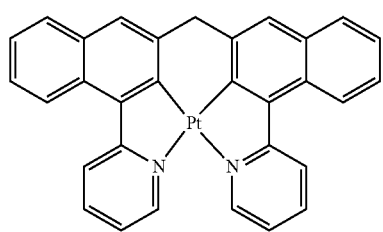

79
-continued
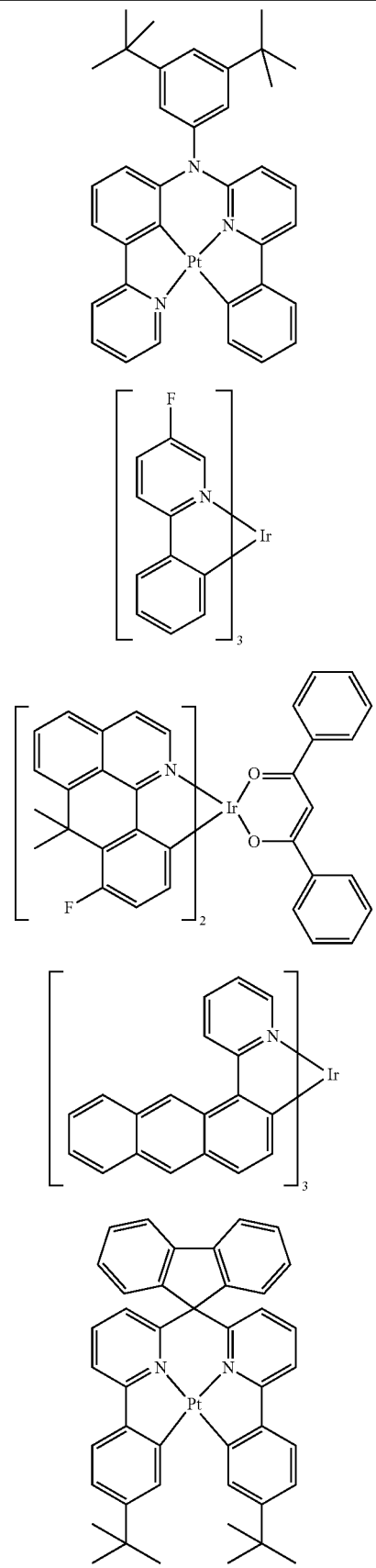
80
-continued
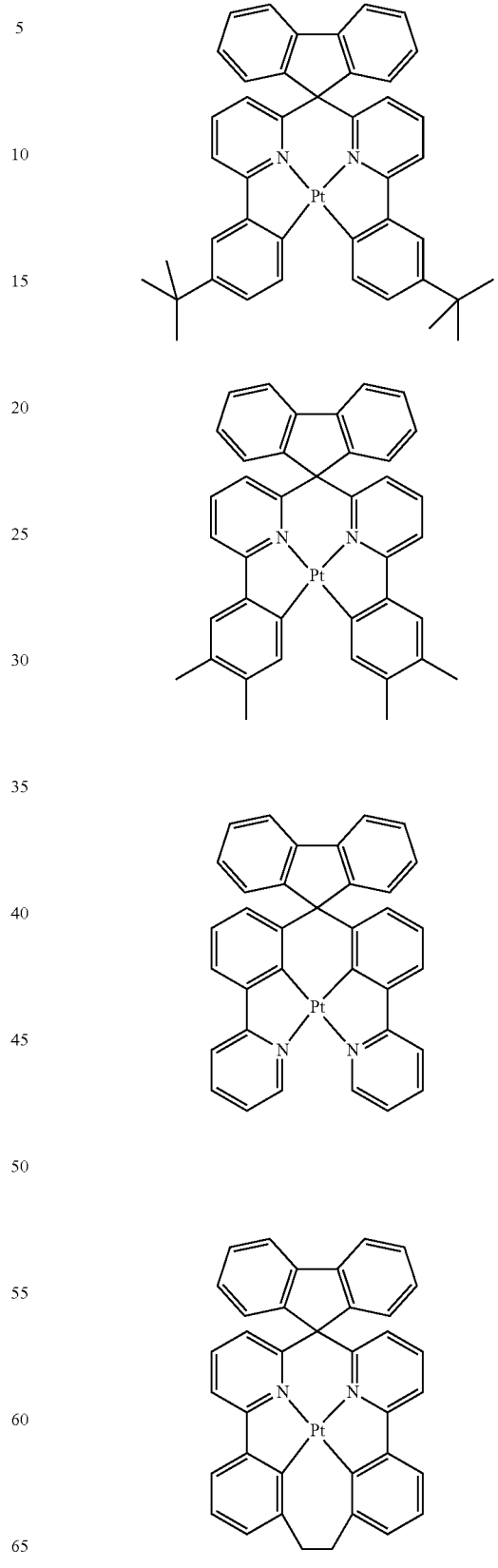

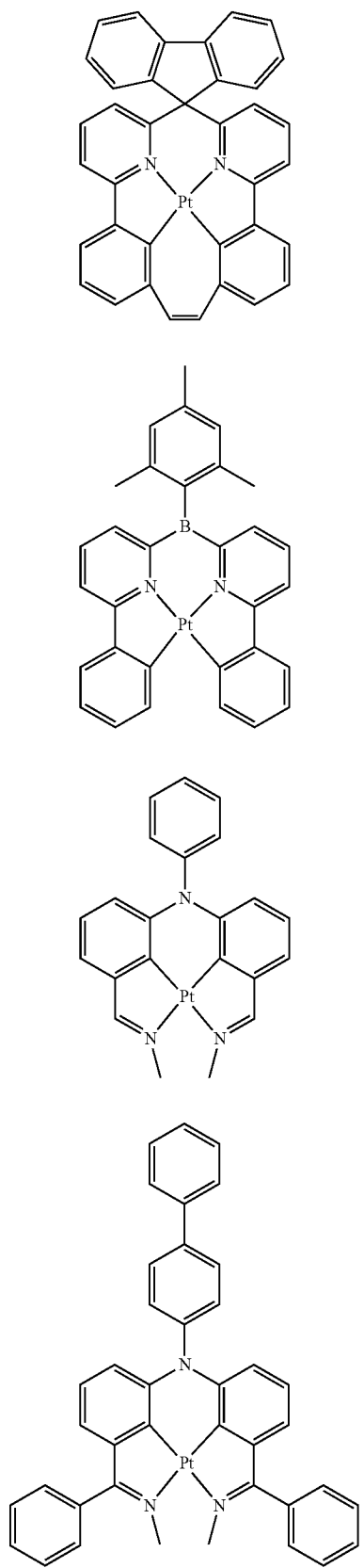
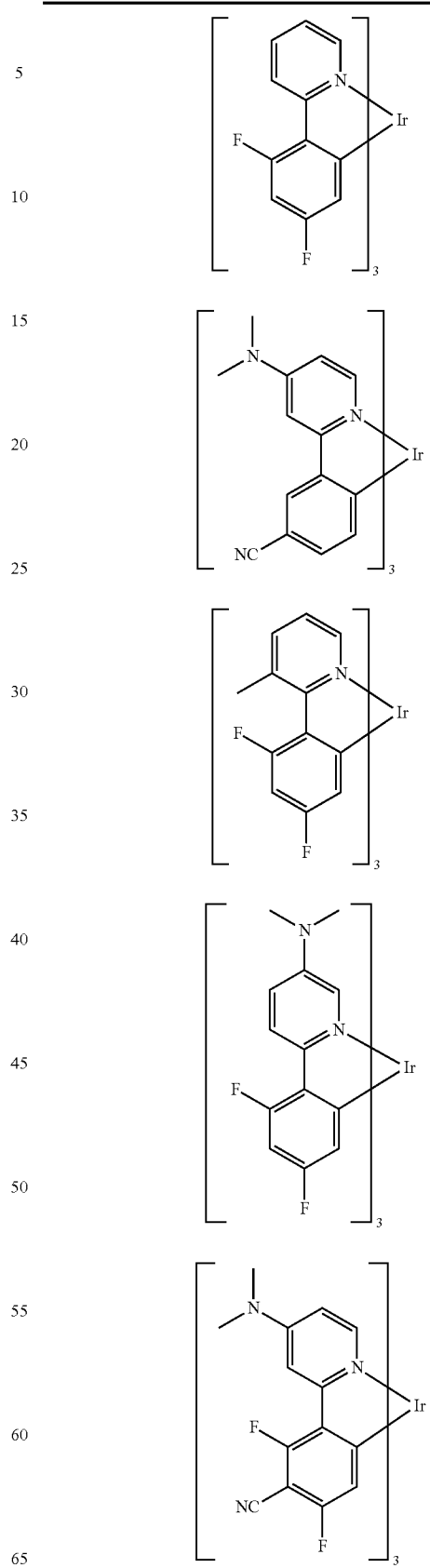

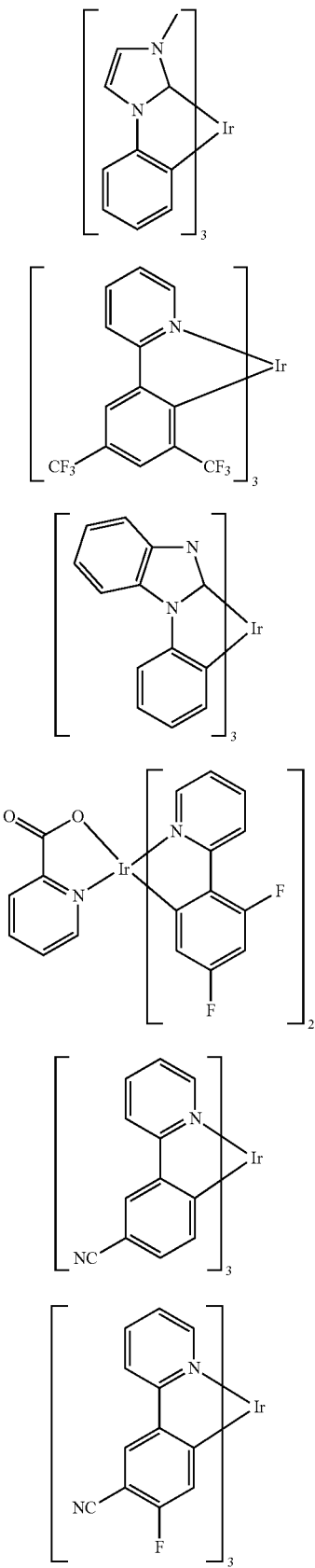
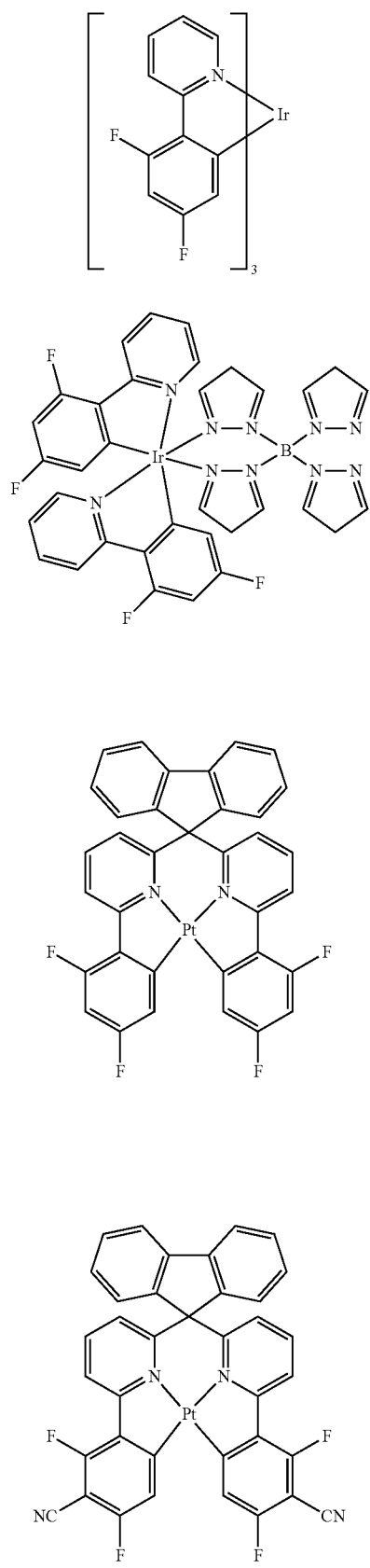

85
-continued
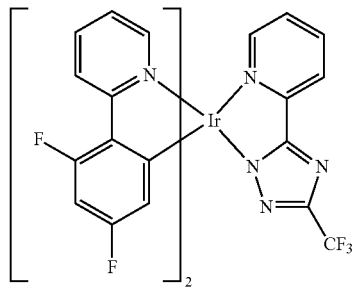
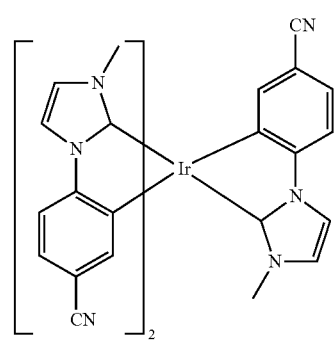
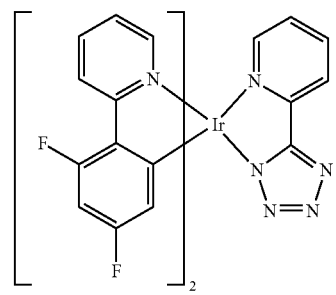
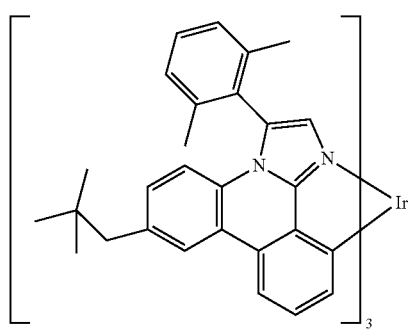
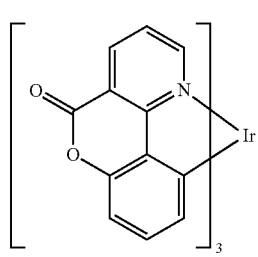
86
-continued
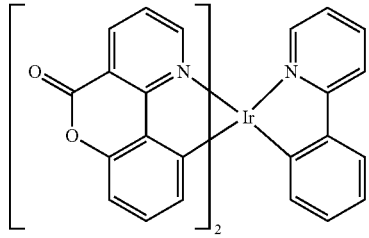
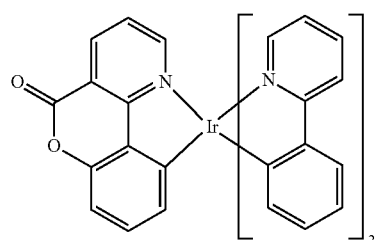
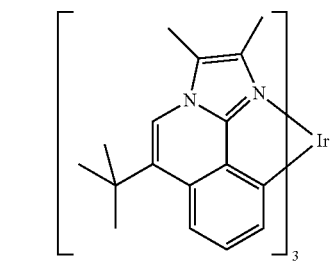
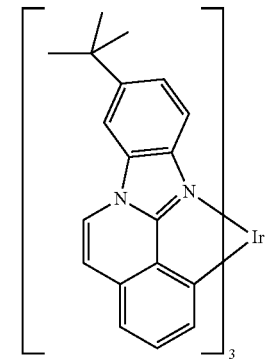
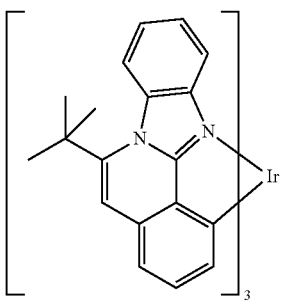

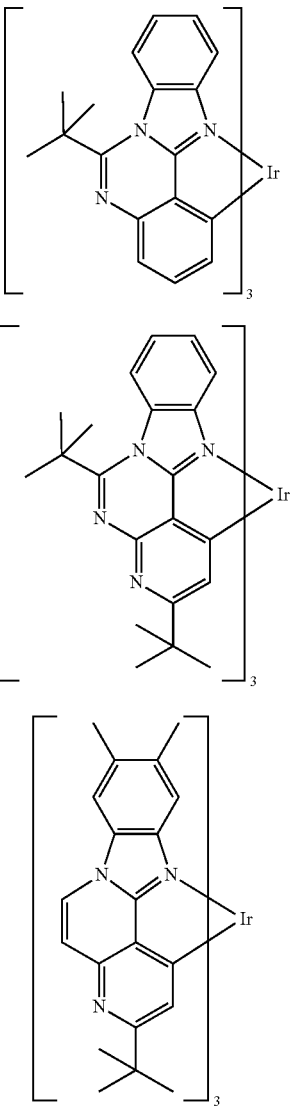

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are indenofluorenamines or indeno-fluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and the as yet unpublished EP 12004426.8. Preference is likewise given to the benzoindenofluorenamines disclosed in the as yet unpublished EP 12006239.3 and the benzofluorenamines disclosed in the as yet unpublished EP 13000012.8.

Suitable matrix materials, preferably for fluorescent dopants, besides the compounds of the formula (I) or (II), are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another. Preference is furthermore given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, and the pyrene compounds disclosed in EP 1749809, EP 1905754 and US 2012/0187826.

Preferred matrix materials for phosphorescent dopants, besides the compounds of the formula (I) or (II), are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

Suitable charge-transport materials, as can be used in the hole-injection or hole-transport layer or electron-blocking layer or in the electron-transport layer of the organic electroluminescent device according to the invention, besides the compounds of the formula (I) or (II), are, for example, the compounds disclosed in Y. Shirota et al., Chem. Rev, 2007, 107(4), 953-1010, or other materials as are employed in these layers in accordance with the prior art. Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Particularly preferred hole-transport materials are the compounds of the formula (I) or (II). Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or the as yet unpublished EP 12000929.5), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001).

The cathode of the electronic device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers. Furthermore, the anode may also consist of a plurality of layers, for example of an inner layer of ITO and an outer layer of a metal oxide, preferably tungsten oxide, molybdenum oxide or vanadium oxide.

During the production, the electronic device is appropriately (depending on the application) structured, provided with contacts and finally sealed, since the lifetime of the devices according to the invention is shortened in the presence of water and/or air.

In a preferred embodiment, the electronic device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) or (II) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The invention thus furthermore relates to a process for the production of the electronic device according to the invention, characterised in that at least one organic layer is applied by gas-phase deposition or from solution.

In accordance with the invention, the electronic devices comprising one or more compounds of the formula (I) can be employed in displays, as light sources in lighting applications and as light sources in medical and/or cosmetic applications (for example light therapy).

WORKING EXAMPLES

A) Synthesis Examples

The following syntheses are carried out, unless indicated otherwise, in dried solvents under a protective-gas atmosphere. The metal complexes are additionally handled with exclusion of light. The solvents and reagents can be purchased, for example, from Sigma-ALDRICH or ABCR. The numbers in square brackets for chemical compounds known from the literature relate to the CAS numbers.

Synthesis of Precursors

Example Int-1:
3-Dibenzofuran-4-yl-9-phenyl-9H-carbazole

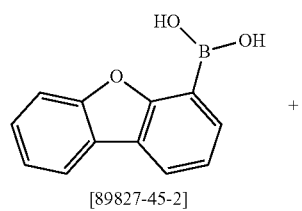

[89827-45-2]

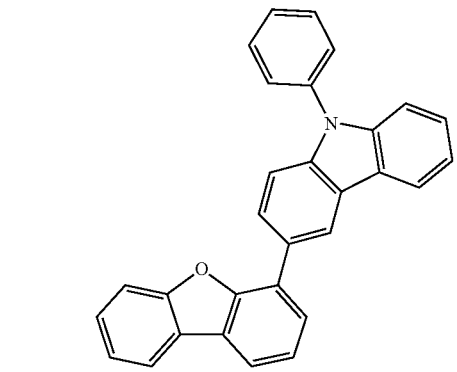

4335 g (204.1 mmol) of dibenzofuran-4-boronic acid, 60 g (186.2 mmol) of 3-bromo-9-phenyl-9H-carbazole, 118.4 ml (237 mmol) of $Na_2CO_3$ (2M solution) are suspended in 180 ml of toluene, 180 ml of ethanol and 150 ml of water. 3.9 g (3.3 mmol) of $Pd(PPh_3)_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 75.7 g (181 mmol), corresponding to 96% of theory.

The following compounds can be obtained analogously:

| | Starting material 1 | Starting material 2 | Product | Yield |
|---|---|---|---|---|
| Int-1a | [89827-45-2] | [36809-26-4] | | 90% |

-continued
| | Starting material 1 | Starting material 2 | Product | Yield |
|---|---|---|---|---|
| Int-1b | 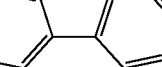 [89827-45-2] | 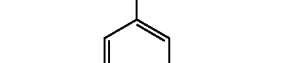 [499126-71-1] | 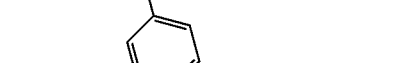 | 92% |
| Int-1c |  [89827-45-2] | 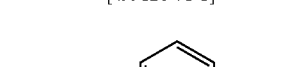 [57102-42-8] | 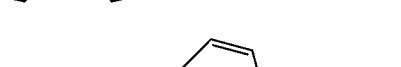 | 89% |
| Int-1d |  [89827-45-2] |  [63524-03-8] | 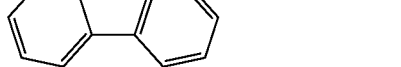 | 92% |
| Int-1e |  [89827-45-2] | 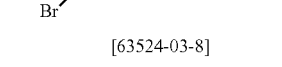 [94994-62-4] | 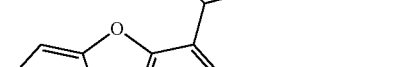 | 86% |

| Starting material 1 | Starting material 2 | Product | Yield |
|---|---|---|---|
| Int-1f [89827-45-2] | 1246562-40-2 | | 96% |
| Int-1g [89827-45-2] | [313050-71-4] | | 90% |

Example Int-2:
Bisbiphenyl-4-yldibenzofuran-4-ylamine

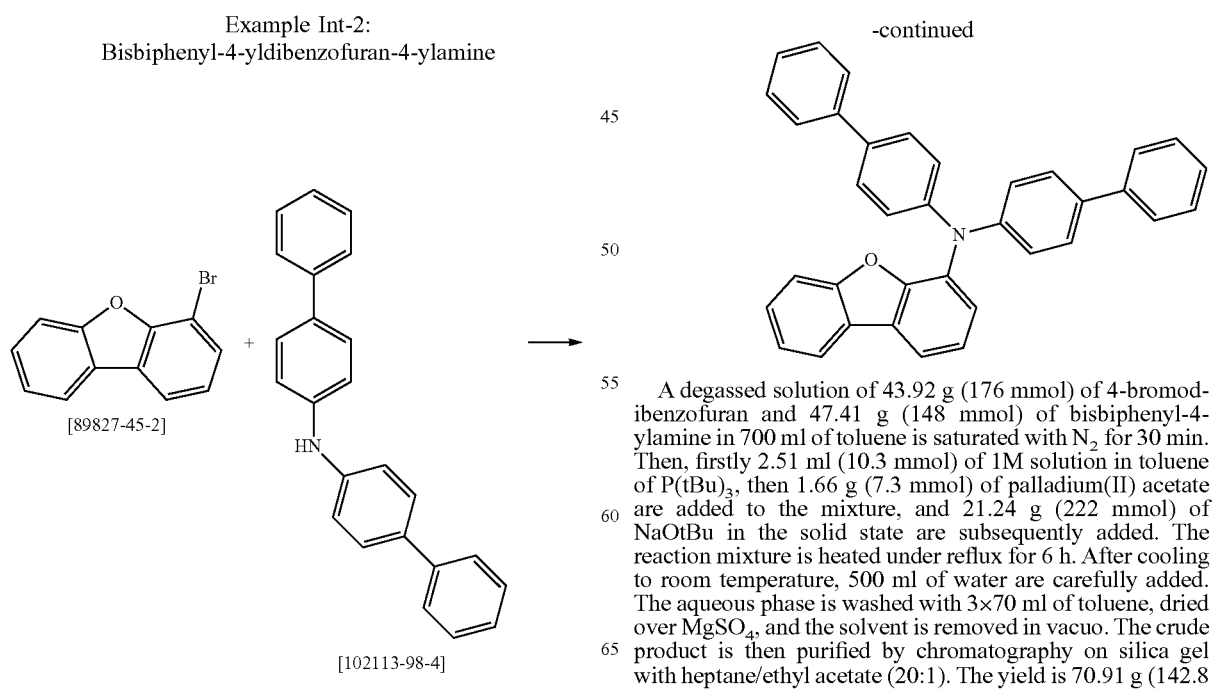

A degassed solution of 43.92 g (176 mmol) of 4-bromodibenzofuran and 47.41 g (148 mmol) of bisbiphenyl-4-ylamine in 700 ml of toluene is saturated with $N_2$ for 30 min. Then, firstly 2.51 ml (10.3 mmol) of 1M solution in toluene of $P(tBu)_3$, then 1.66 g (7.3 mmol) of palladium(II) acetate are added to the mixture, and 21.24 g (222 mmol) of NaOtBu in the solid state are subsequently added. The reaction mixture is heated under reflux for 6 h. After cooling to room temperature, 500 ml of water are carefully added. The aqueous phase is washed with 3×70 ml of toluene, dried over $MgSO_4$, and the solvent is removed in vacuo. The crude product is then purified by chromatography on silica gel with heptane/ethyl acetate (20:1). The yield is 70.91 g (142.8 mmol), corresponding to 94% of theory.

The following compounds can be obtained analogously:
| | Starting material 1 | Starting material 2 | Product | Yield |
|---|---|---|---|---|
| Int-2a | 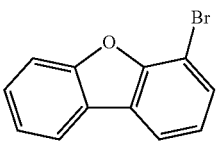 [89827-45-2] | 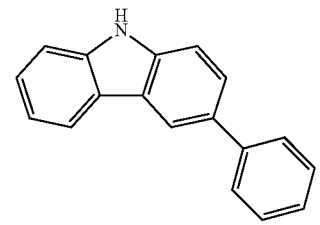 | 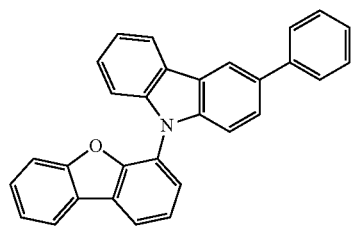 [SMILES: c1ccc(-c2ccc3c(c2)c2ccccc2n3-c2cccc3c2oc2ccccc23)cc1] [103012-26-6] | 90% |
| Int-2b | 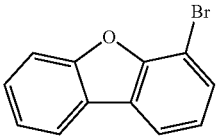 [89827-45-2] | 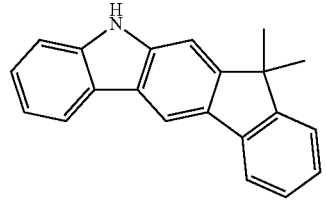 [1257220-47-5] | 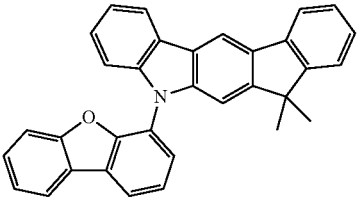 [SMILES: CC1(C)c2ccccc2-c2cc3c4ccccc4n(-c4cccc5c4oc4ccccc45)c3cc21] | 87% |
| Int-2c | 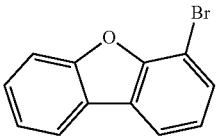 [89827-45-2] | 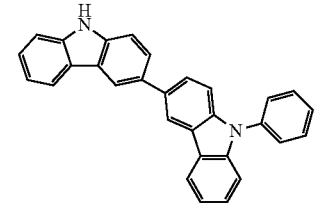 [1050735-14-9] | 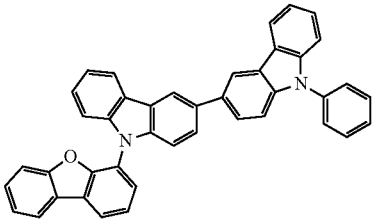 [SMILES: c1ccc(-n2c3ccccc3c3cc(-c4ccc5c(c4)c4ccccc4n5-c4cccc5c4oc4ccccc45)ccc32)cc1] | 83% |
| Int-2d | 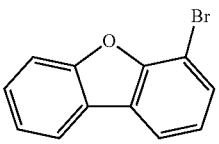 [89827-45-2] | 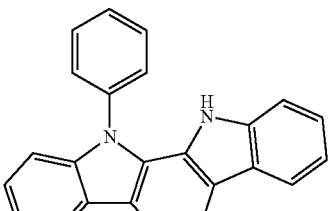 [1024598-06-8] | 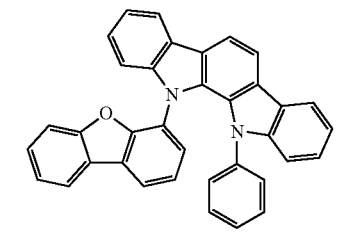 [SMILES: c1ccc(-n2c3ccccc3c3ccc4c5ccccc5n(-c5cccc6c5oc5ccccc56)c4c32)cc1] | 57% |

-continued
| Starting material 1 | Starting material 2 | Product | Yield |
|---|---|---|---|
| Int-2e 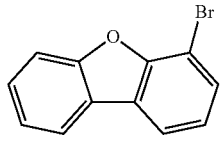 [89827-45-2] | 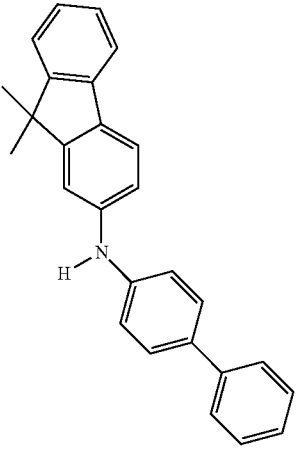 [1386375-27-4] | 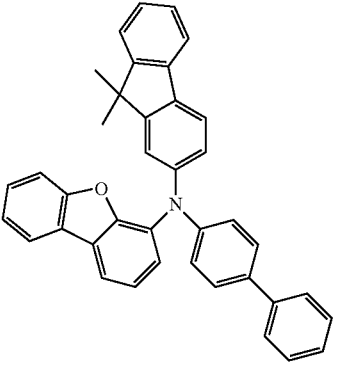 [SMILES: CC1(C)c2ccccc2-c2ccc(N(c3ccc(-c4ccccc4)cc3)c3cccc4c3oc3ccccc34)cc21] | 86% |
| Int-2f 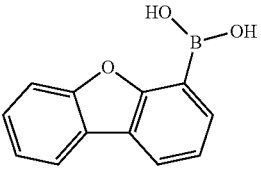 [89827-45-2] | 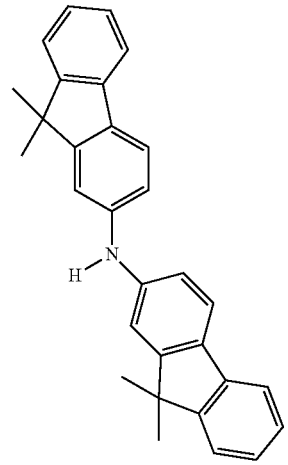 [1386375-16-1] | 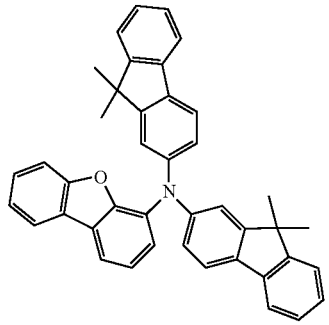 [SMILES: CC1(C)c2ccccc2-c2ccc(N(c3ccc4c(c3)C(C)(C)c3ccccc3-4)c3cccc4c3oc3ccccc34)cc21] | 85% |
Example Int-3: 9-Phenyl-3-(6-trimethylsilanyldibenzofuran-4-yl)-9H-carbazole
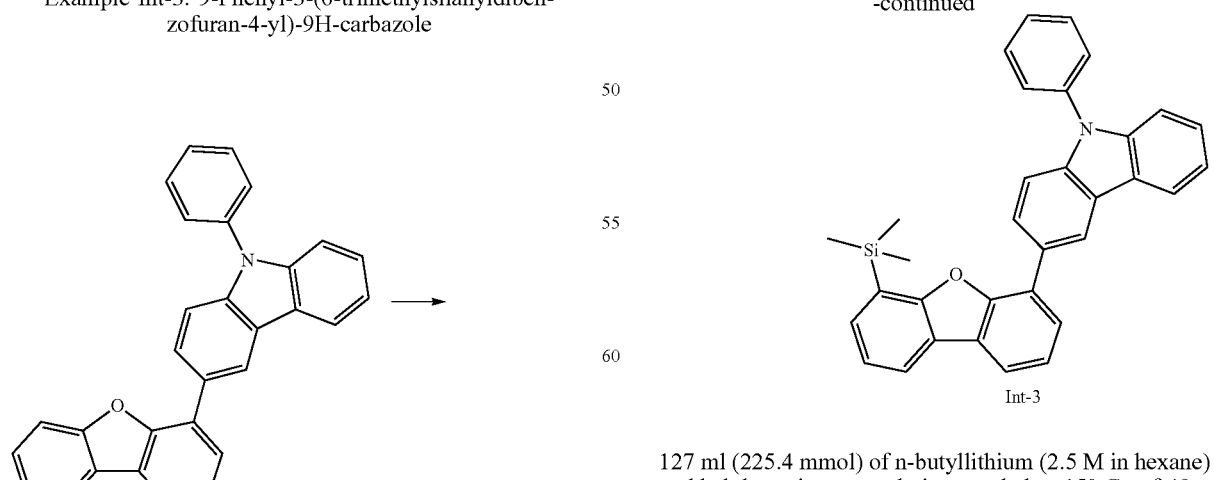
Int-3
127 ml (225.4 mmol) of n-butyllithium (2.5 M in hexane) are added dropwise to a solution, cooled to 15° C., of 49 g (121 mmol) of 3-dibenzofuran-4-yl-9-phenyl-9H-carbazole and 28 g (242 mmol) of TMEDA in 1000 ml of THF. The reaction mixture is stirred at room temperature for 3 h, then cooled to 0° C., and 26 g (242 mmol) of chlorotrimethylsilane are added dropwise over the course of 30 min., and the mixture is stirred at room temperature for 16 h. The solvent is subsequently removed in vacuo, and the residue is purified by chromatography on silica gel with toluene:dichloromethane 2:1. Yield: 34 g (72 mmol), 60% of theory.

The following compounds can be obtained analogously:

| | Starting material 1 | Product | Yield |
|---|---|---|---|
| Int-3a | | | 81% |
| Int-3b | | | 88% |
| Int-3c | | | 84% |

-continued

| Starting material 1 | Product | Yield |
|---|---|---|
| Int-3d | | 88% |
| Int-3e | | 70% |
| Int-3f | | 86% |
| Int-3g | | 79% |

-continued

| Starting material 1 | Product | Yield |
|---|---|---|
| Int-3h | | 75% |
| Int-3i | | 72% |
| Int-3j | | 81% |
| Int-3k | | 83% |
| Int-3l | | 88% |

| Starting material 1 | Product | Yield |
|---|---|---|
| Int-3m | | 84% |

Example Int-4: B-[6-(Phenyl-9H-carbazol-3-yl)-4-dibenzofuranyl]boronic acid

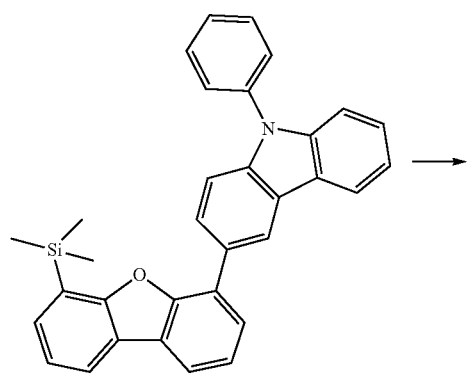

→

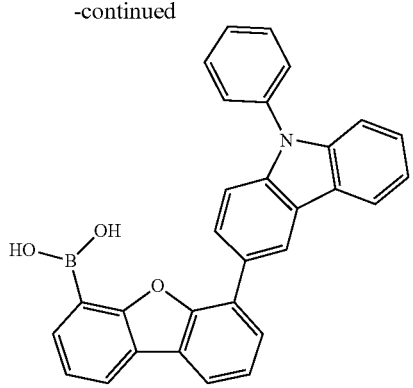

Under protective gas, 21 g (86 mmol) of bromine tribromide are added dropwise to a solution of 34 g (72 mmol) of B-[6-(phenyl-9H-carbazol-3-yl)-4-dibenzofuranyl]boronic acid in 500 ml of dichloromethane, and the mixture is stirred at room temperature for 10 h. A little water is then slowly added to the mixture, and the precipitated residue is filtered off and washed with heptane. The yield is 28 g (62 mmol), corresponding to 86% of theory.

The following compounds can be obtained analogously:

| Starting material 1 | Product | Yield |
|---|---|---|
| Int-4a | | 82% |

-continued

| Starting material 1 | Product | Yield |
|---|---|---|
| Int-4b | | 81% |
| Int-4c | | 87% |
| Int-4d | | 86% |
| Int-4e | | 79% |

-continued

| | Starting material 1 | Product | Yield |
|---|---|---|---|
| Int-4f | | | 78% |
| Int-4g | | | 83% |
| Int-4h | | | 85% |
| Int-4i | | | 78% |
| Int-4j | | | 84% |

-continued
| Starting material 1 | | Product | Yield |
|---|---|---|---|
| Int-4k | (structure) | (structure) | 87% |
| Int-4l | (structure) | (structure) | 80% |
| Int-4m | (structure) | (structure) | 86% |
Example Int-5: B-[6-(Phenyl-9H-carbazol-3-yl)-4-dibenzofuranyl]boronic acid
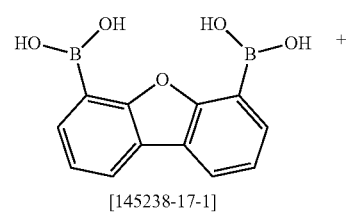
[145238-17-1]
-continued
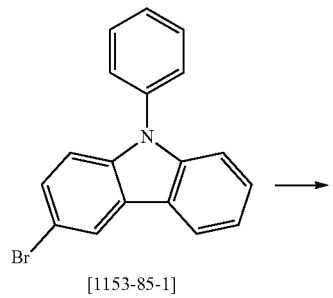
[1153-85-1]

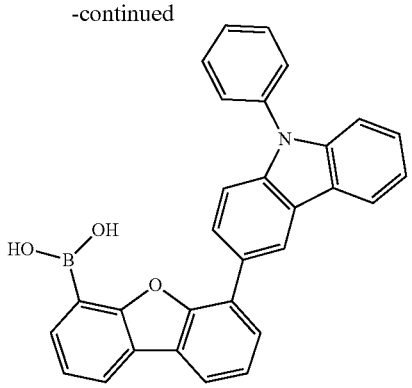

9 g (32 mmol) of B,B'-4,6-dibenzofurandiylbisboronic acid, 15 g (31.6 mmol) of 3-bromo-9-phenyl-9H-carbazole, 31 ml (63 mmol) of Na$_2$CO$_3$ (2M solution) are suspended in 120 ml of toluene and 120 ml of ethanol. 0.73 g (0.63 mmol) of Pd(PPh$_3$)$_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 11.1 g (24 mmol), corresponding to 70% of theory.

The following compounds can be obtained analogously:

| | Starting material 1 | Starting material 2 |
|---|---|---|
| Int-5b | [480438-76-4] | [1153-85-1] |
| Int-5c | [862159-27-1] | [1257220-44-2] |

| | Product | Yield |
|---|---|---|
| Int-5b | | 69% |

| Int-5c | 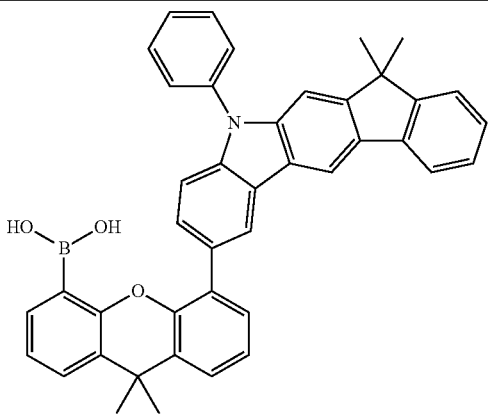 | 74% |

Synthesis of Compounds According to the Invention

Example 6: Biphenyl-4-yl-(9,9-dimethyl-9H-fluoren-2-yl)-{4-[6-(9-phenyl-9H-carbazol-3-yl)dibenzofuran-4-yl]phenyl}amine

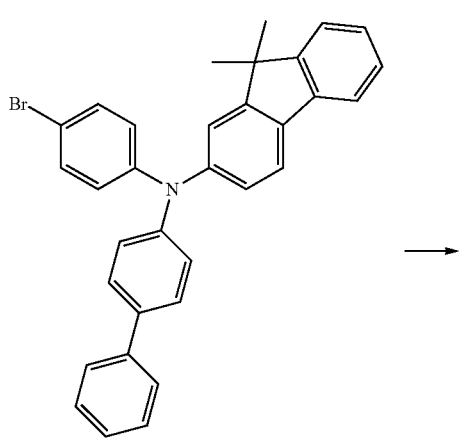

+

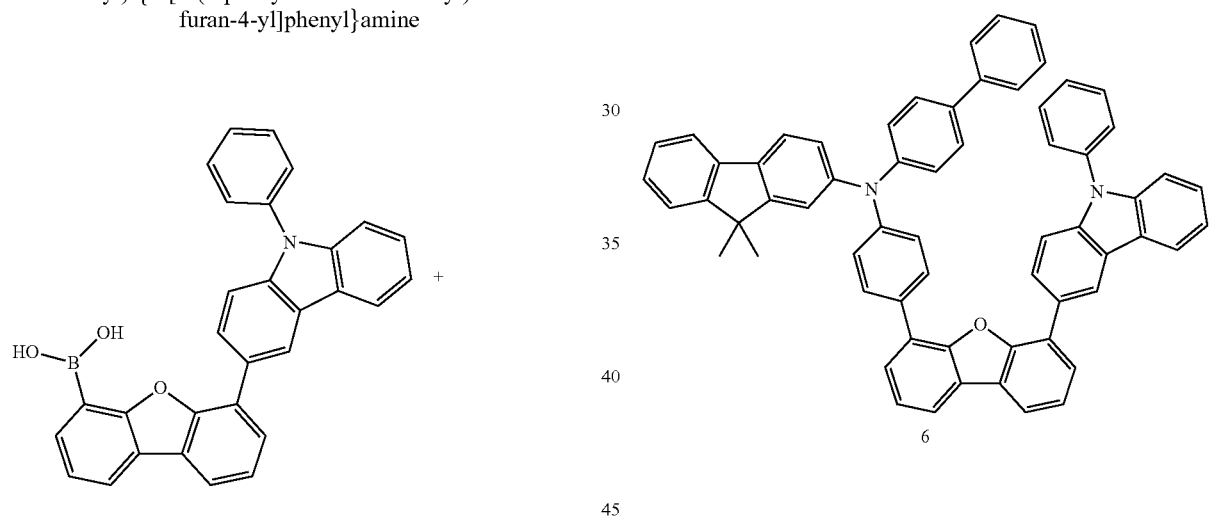

6

32.1 g (70 mmol) of B-[6-(phenyl-9H-carbazol-3-yl)-4-dibenzofuranyl]boronic acid, 36.12 g (70 mmol) of biphenyl-4-yl-(4-bromophenyl)-(9,9-dimethyl-9H-fluoren-2-yl)amine, and 78.9 ml (158 mmol) of $Na_2CO_3$ (2M solution) are suspended in 120 ml of ethanol and 100 ml of water. 1.3 g (1.1 mmol) of $Pd(PPh_3)_4$ are added to this suspension, and the reaction mixture is heated under reflux for 16 h. After cooling, dichloromethane is added to the mixture, the organic phase is separated off and filtered through silica gel. The yield is 40 g (47 mmol), corresponding to 67.8% of theory. The residue is recrystallised from toluene and finally sublimed in a high vacuum (p=$5\times10^{-6}$ mbar). The purity is 99.9%.

The following compounds can be obtained analogously:
| | Starting material 1 | Starting material 2 |
|---|---|---|
| 6a | 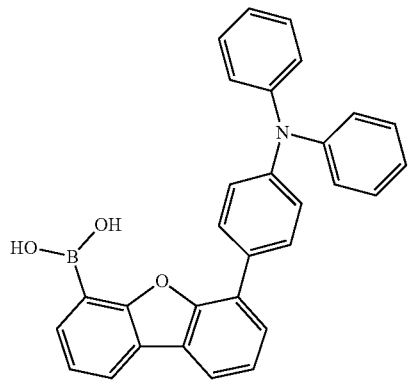 [SMILES: OB(O)c1cccc2c1oc1c(-c3ccc(N(c4ccccc4)c4ccccc4)cc3)cccc12] | 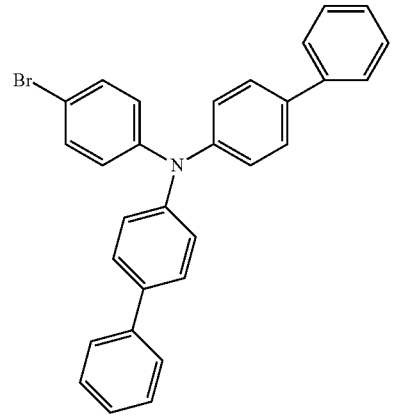 [499128-71-1] |
| 6b | 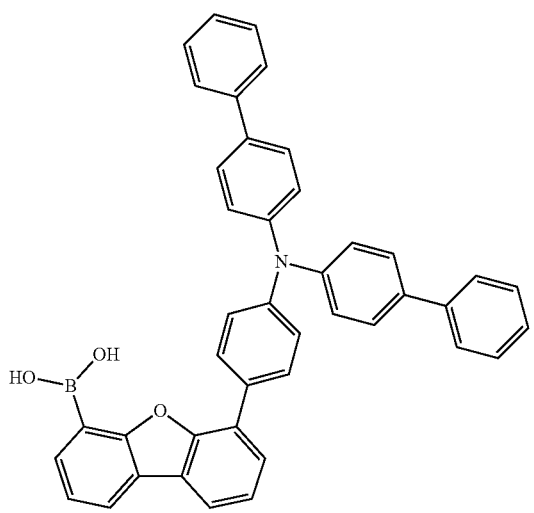 [SMILES: OB(O)c1cccc2c1oc1c(-c3ccc(N(c4ccc(-c5ccccc5)cc4)c4ccc(-c5ccccc5)cc4)cc3)cccc12] | 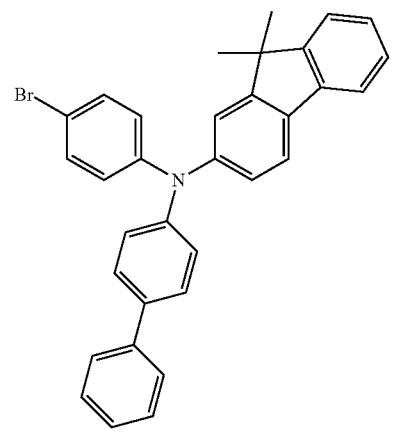 [1246562-40-2] |
| 6c | 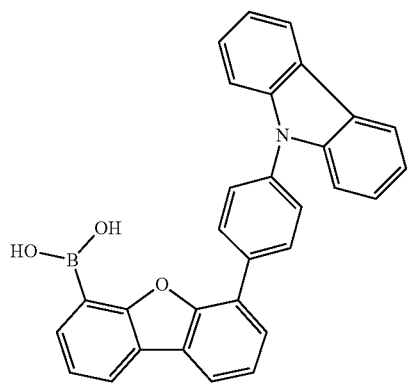 [SMILES: OB(O)c1cccc2c1oc1c(-c3ccc(-n4c5ccccc5c5ccccc54)cc3)cccc12] | 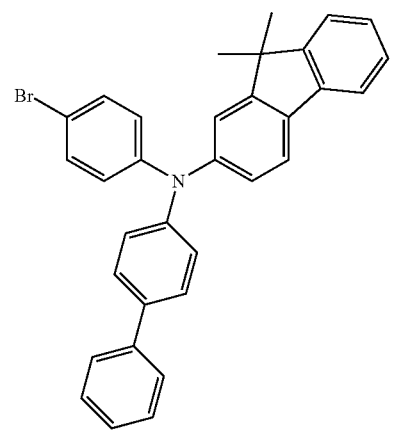 [1246562-40-2] |

-continued
| | | |
|---|---|---|
| 6d | 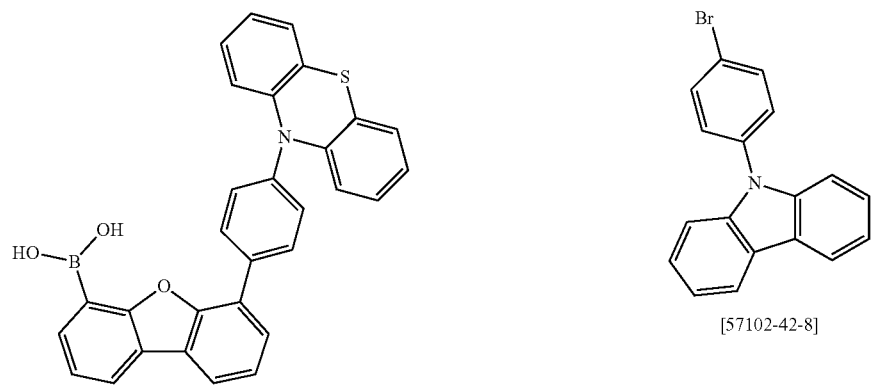 | [57102-42-8] |
| 6e | 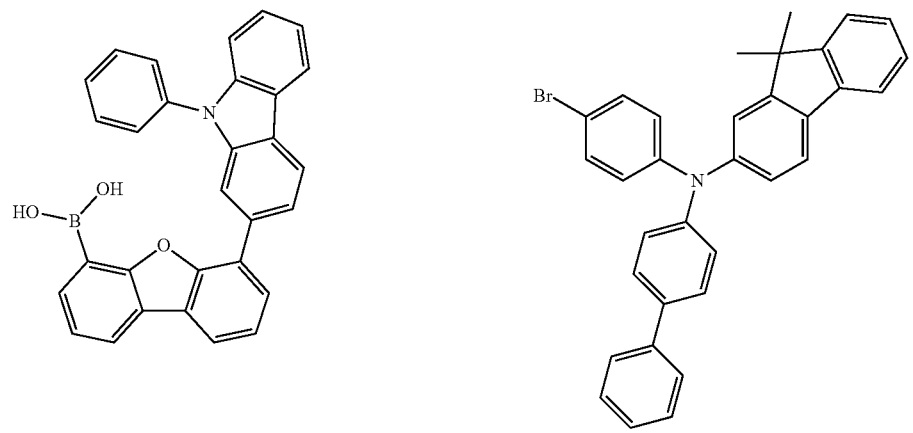 | [1246562-40-2] |
| 6f | 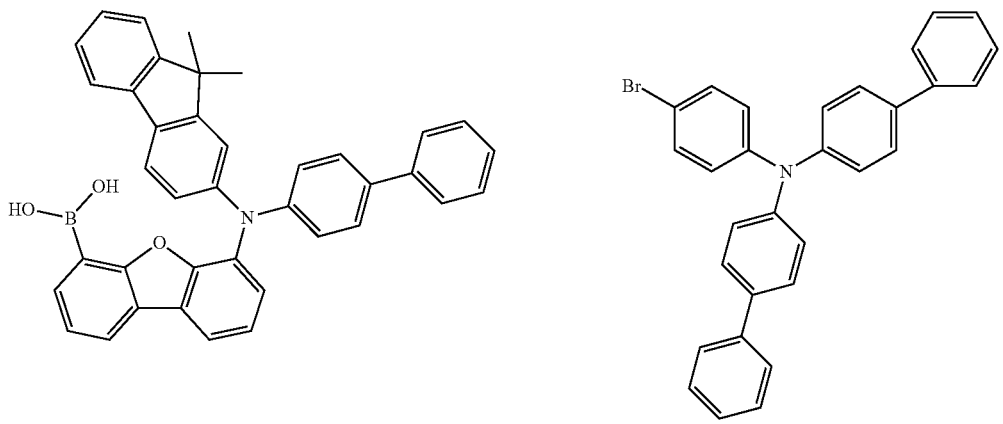 | [499128-71-1] |

-continued
6g
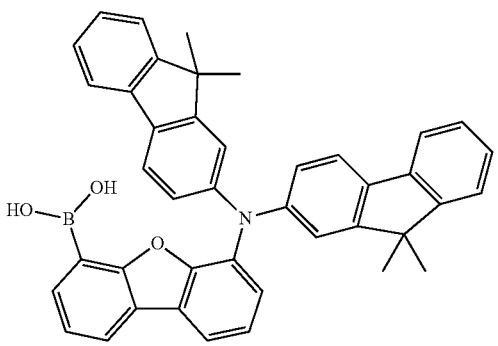 [SMILES: CC1(C)c2ccccc2-c2ccc(N(c3ccc4c(c3)C(C)(C)c3ccccc3-4)c3cccc4c3oc3c(B(O)O)cccc34)cc21]
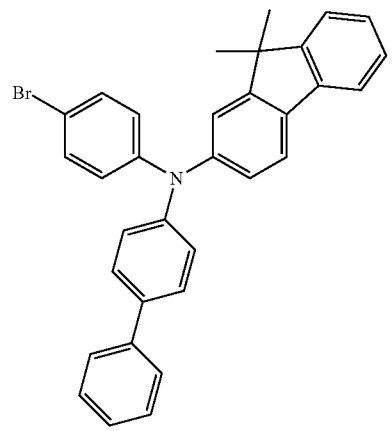
[1246562-40-2]
6h
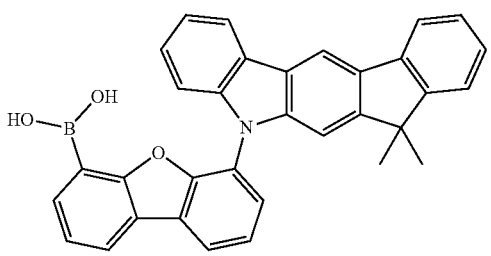 [SMILES: CC1(C)c2ccccc2-c2cc3c4ccccc4n(-c4cccc5c4oc4c(B(O)O)cccc45)c3cc21]
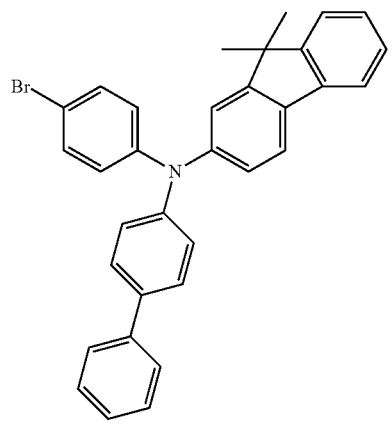
[1246562-40-2]
6i
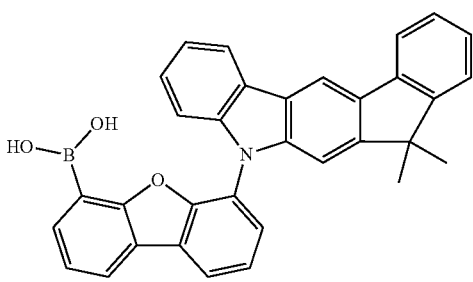 [SMILES: CC1(C)c2ccccc2-c2cc3c4ccccc4n(-c4cccc5c4oc4c(B(O)O)cccc45)c3cc21]
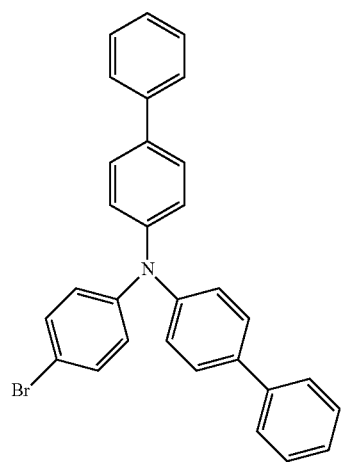
[499128-71-1]

-continued
6j
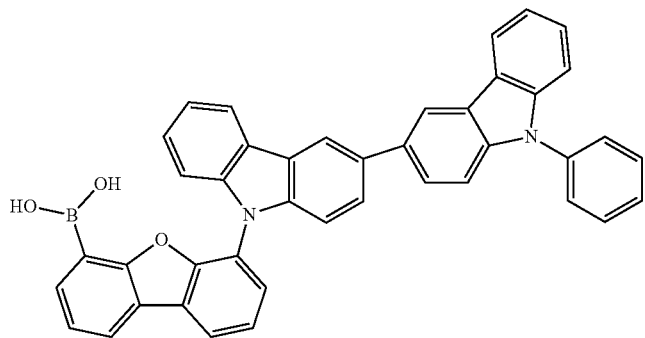 [SMILES: OB(O)c1cccc2c1oc1c(-n3c4ccccc4c4cc(-c5ccc6c(c5)c5ccccc5n6-c5ccccc5)ccc43)cccc12]
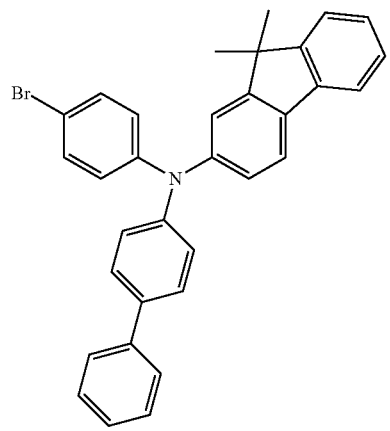
[1246562-40-2]
6k
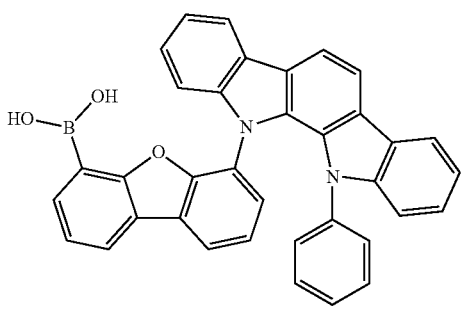 [SMILES: OB(O)c1cccc2c1oc1c(-n3c4ccccc4c4ccc5c6ccccc6n(-c6ccccc6)c5c43)cccc12]
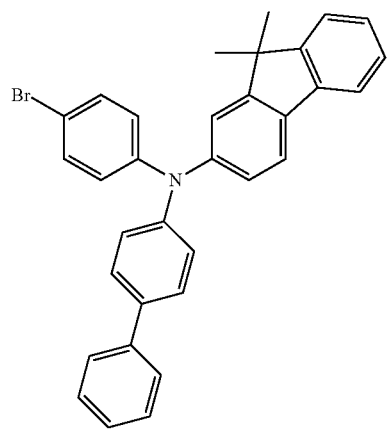
[1246562-40-2]
6l
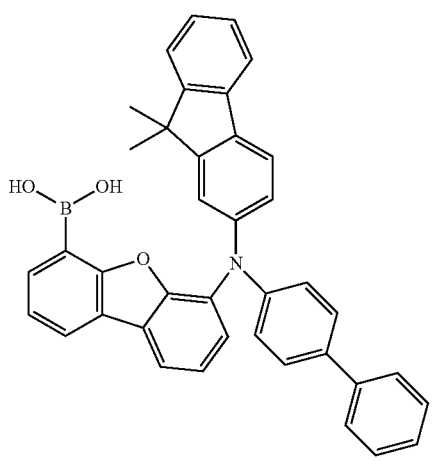 [SMILES: CC1(C)c2ccccc2-c2ccc(N(c3ccc(-c4ccccc4)cc3)c3cccc4c3oc3c(B(O)O)cccc34)cc21]
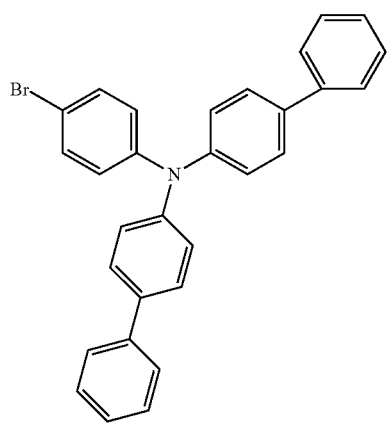
[499128-71-1]

6n
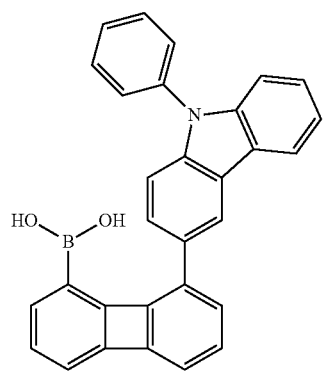 [SMILES: OB(O)c1cccc2c1-c1c(-c3ccc4c(c3)c3ccccc3n4-c3ccccc3)cccc1-2] 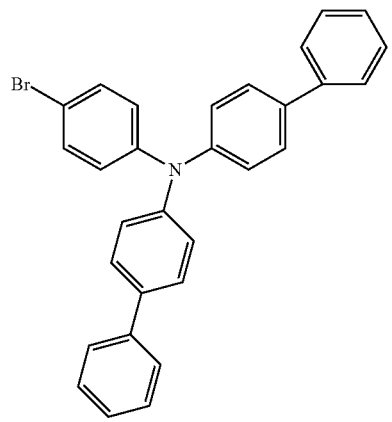
[499128-71-1]
6o
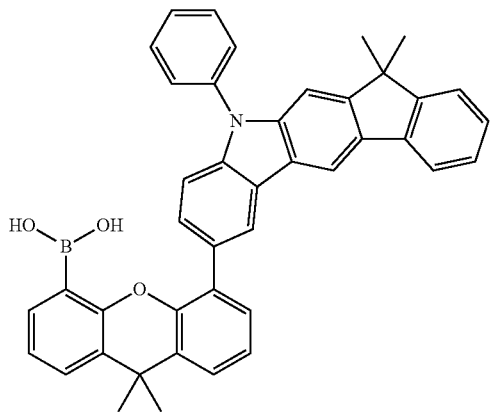 [SMILES: CC1(C)c2ccccc2-c2cc3c4cc(-c5cccc6c5Oc5c(B(O)O)cccc5C6(C)C)ccc4n(-c4ccccc4)c3cc21] 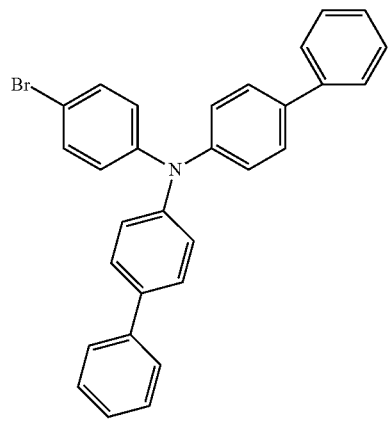
[499128-71-1]
6p
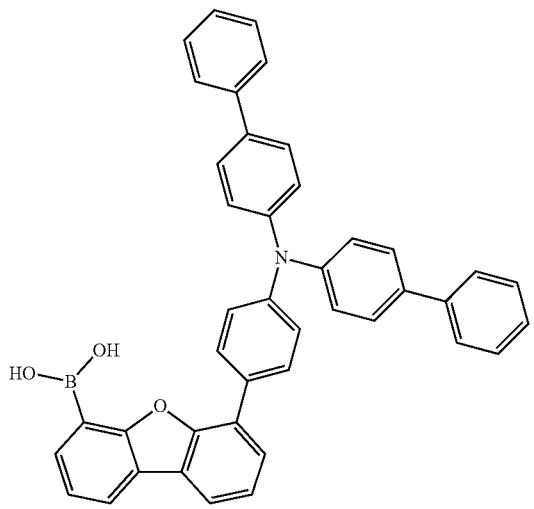 [SMILES: OB(O)c1cccc2c1oc1c(-c3ccc(N(c4ccc(-c5ccccc5)cc4)c4ccc(-c5ccccc5)cc4)cc3)cccc12] 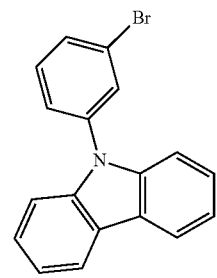
[185112-61-2]

| | | |
|---|---|---|
| 6r | 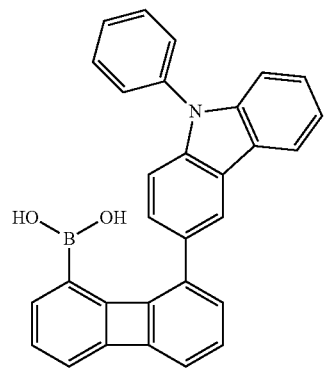 [SMILES: OB(O)c1cccc2c1-c1c(-c3ccc4c(c3)c3ccccc3n4-c3ccccc3)cccc1-2] | 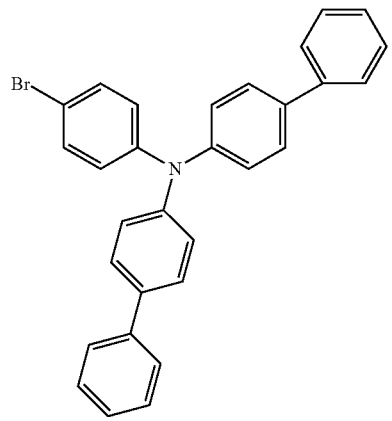<br>[499128-71-1] |
| 6s | 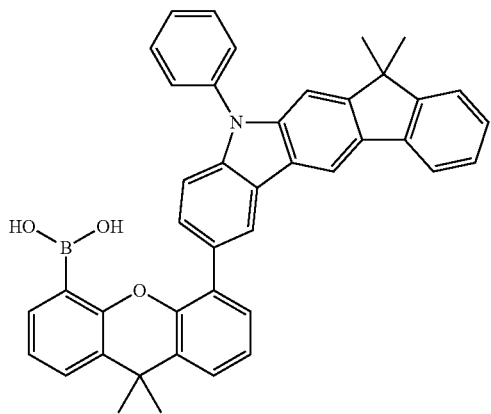 [SMILES: CC1(C)c2ccccc2-c2cc3c4cc(-c5cccc6c5Oc5c(B(O)O)cccc5C6(C)C)ccc4n(-c4ccccc4)c3cc21] | 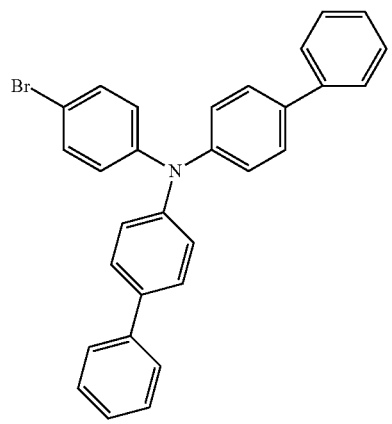<br>[499128-71-1] |
| 6t | 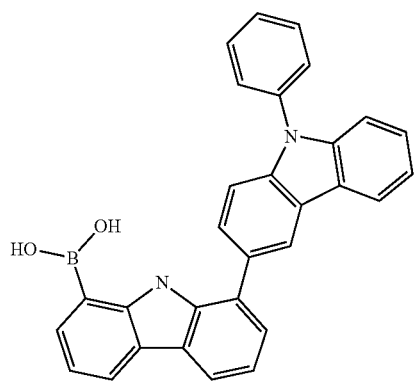 [SMILES: OB(O)c1cccc2c1[nH]c1c(-c3ccc4c(c3)c3ccccc3n4-c3ccccc3)cccc12] | 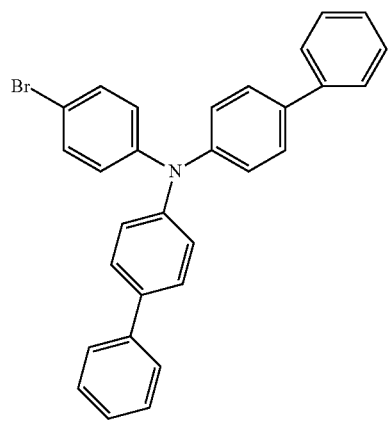<br>[499128-71-1] |

| Product |
|---|
| 6a 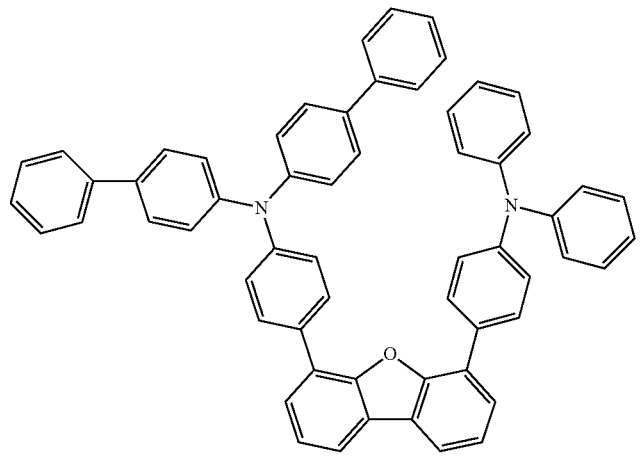 [SMILES: c1ccc(-c2ccc(N(c3ccc(-c4ccccc4)cc3)c3ccc(-c4cccc5c4oc4c(-c6ccc(N(c7ccccc7)c7ccccc7)cc6)cccc45)cc3)cc2)cc1] |
| 6b 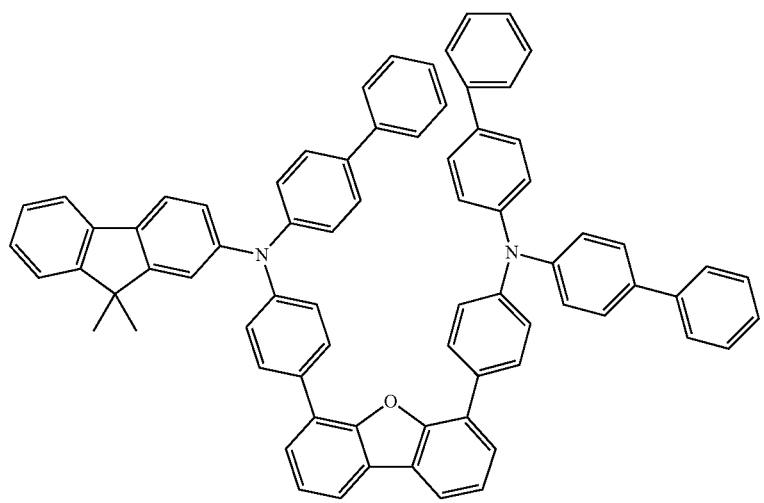 [SMILES: CC1(C)c2ccccc2-c2ccc(N(c3ccc(-c4ccccc4)cc3)c3ccc(-c4cccc5c4oc4c(-c6ccc(N(c7ccc(-c8ccccc8)cc7)c7ccc(-c8ccccc8)cc7)cc6)cccc45)cc3)cc21] |
| 6c 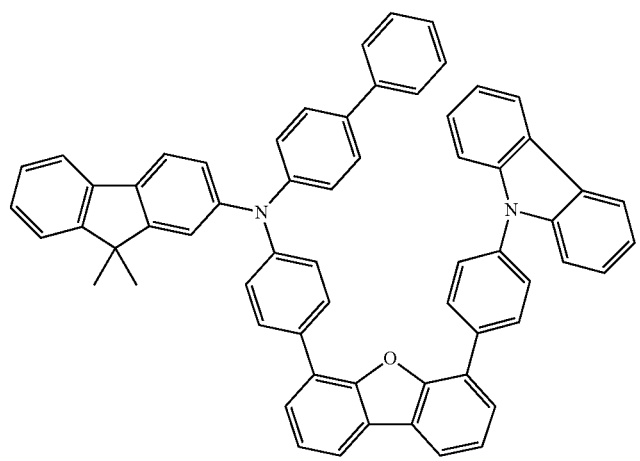 [SMILES: CC1(C)c2ccccc2-c2ccc(N(c3ccc(-c4ccccc4)cc3)c3ccc(-c4cccc5c4oc4c(-c6ccc(-n7c8ccccc8c8ccccc87)cc6)cccc45)cc3)cc21] |

6d
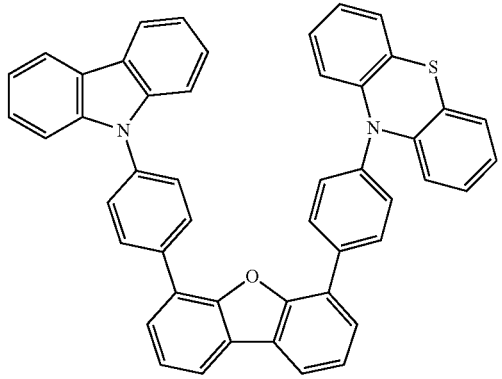 [SMILES: c1ccc2c(c1)Sc1ccccc1N2c1ccc(-c2cccc3c2oc2c(-c4ccc(-n5c6ccccc6c6ccccc65)cc4)cccc23)cc1]
6e
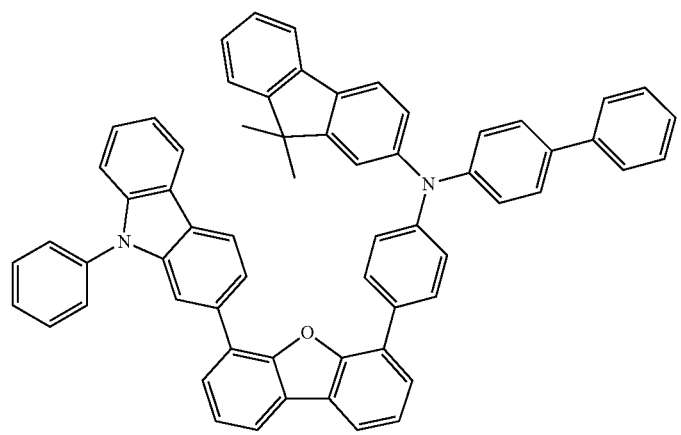 [SMILES: CC1(C)c2ccccc2-c2ccc(N(c3ccc(-c4ccccc4)cc3)c3ccc(-c4cccc5c4oc4c(-c6ccc7c8ccccc8n(-c8ccccc8)c7c6)cccc45)cc3)cc21]
6f
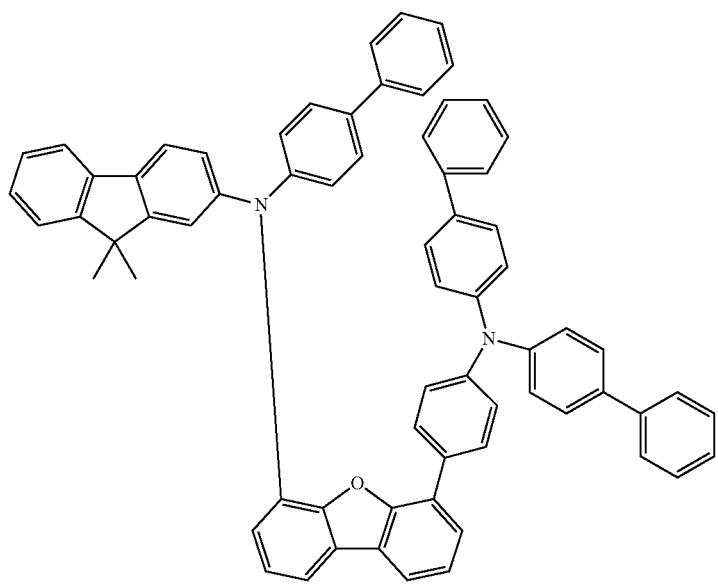 [SMILES: CC1(C)c2ccccc2-c2ccc(N(c3ccc(-c4ccccc4)cc3)c3cccc4c3oc3c(-c5ccc(N(c6ccc(-c7ccccc7)cc6)c6ccc(-c7ccccc7)cc6)cc5)cccc34)cc21]

6g
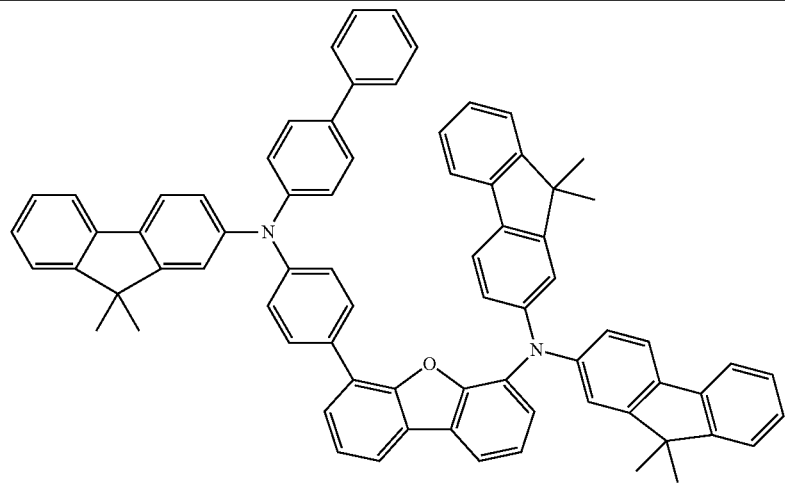
6h
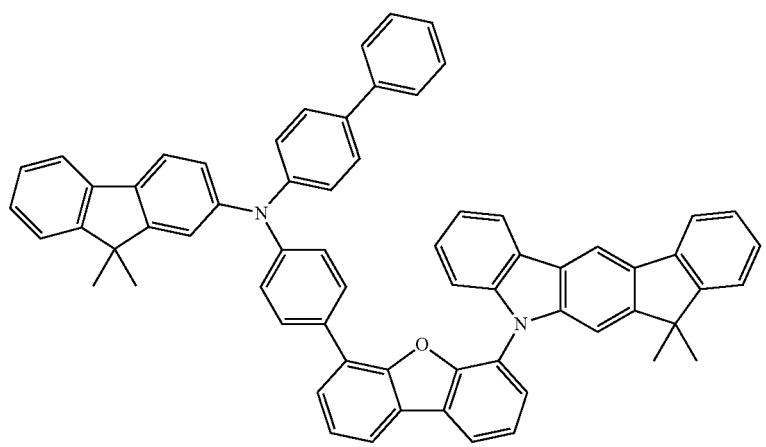 [SMILES: CC1(C)c2ccccc2-c2ccc(N(c3ccc(-c4ccccc4)cc3)c3ccc(-c4cccc5c4oc4c(-n6c7ccccc7c7cc8c(cc76)C(C)(C)c6ccccc6-8)cccc45)cc3)cc21]
6i
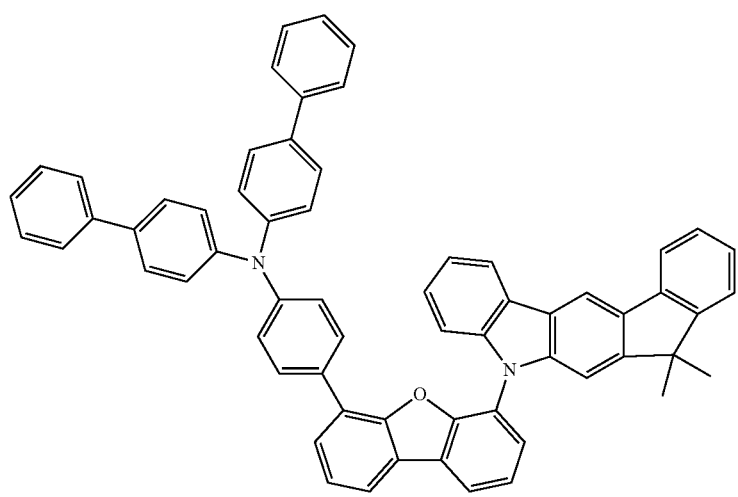 [SMILES: CC1(C)c2ccccc2-c2cc3c4ccccc4n(-c4cccc5c4oc4c(-c6ccc(N(c7ccc(-c8ccccc8)cc7)c7ccc(-c8ccccc8)cc7)cc6)cccc45)c3cc21]

6j
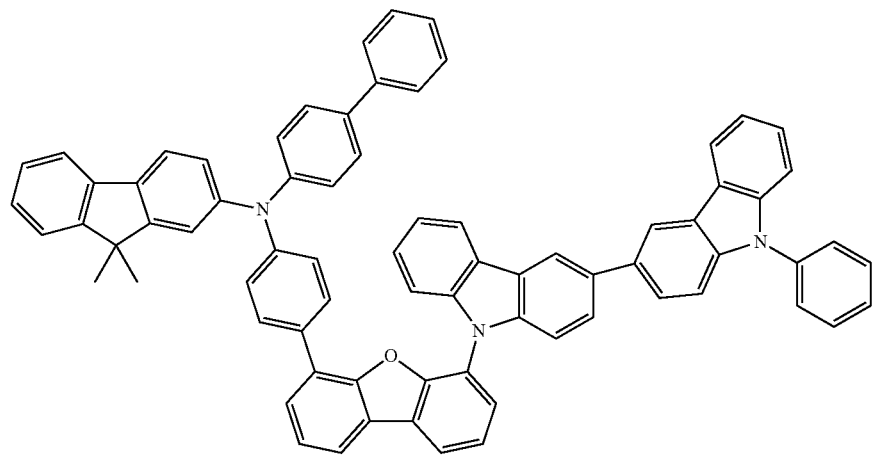 [SMILES: CC1(C)c2ccccc2-c2ccc(N(c3ccc(-c4ccccc4)cc3)c3ccc(-c4cccc5c4oc4c(-n6c7ccccc7c7cc(-c8ccc9c(c8)c8ccccc8n9-c8ccccc8)ccc76)cccc45)cc3)cc21]
6k
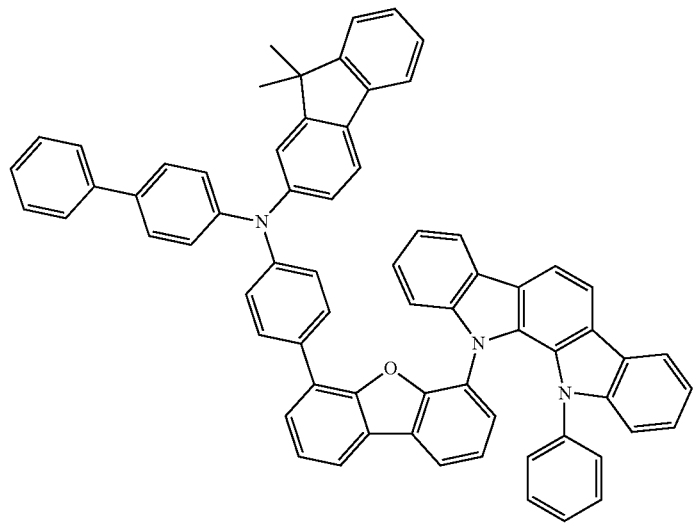 [SMILES: CC1(C)c2ccccc2-c2ccc(N(c3ccc(-c4ccccc4)cc3)c3ccc(-c4cccc5c4oc4c(-n6c7ccccc7c7ccc8c9ccccc9n(-c9ccccc9)c8c76)cccc45)cc3)cc21]
6l
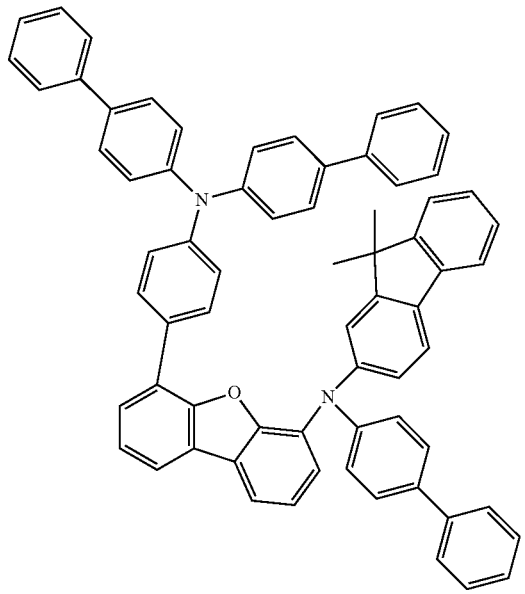 [SMILES: CC1(C)c2ccccc2-c2ccc(N(c3ccc(-c4ccccc4)cc3)c3cccc4c3oc3c(-c5ccc(N(c6ccc(-c7ccccc7)cc6)c6ccc(-c7ccccc7)cc6)cc5)cccc34)cc21]

6n
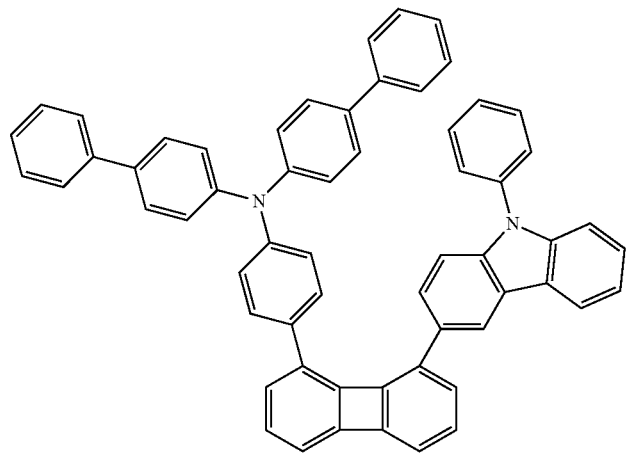 [SMILES: c1ccc(-c2ccc(N(c3ccc(-c4ccccc4)cc3)c3ccc(-c4cccc5c4-c4c(-c6ccc7c(c6)c6ccccc6n7-c6ccccc6)cccc4-5)cc3)cc2)cc1]
6o
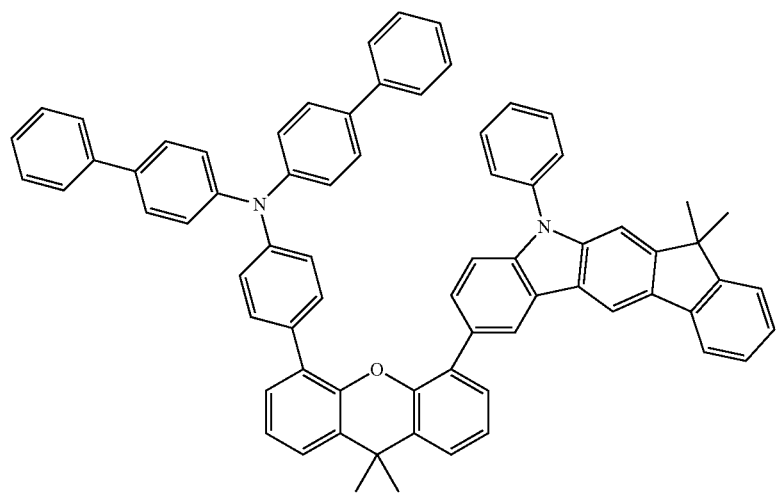 [SMILES: CC1(C)c2ccccc2-c2cc3c4cc(-c5cccc6c5Oc5c(-c7ccc(N(c8ccc(-c9ccccc9)cc8)c8ccc(-c9ccccc9)cc8)cc7)cccc5C6(C)C)ccc4n(-c4ccccc4)c3cc21]
6p
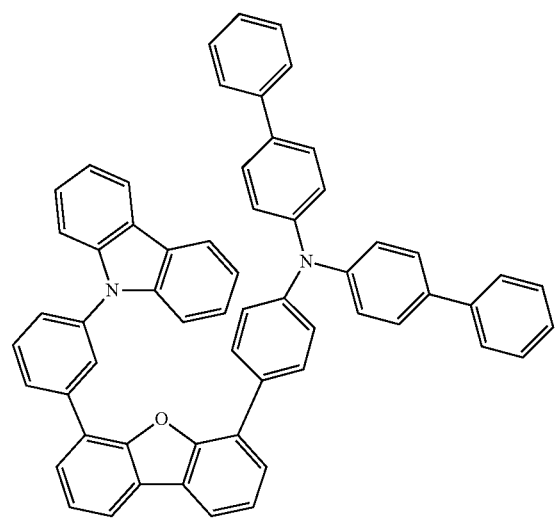 [SMILES: c1ccc(-c2ccc(N(c3ccc(-c4ccccc4)cc3)c3ccc(-c4cccc5c4oc4c(-c6cccc(-n7c8ccccc8c8ccccc87)c6)cccc45)cc3)cc2)cc1]

-continued
6r
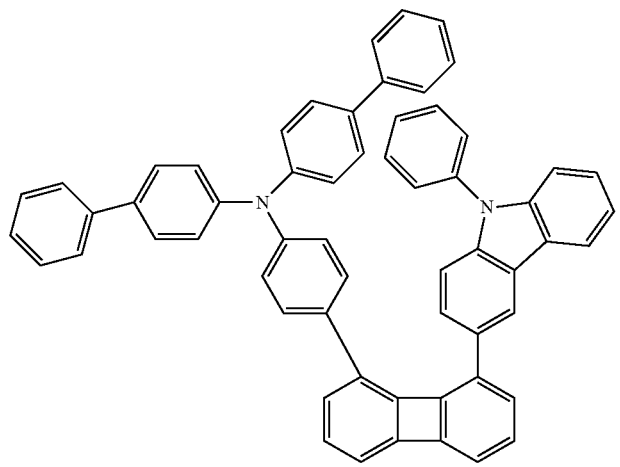 [SMILES: c1ccc(-c2ccc(N(c3ccc(-c4ccccc4)cc3)c3ccc(-c4cccc5c4-c4c(-c6ccc7c(c6)c6ccccc6n7-c6ccccc6)cccc4-5)cc3)cc2)cc1]
6s
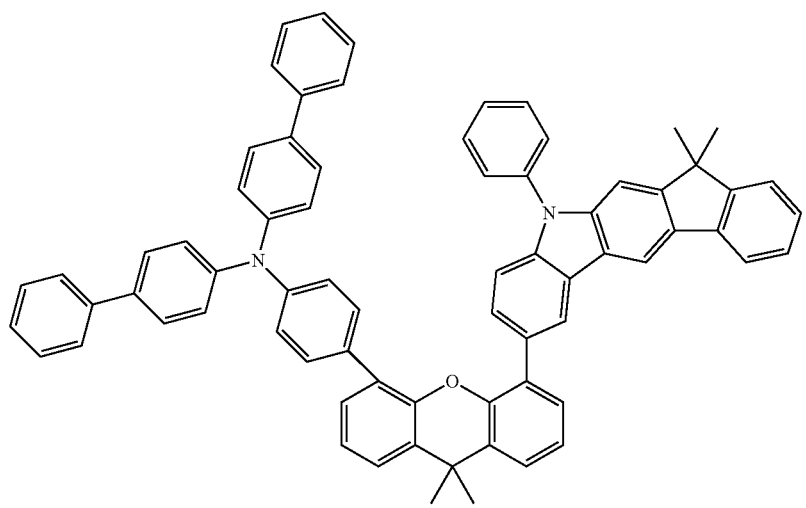 [SMILES: CC1(C)c2ccccc2-c2cc3c4cc(-c5cccc6c5Oc5c(-c7ccc(N(c8ccc(-c9ccccc9)cc8)c8ccc(-c9ccccc9)cc8)cc7)cccc5C6(C)C)ccc4n(-c4ccccc4)c3cc21]
6t
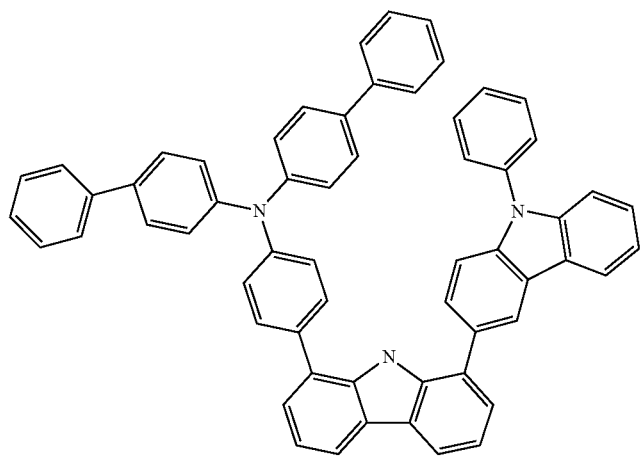 [SMILES: c1ccc(-c2ccc(N(c3ccc(-c4ccccc4)cc3)c3ccc(-c4cccc5c4[nH]c4c(-c6ccc7c(c6)c6ccccc6n7-c6ccccc6)cccc45)cc3)cc2)cc1]
| | Yield |
|---|---|
| 6a | 60% |
| 6b | 77% |
| 6c | 82% |
| 6d | 78% |
| 6e | 84% |
-continued
| | Yield |
|---|---|
| 6f | 63% |
| 6g | 52% |
| 6h | 71% |
| 6i | 69% |

-continued

| | Yield |
|---|---|
| 6j | 73% |
| 6k | 52% |
| 6l | 48% |
| 6n | 56% |
| 6o | 67% |
| 6p | 69% |
| 6r | 45% |
| 6s | 64% |
| 6t | 60% |

Synthesis of Precursors

Example Int-7: 3-(6-Bromodibenzofuran-4-yl)-9-phenyl-9H-carbazole

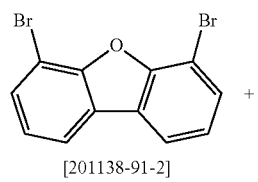

[201138-91-2]

+

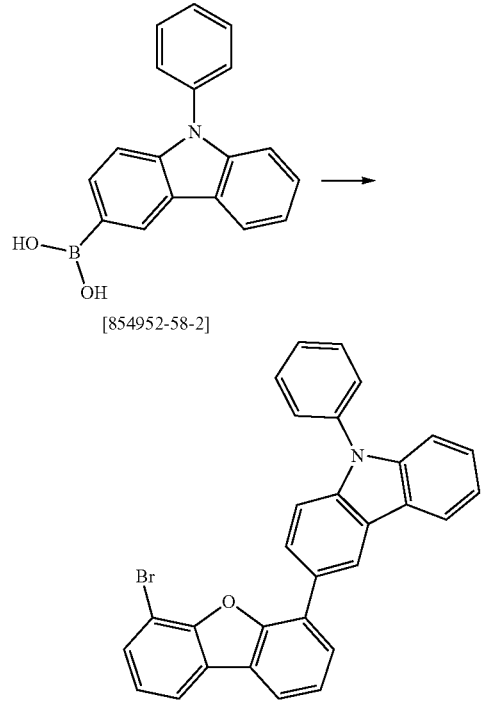

[854952-58-2]

10.43 g (32 mmol) of B-(9-phenyl-9H-carbazol-3-yl) boronic acid, 8.9 g (31.6 mmol) of 4,6-dibromodibenzofuran and 31 ml (63 mmol) of $Na_2CO_3$ (2M solution) are suspended in 120 ml of toluene and 120 ml of ethanol. 0.73 g (0.63 mmol) of $Pd(PPh_3)_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 11.4 g (23 mmol), corresponding to 73% of theory.

The following compounds can be obtained analogously:

| | Starting material 1 | Starting material 2 |
|---|---|---|
| Int-7a | 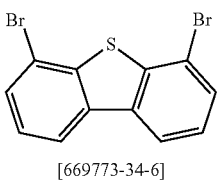 [SMILES: Brc1cccc2c1sc1c(Br)cccc12]<br>[669773-34-6] | 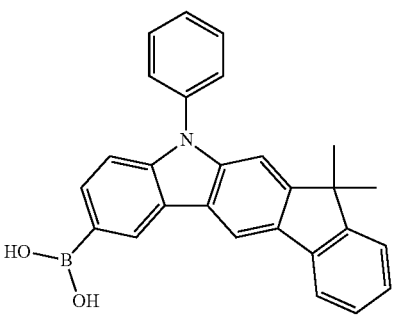<br>[1379585-25-7] |

Int-7b 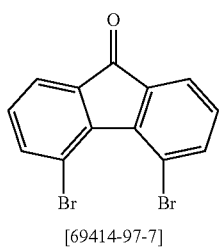 [SMILES: O=C1c2cccc(Br)c2-c2c(Br)cccc21] [69414-97-7] 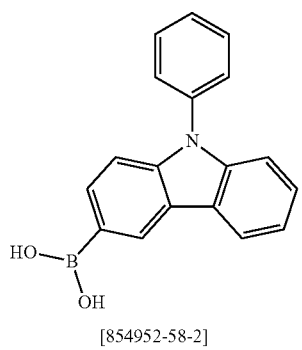 [SMILES: OB(O)c1ccc2c(c1)c1ccccc1n2-c1ccccc1] [854952-58-2]
Int-7c 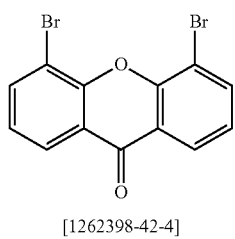 [SMILES: O=c1c2cccc(Br)c2oc2c(Br)cccc12] [1262398-42-4] 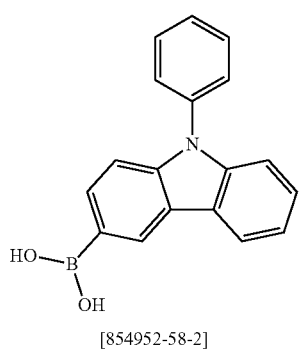 [SMILES: OB(O)c1ccc2c(c1)c1ccccc1n2-c1ccccc1] [854952-58-2]
Int-7d 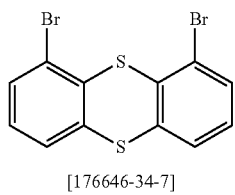 [SMILES: Brc1cccc2c1Sc1c(Br)cccc1S2] [176646-34-7] 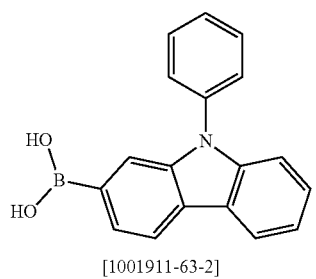 [SMILES: OB(O)c1ccc2c3ccccc3n(-c3ccccc3)c2c1] [1001911-63-2]
Int-7e 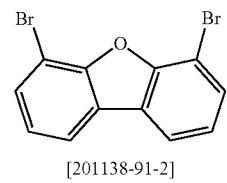 [SMILES: Brc1cccc2c1oc1c(Br)cccc12] [201138-91-2] 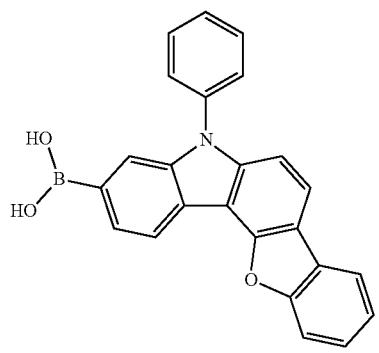 [1391729-62-6]

-continued
Int-7f 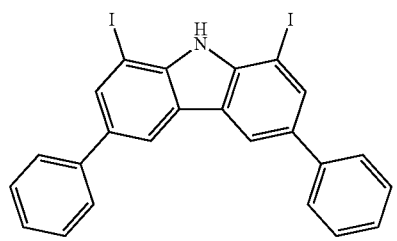
[501330-43-4]
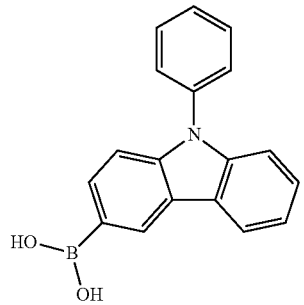
[854952-58-2]
Int-7g 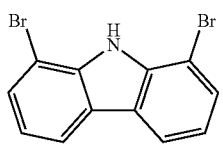
[553663-65-3]
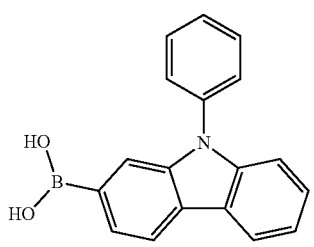
[1001911-63-2]
Int-7h 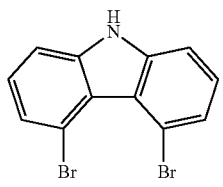
[905702-33-2]
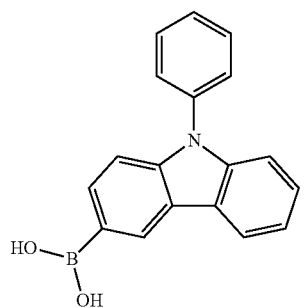
[854952-58-2]
Int-7i 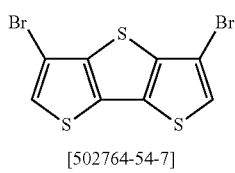
[502764-54-7]
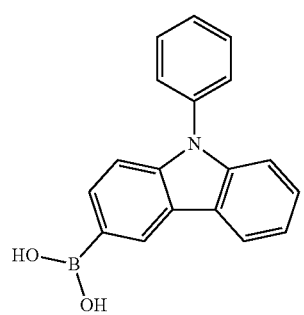
[854952-58-2]

| | | |
|---|---|---|
| Int-7j | 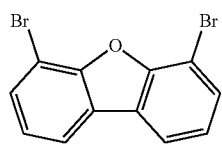
[201138-91-2] | 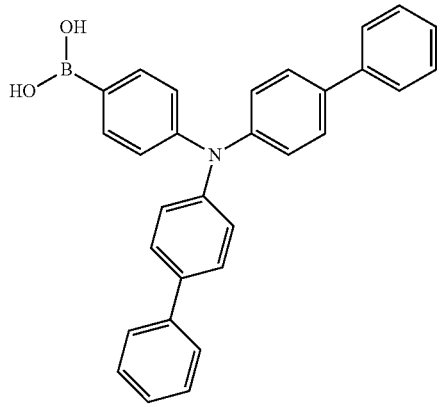
[943836-24-6] |
| Int-7k | 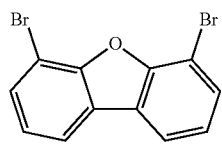
[201138-91-2] | 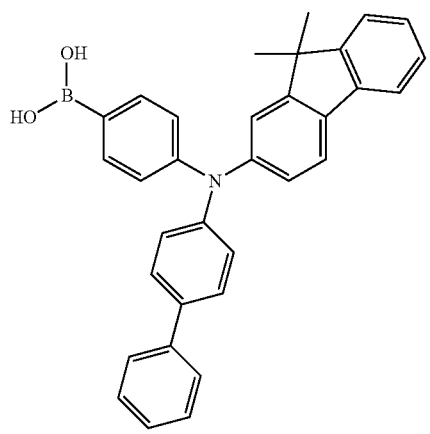
[1265177-27-2] |
| | Product | Yield |
|---|---|---|
| Int-7a | 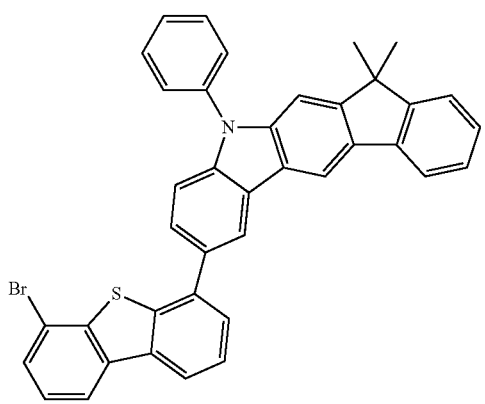 [SMILES: CC1(C)c2ccccc2-c2cc3c4cc(-c5cccc6c5sc5c(Br)cccc56)ccc4n(-c4ccccc4)c3cc21] | 51% |

| | | |
|---|---|---|
| Int-7b | 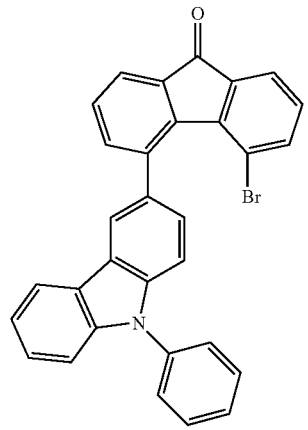 [SMILES: O=C1c2cccc(Br)c2-c2c1cccc2-c1ccc2c(c1)c1ccccc1n2-c1ccccc1] | 65% |
| Int-7c | 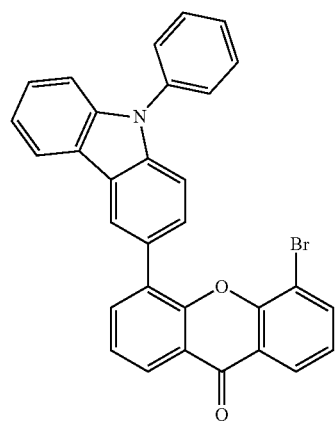 [SMILES: O=c1c2cccc(Br)c2oc2c(-c3ccc4c(c3)c3ccccc3n4-c3ccccc3)cccc12] | 69% |
| Int-7d | 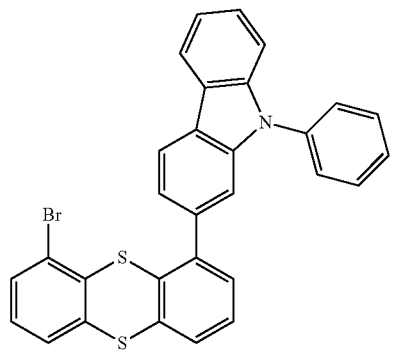 [SMILES: Brc1cccc2c1Sc1c(cccc1-c1ccc3c4ccccc4n(-c4ccccc4)c3c1)S2] | 67% |
| Int-7e | 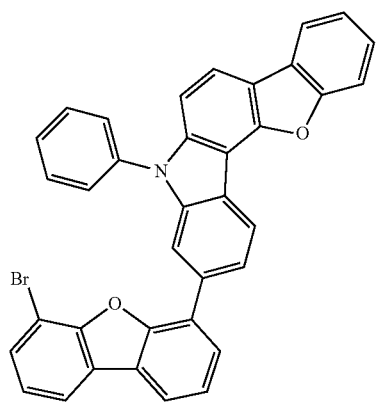 [SMILES: Brc1cccc2c1oc1c(-c3ccc4c5c6oc7ccccc7c6ccc5n(-c5ccccc5)c4c3)cccc12] | 62% |

| | | |
|---|---|---|
| Int-7f | 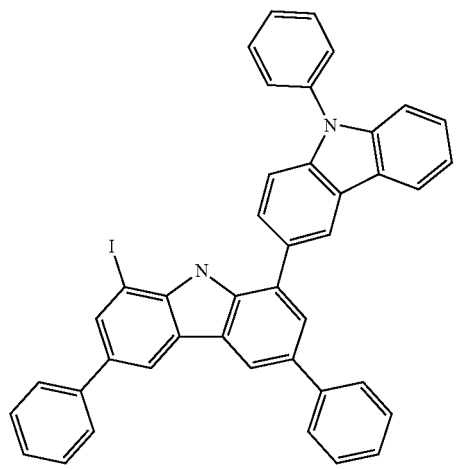 [SMILES: Ic1cc(-c2ccccc2)cc2c1[nH]c1c(-c3ccc4c(c3)c3ccccc3n4-c3ccccc3)cc(-c3ccccc3)cc12] | 62% |
| Int-7g | 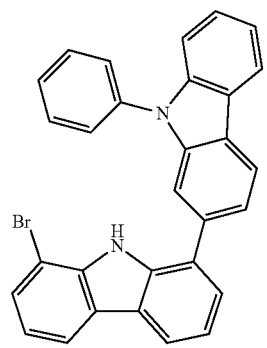 [SMILES: Brc1cccc2c1[nH]c1c(-c3ccc4c5ccccc5n(-c5ccccc5)c4c3)cccc12] | 61% |
| Int-7h | 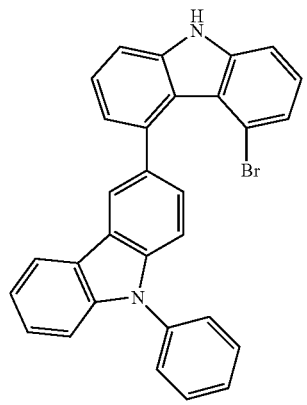 [SMILES: Brc1cccc2[nH]c3cccc(-c4ccc5c(c4)c4ccccc4n5-c4ccccc4)c3c12] | 64% |
| Int-7i | 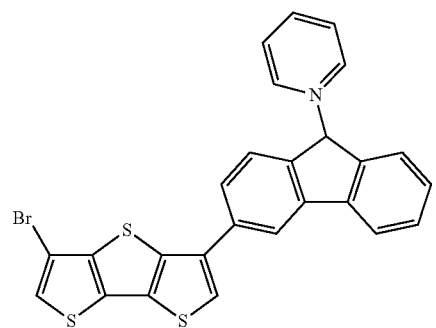 | 66% |

| | | |
|---|---|---|
| Int-7j | 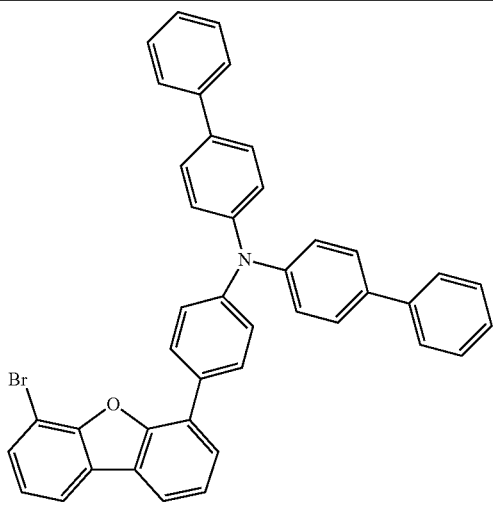 | 62% |
| Int-7k | 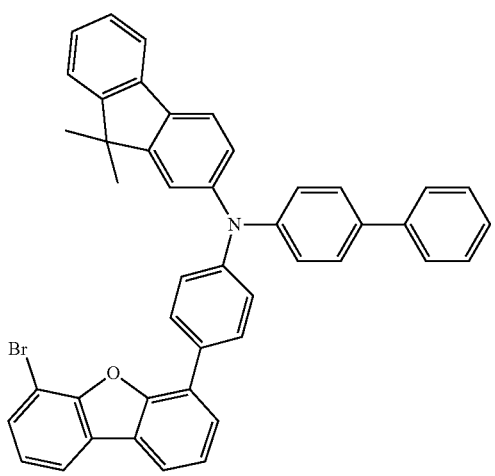 [SMILES: CC1(C)c2ccccc2-c2ccc(N(c3ccc(-c4ccccc4)cc3)c3ccc(-c4cccc5c4oc4c(Br)cccc45)cc3)cc21] | 65% |
Synthesis of Compounds According to the Invention:
The following compounds can be obtained analogously by double addition reaction with corresponding boronic acids:
| | Starting material 1 | Starting material 2 |
|---|---|---|
| 71 | 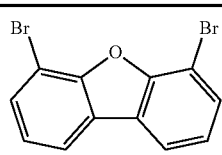<br>[201138-91-2] | 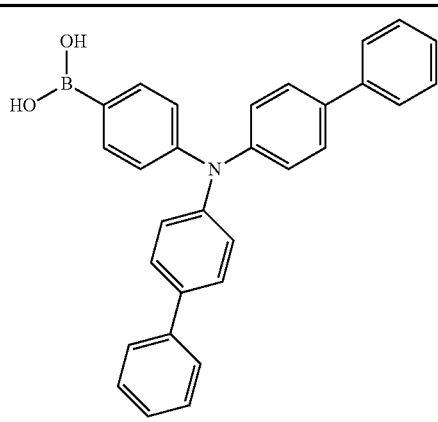<br>[943836-24-6] |

-continued
7m 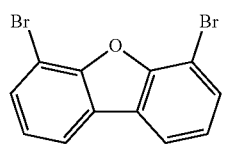
[201138-91-2]
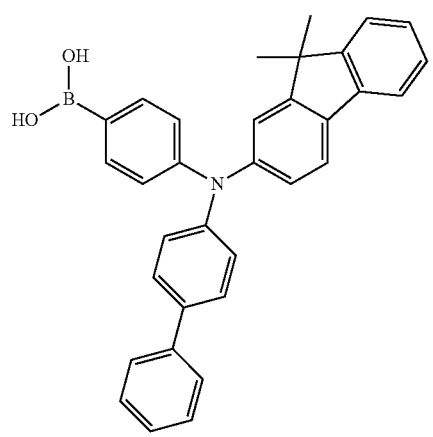
[1265177-27-2]
7n 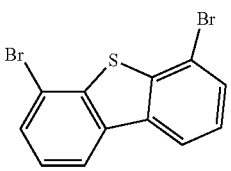 [SMILES: Brc1cccc2c1sc1c(Br)cccc12]
[943836-24-6]
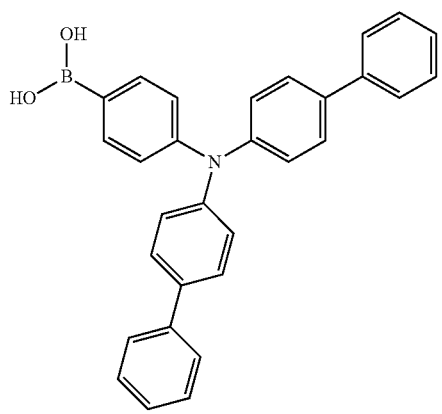
[943836-24-6]
7o 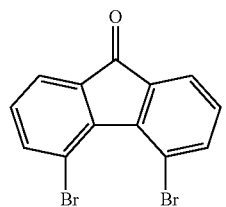 [SMILES: O=C1c2cccc(Br)c2-c2c(Br)cccc21]
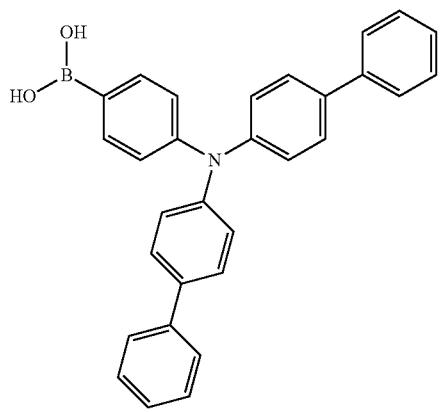
[943836-24-6]

-continued
7p 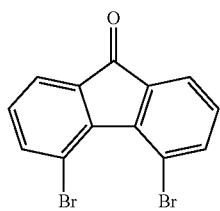 [SMILES: O=C1c2cccc(Br)c2-c2c(Br)cccc21] 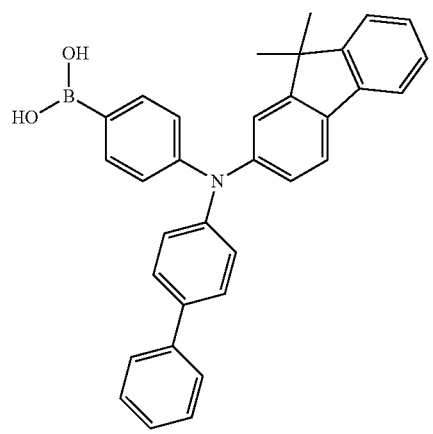
[1265177-27-2]
7q 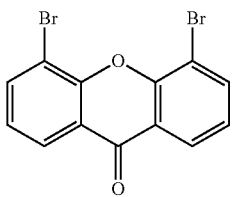 [SMILES: O=c1c2cccc(Br)c2oc2c(Br)cccc12] 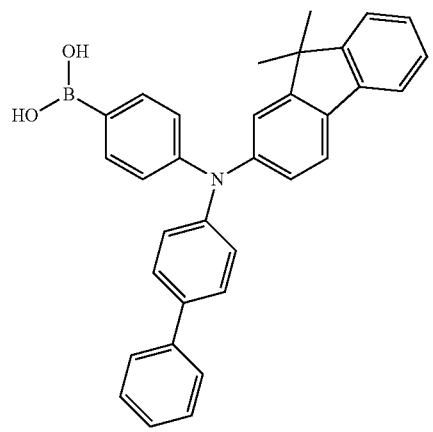
[1265177-27-2]
7r 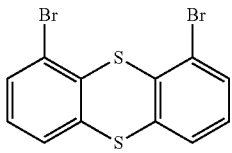 [SMILES: Brc1cccc2c1Sc1c(Br)cccc1S2] 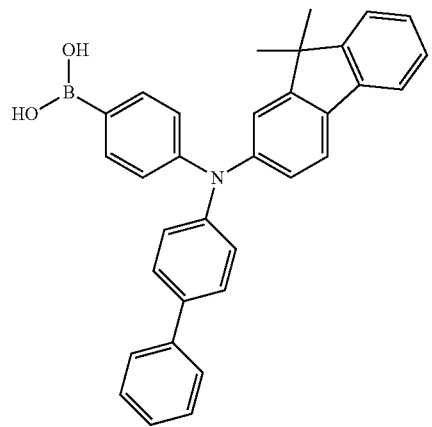
[1265177-27-2]

-continued
| | | |
|---|---|---|
| 7s | 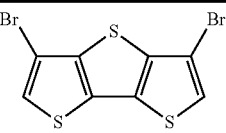 | 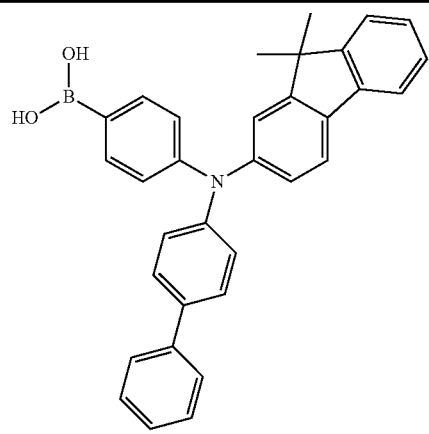<br>[1265177-27-2] |
| 7t | 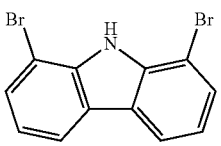 [SMILES: Brc1cccc2c1[nH]c1c(Br)cccc12] | 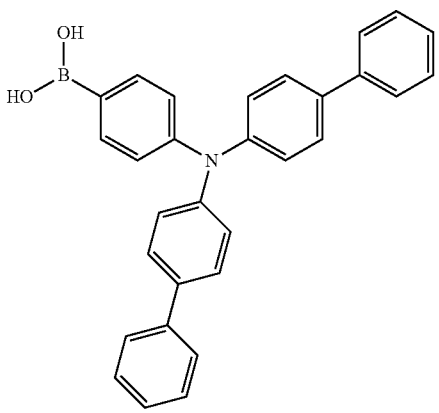<br>[943836-24-6] |
| 7u | 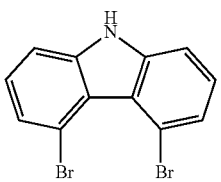 [SMILES: Brc1cccc2[nH]c3cccc(Br)c3c12] | 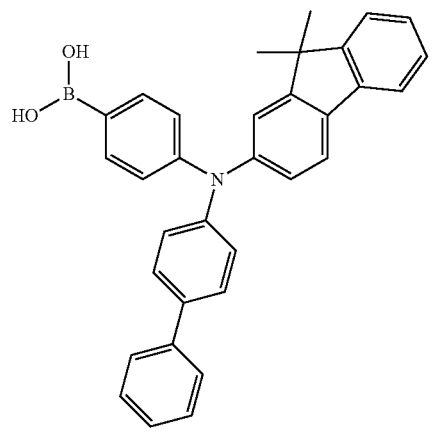<br>[1265177-27-2] |

| | |
|---|---|
| 7v | 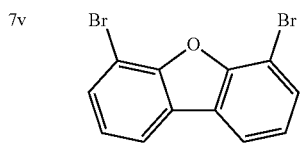  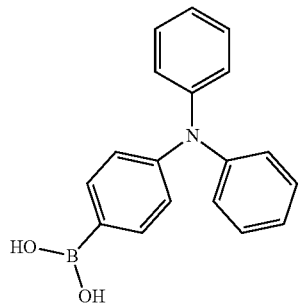 |
| | [201138-91-2]      [201802-67-7] |
Product
71
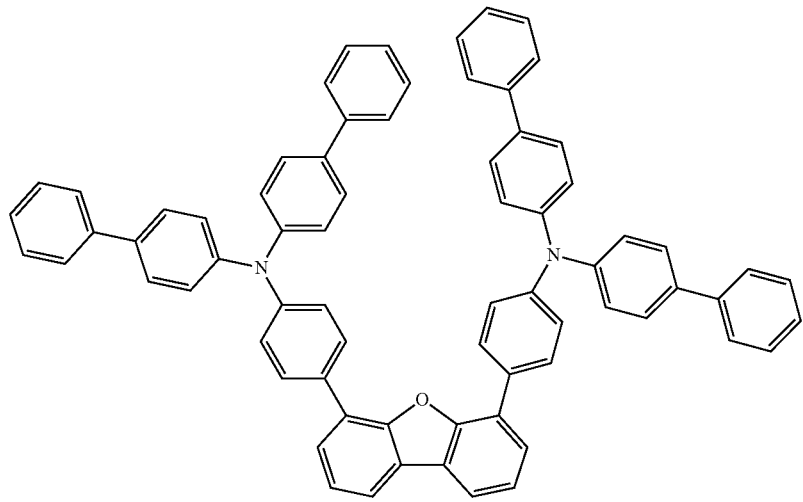 [SMILES: c1ccc(-c2ccc(N(c3ccc(-c4ccccc4)cc3)c3ccc(-c4cccc5c4oc4c(-c6ccc(N(c7ccc(-c8ccccc8)cc7)c7ccc(-c8ccccc8)cc7)cc6)cccc45)cc3)cc2)cc1]
7m
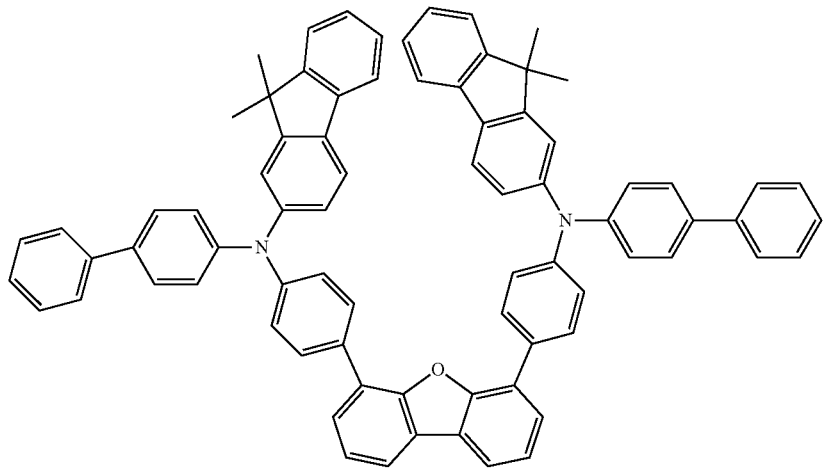 [SMILES: CC1(C)c2ccccc2-c2ccc(N(c3ccc(-c4ccccc4)cc3)c3ccc(-c4cccc5c4oc4c(-c6ccc(N(c7ccc(-c8ccccc8)cc7)c7ccc8c(c7)C(C)(C)c7ccccc7-8)cc6)cccc45)cc3)cc21]

-continued
7n
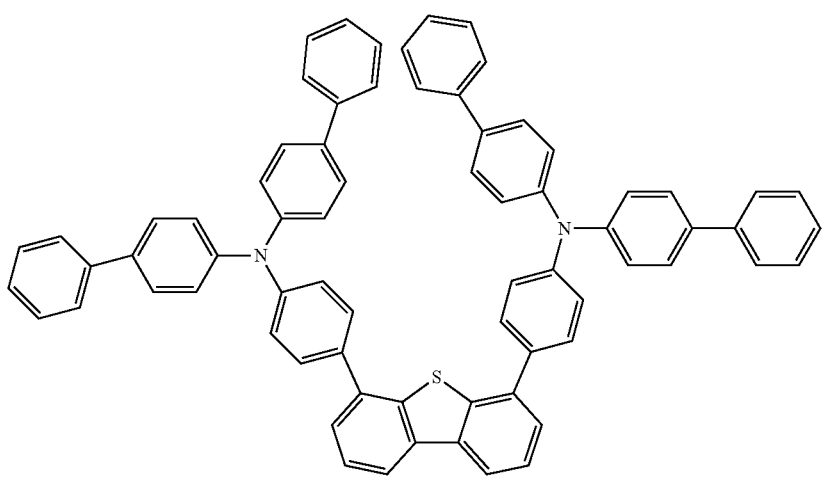 [SMILES: c1ccc(-c2ccc(N(c3ccc(-c4ccccc4)cc3)c3ccc(-c4cccc5c4sc4c(-c6ccc(N(c7ccc(-c8ccccc8)cc7)c7ccc(-c8ccccc8)cc7)cc6)cccc45)cc3)cc2)cc1]
7o
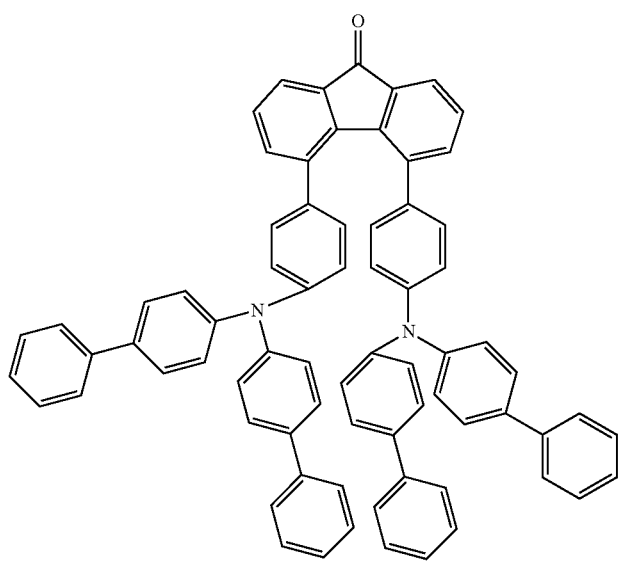 [SMILES: O=C1c2cccc(-c3ccc(N(c4ccc(-c5ccccc5)cc4)c4ccc(-c5ccccc5)cc4)cc3)c2-c2c1cccc2-c1ccc(N(c2ccc(-c3ccccc3)cc2)c2ccc(-c3ccccc3)cc2)cc1]
7p
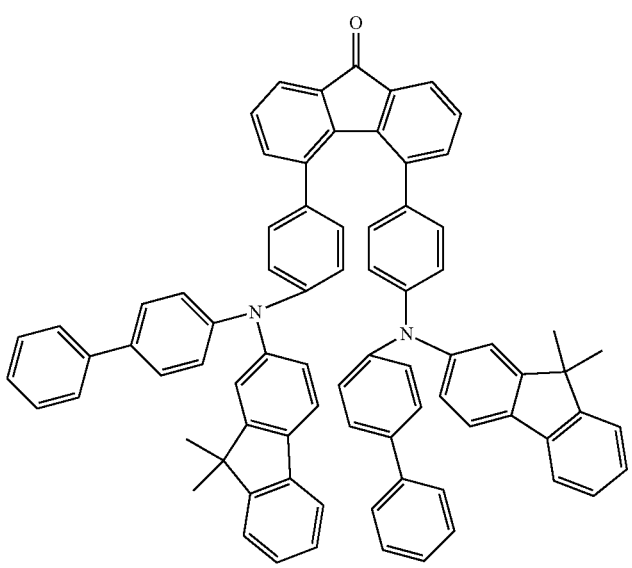 [SMILES: CC1(C)c2ccccc2-c2ccc(N(c3ccc(-c4ccccc4)cc3)c3ccc(-c4cccc5c4-c4c(cccc4-c4ccc(N(c6ccc(-c7ccccc7)cc6)c6ccc7c(c6)C(C)(C)c6ccccc6-7)cc4)C5=O)cc3)cc21]

-continued
7q
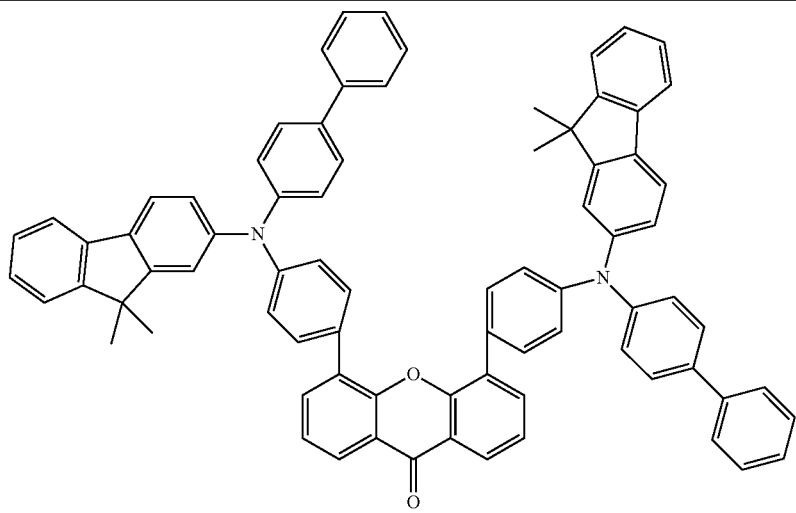
7r
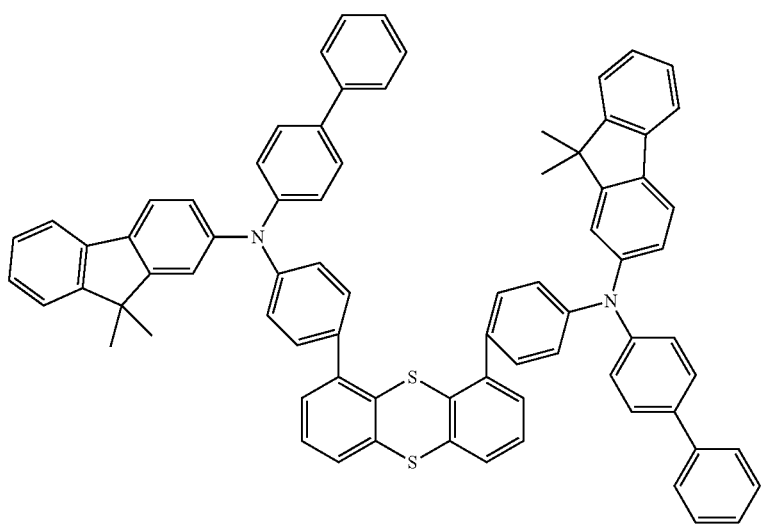 [SMILES: CC1(C)c2ccccc2-c2ccc(N(c3ccc(-c4ccccc4)cc3)c3ccc(-c4cccc5c4Sc4c(cccc4-c4ccc(N(c6ccc(-c7ccccc7)cc6)c6ccc7c(c6)C(C)(C)c6ccccc6-7)cc4)S5)cc3)cc21]
7s
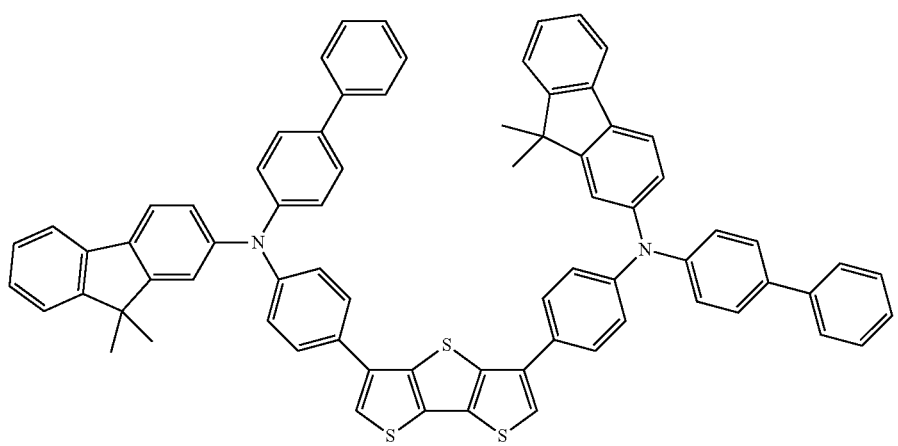 [SMILES: CC1(C)c2ccccc2-c2ccc(N(c3ccc(-c4ccccc4)cc3)c3ccc(-c4csc5c4sc4c(-c6ccc(N(c7ccc(-c8ccccc8)cc7)c7ccc8c(c7)C(C)(C)c7ccccc7-8)cc6)csc45)cc3)cc21]

7t
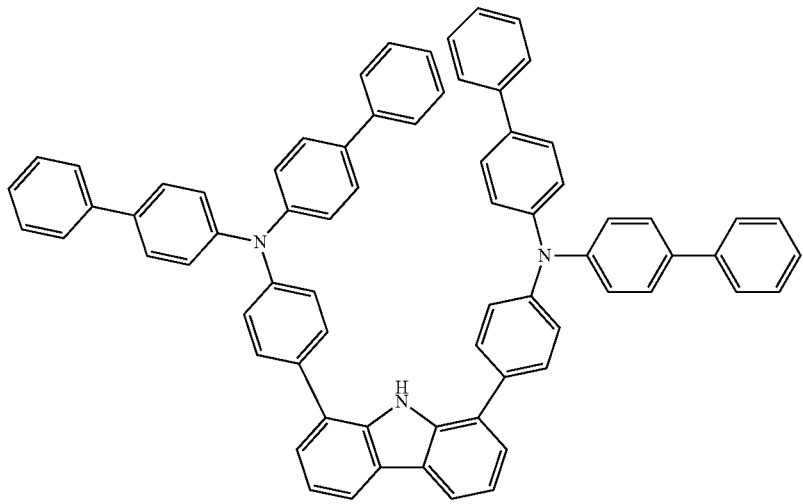 [SMILES: c1ccc(-c2ccc(N(c3ccc(-c4ccccc4)cc3)c3ccc(-c4cccc5c4[nH]c4c(-c6ccc(N(c7ccc(-c8ccccc8)cc7)c7ccc(-c8ccccc8)cc7)cc6)cccc45)cc3)cc2)cc1]
7u
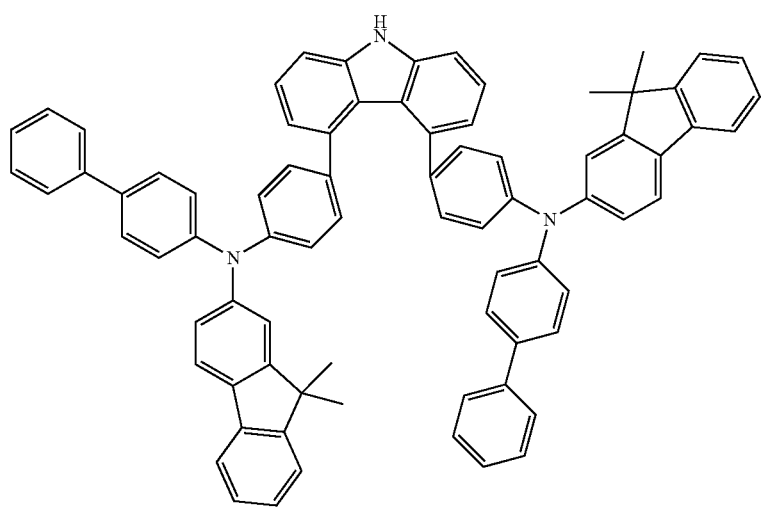 [SMILES: CC1(C)c2ccccc2-c2ccc(N(c3ccc(-c4ccccc4)cc3)c3ccc(-c4cccc5[nH]c6cccc(-c7ccc(N(c8ccc(-c9ccccc9)cc8)c8ccc9c(c8)C(C)(C)c8ccccc8-9)cc7)c6c45)cc3)cc21]

7v

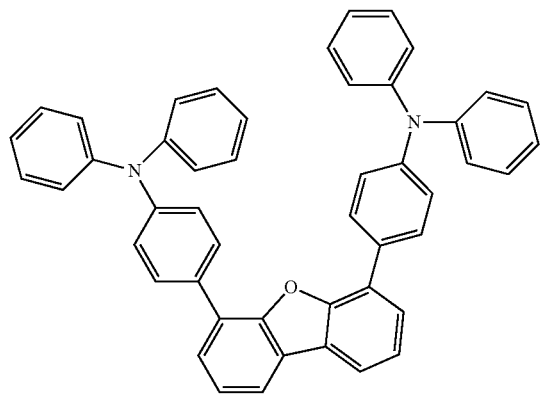 [SMILES: c1ccc(N(c2ccccc2)c2ccc(-c3cccc4c3oc3c(-c5ccc(N(c6ccccc6)c6ccccc6)cc5)cccc34)cc2)cc1]

| | Yield |
|---|---|
| 7l | 52% |
| 7m | 67% |
| 7n | 80% |
| 7o | 79% |
| 7p | 58% |
| 7q | 78% |
| 7r | 87% |
| 7s | 87% |
| 7t | 83% |
| 7u | 80% |
| 7v | 87% |

Example 8: Bisbiphenyl-4-yl-(4-{1-[3-eth-(Z)-ylidene-7-(9-phenyl-9H-carbazol-3-yl)-3H-benzofuran-(2Z)-ylidene]ethyl}phenyl)amine

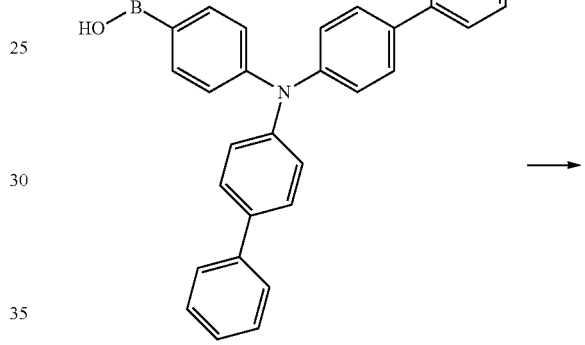

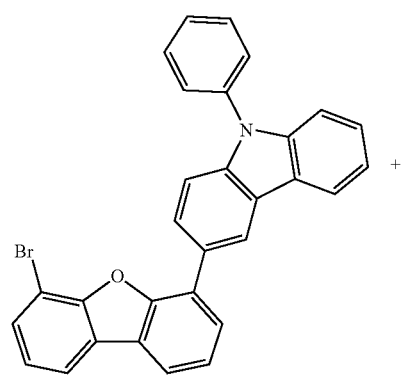 +

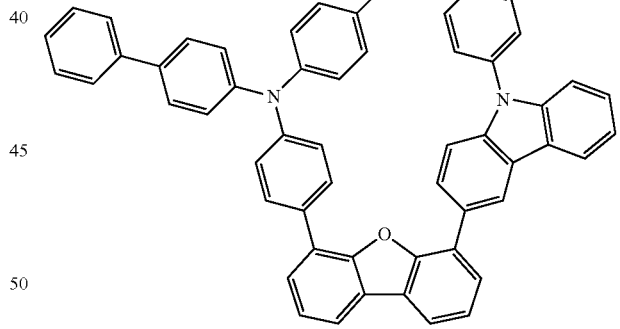

87 g (180.1 mmol) of 3-(6-bromodibenzofuran-4-yl)-9-phenyl-9H-carbazole, 79 g (180.7 mmol) of B-[4-[bis([1,1'-biphenyl]-4-yl]amino]phenylboronic acid and 38.3 g (180.7 mmol) of potassium phosphate are suspended in 500 ml of toluene, 250 ml of 1,4-dioxane and 120 ml of water. 1.3 g (4.1 mmol) of tri(o-tolyl)phosphine and then 461 mg (2 mmol) of palladium(II) acetate are added to the mixture, and the reaction mixture is heated under reflux for 48 h. After cooling, the organic phase is separated off, washed three times with 100 ml of water each time and evaporated. After purification by column chromatography (SiO$_2$, n-heptane/dichloromethane 3/1), the foam obtained is dissolved in dichloromethane and precipitated using ethanol. The residue is recrystallised from toluene and from dichloromethane and finally sublimed in a high vacuum (p=5×10$^{-5}$ mbar). Yield: 129 g (160 mmol), 90%. Purity about 99% according to HPLC.

The following compounds can be obtained analogously:

| | Starting material 1 | Starting material 2 |
|---|---|---|
| 8a | | [1265177-27-2] |
| 8b | | [201802-67-7] |
| 8c | | [201802-67-7] |

-continued
8d
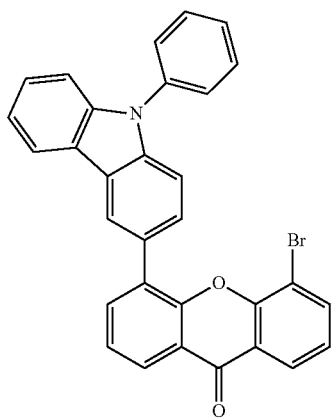 [SMILES: O=c1c2cccc(Br)c2oc2c(-c3ccc4c(c3)c3ccccc3n4-c3ccccc3)cccc12]
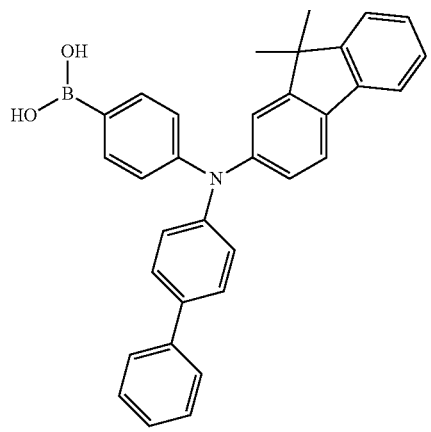
[1265177-27-2]
8e
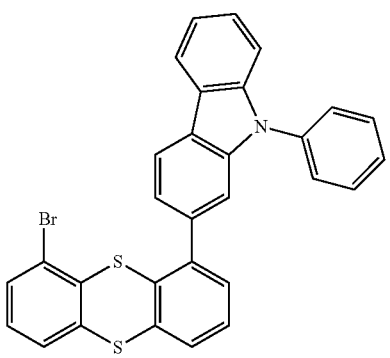 [SMILES: Brc1cccc2c1Sc1c(cccc1-c1ccc3c4ccccc4n(-c4ccccc4)c3c1)S2]
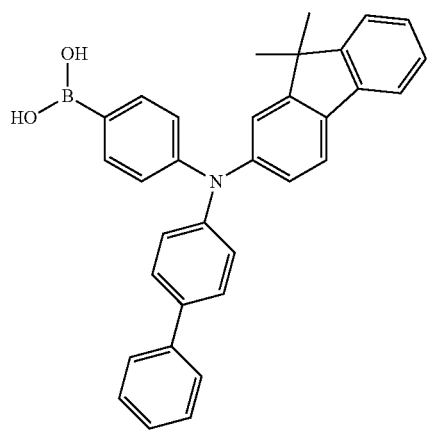
[1265177-27-2]
8f
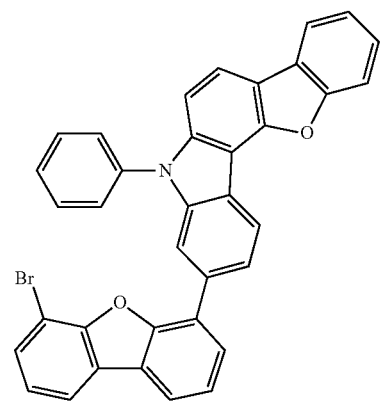 [SMILES: Brc1cccc2c1oc1c(-c3ccc4c5c6oc7ccccc7c6ccc5n(-c5ccccc5)c4c3)cccc12]
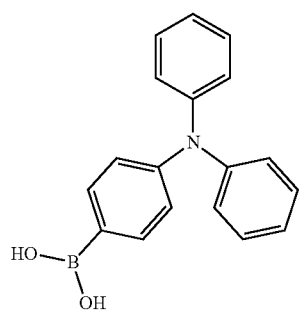
[201802-67-7]

8g
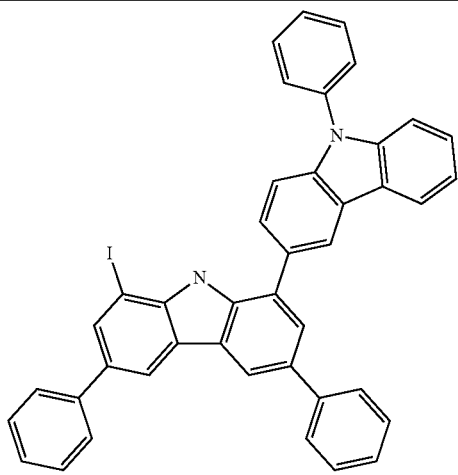
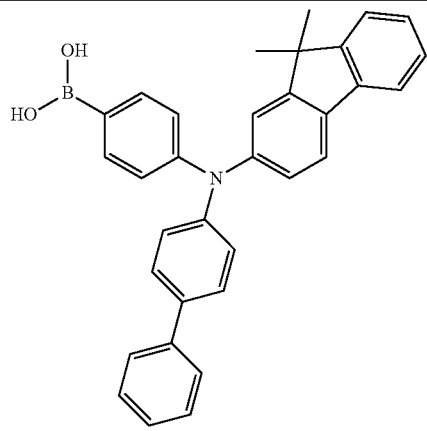
[1265177-27-2]
8h
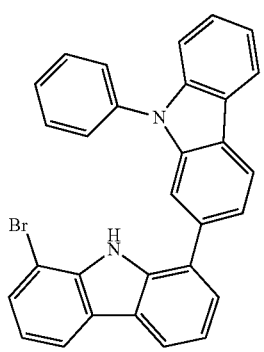 [SMILES: Brc1cccc2c1[nH]c1c(-c3ccc4c5ccccc5n(-c5ccccc5)c4c3)cccc12]
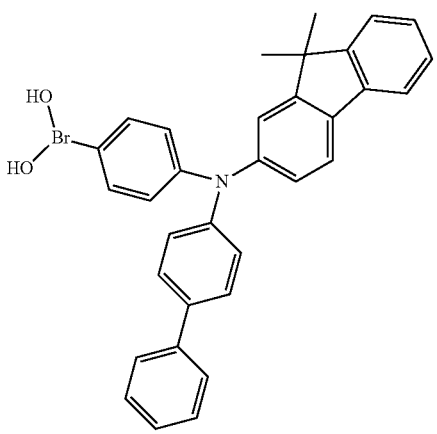
8i
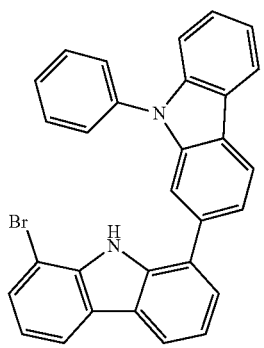 [SMILES: Brc1cccc2c1[nH]c1c(-c3ccc4c5ccccc5n(-c5ccccc5)c4c3)cccc12]
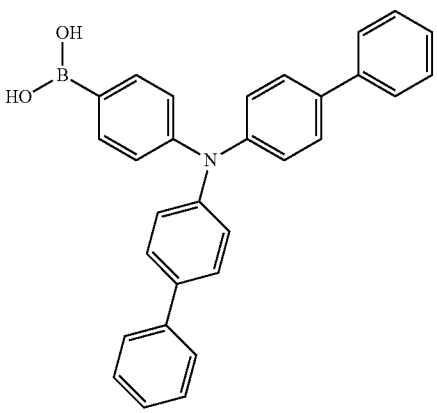
[943836-24-6]

8j 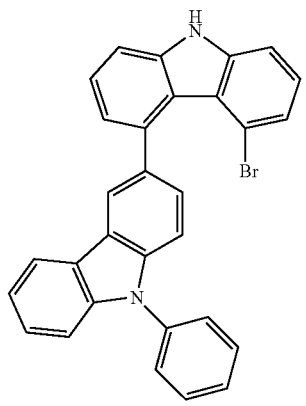 [SMILES: Brc1cccc2[nH]c3cccc(-c4ccc5c(c4)c4ccccc4n5-c4ccccc4)c3c12] 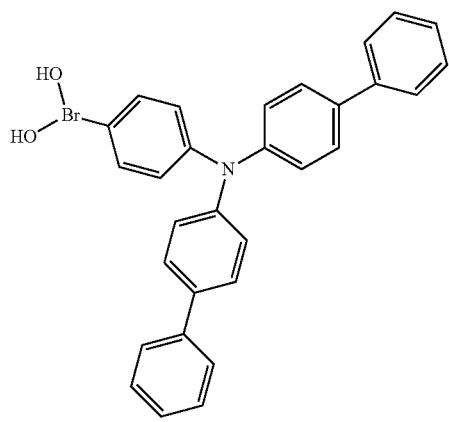
8k 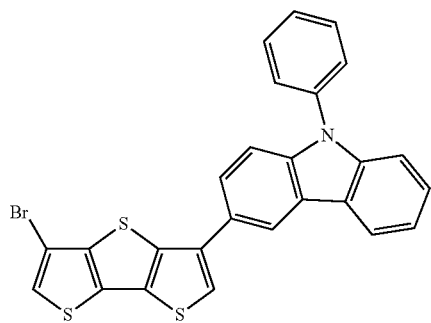 [SMILES: Brc1csc2c1sc1c(-c3ccc4c(c3)c3ccccc3n4-c3ccccc3)csc12] 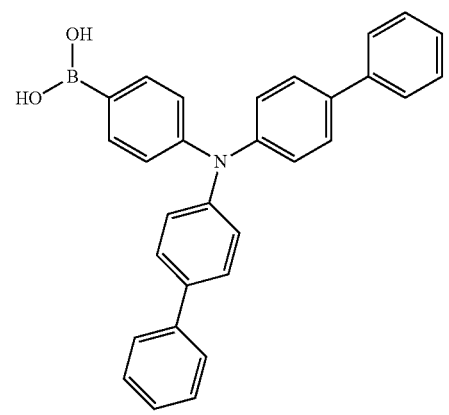
[943836-24-6]
8l 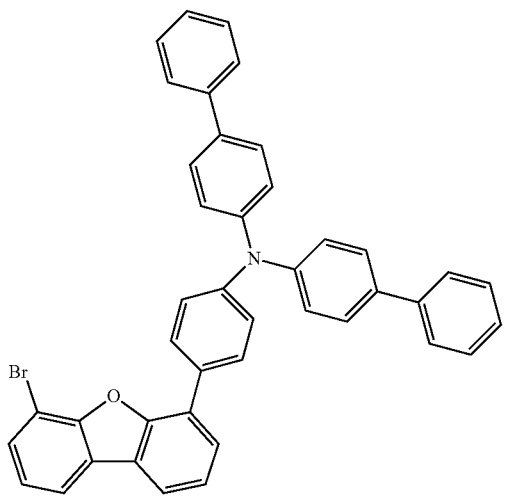 [SMILES: Brc1cccc2c1oc1c(-c3ccc(N(c4ccc(-c5ccccc5)cc4)c4ccc(-c5ccccc5)cc4)cc3)cccc12] 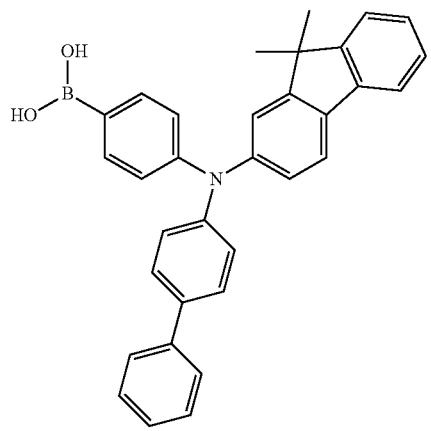
[1265177-27-2]

-continued
8m
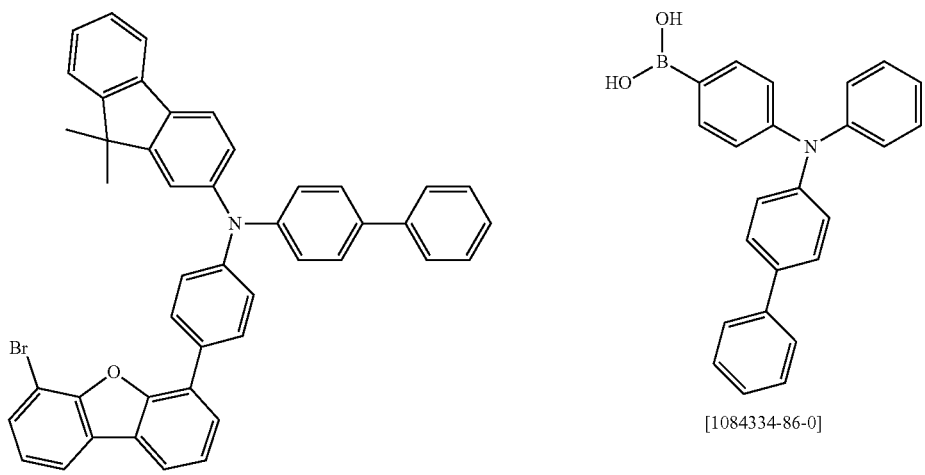
[1084334-86-0]
| Product |
|---------|
8a
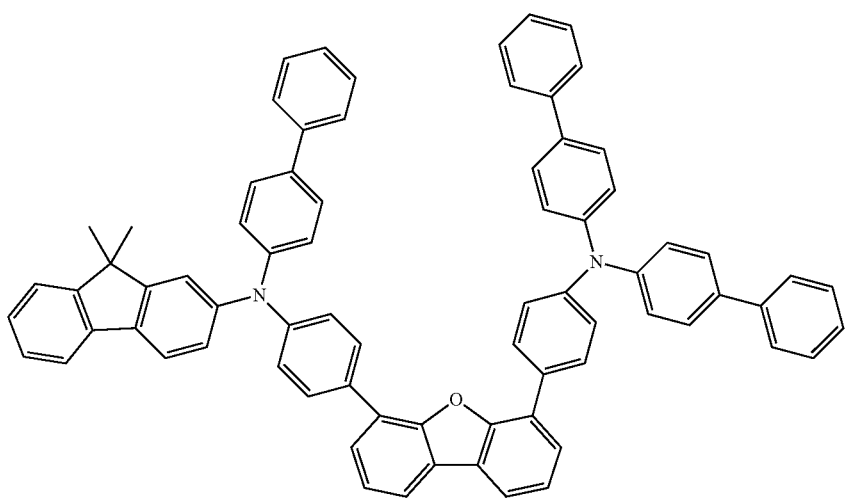 [SMILES: CC1(C)c2ccccc2-c2ccc(N(c3ccc(-c4ccccc4)cc3)c3ccc(-c4cccc5c4oc4c(-c6ccc(N(c7ccc(-c8ccccc8)cc7)c7ccc(-c8ccccc8)cc7)cc6)cccc45)cc3)cc21]
8b
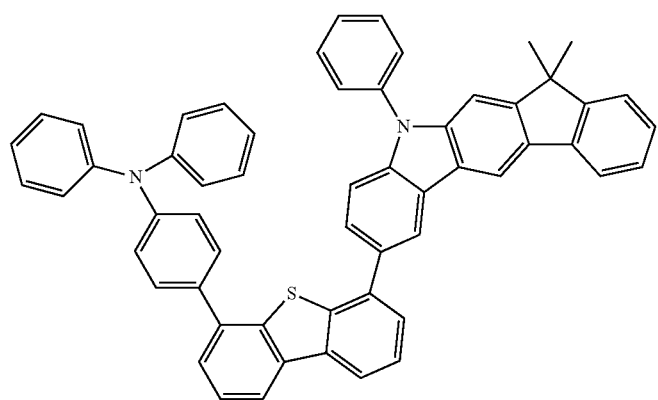 [SMILES: CC1(C)c2ccccc2-c2cc3c4cc(-c5cccc6c5sc5c(-c7ccc(N(c8ccccc8)c8ccccc8)cc7)cccc56)ccc4n(-c4ccccc4)c3cc21]

8c
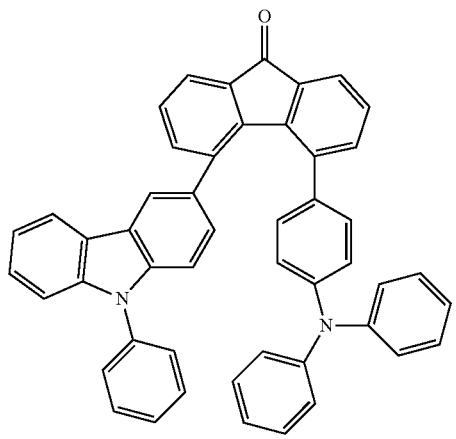 [SMILES: O=C1c2cccc(-c3ccc(N(c4ccccc4)c4ccccc4)cc3)c2-c2c1cccc2-c1ccc2c(c1)c1ccccc1n2-c1ccccc1]
8d
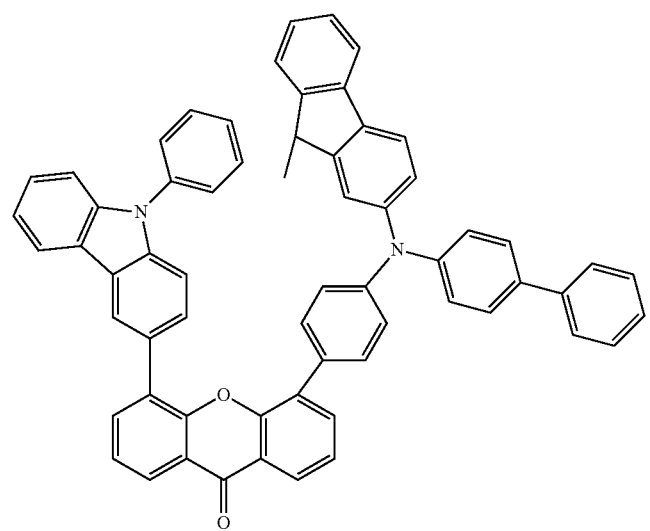 [SMILES: CC1c2ccccc2-c2ccc(N(c3ccc(-c4ccccc4)cc3)c3ccc(-c4cccc5c(=O)c6cccc(-c7ccc8c(c7)c7ccccc7n8-c7ccccc7)c6oc45)cc3)cc21]
8e
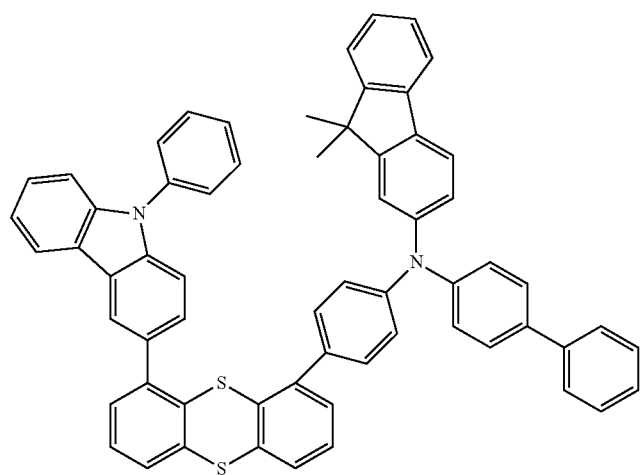 [SMILES: CC1(C)c2ccccc2-c2ccc(N(c3ccc(-c4ccccc4)cc3)c3ccc(-c4cccc5c4Sc4c(cccc4-c4ccc6c(c4)c4ccccc4n6-c4ccccc4)S5)cc3)cc21]

8f
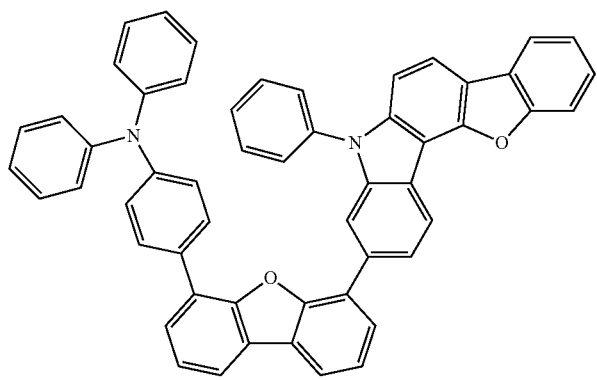 [SMILES: c1ccc(N(c2ccccc2)c2ccc(-c3cccc4c3oc3c(-c5ccc6c7c8oc9ccccc9c8ccc7n(-c7ccccc7)c6c5)cccc34)cc2)cc1]
8g
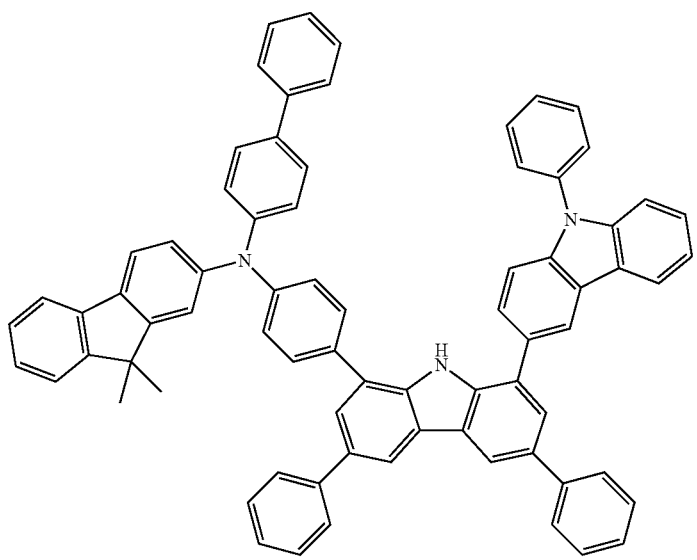 [SMILES: CC1(C)c2ccccc2-c2ccc(N(c3ccc(-c4ccccc4)cc3)c3ccc(-c4cc(-c5ccccc5)cc5c4[nH]c4c(-c6ccc7c(c6)c6ccccc6n7-c6ccccc6)cc(-c6ccccc6)cc45)cc3)cc21]
8h
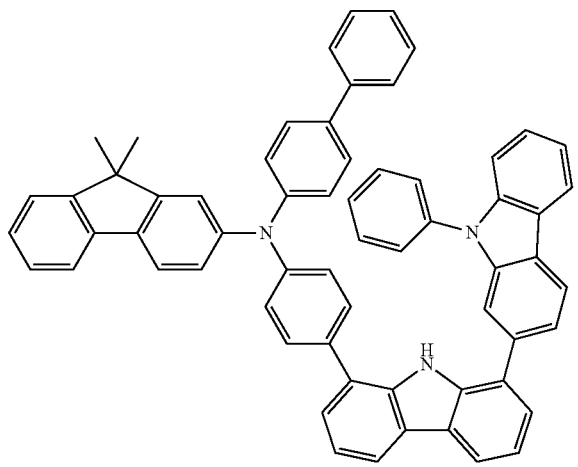 [SMILES: CC1(C)c2ccccc2-c2ccc(N(c3ccc(-c4ccccc4)cc3)c3ccc(-c4cccc5c4[nH]c4c(-c6ccc7c8ccccc8n(-c8ccccc8)c7c6)cccc45)cc3)cc21]

8i
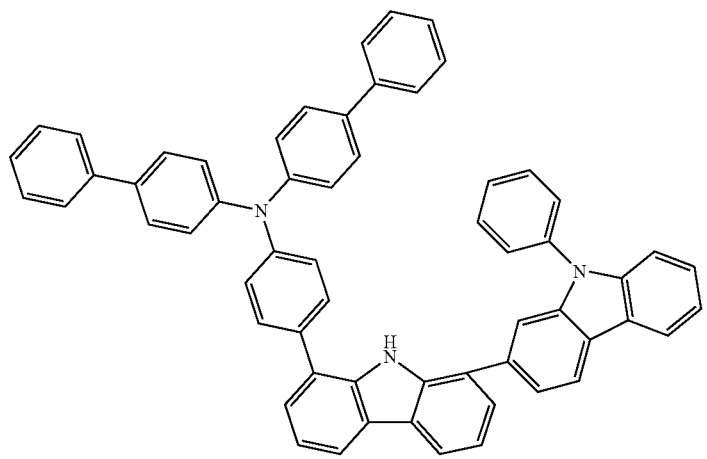 [SMILES: c1ccc(-c2ccc(N(c3ccc(-c4ccccc4)cc3)c3ccc(-c4cccc5c4[nH]c4c(-c6ccc7c8ccccc8n(-c8ccccc8)c7c6)cccc45)cc3)cc2)cc1]
8j
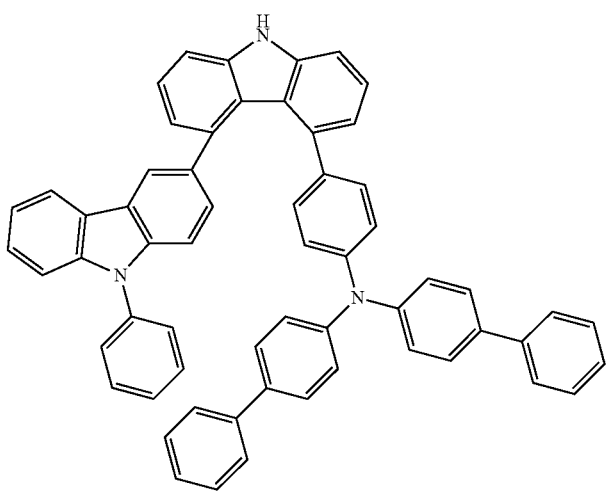 [SMILES: c1ccc(-c2ccc(N(c3ccc(-c4ccccc4)cc3)c3ccc(-c4cccc5[nH]c6cccc(-c7ccc8c(c7)c7ccccc7n8-c7ccccc7)c6c45)cc3)cc2)cc1]
8k
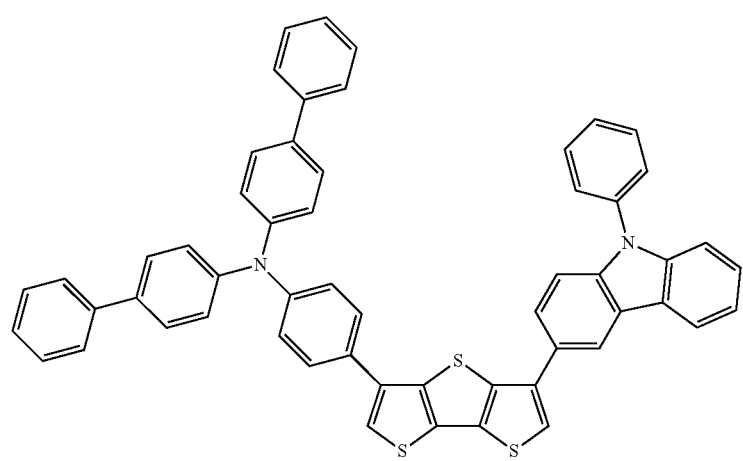 [SMILES: c1ccc(-c2ccc(N(c3ccc(-c4ccccc4)cc3)c3ccc(-c4csc5c4sc4c(-c6ccc7c(c6)c6ccccc6n7-c6ccccc6)csc45)cc3)cc2)cc1]

8l
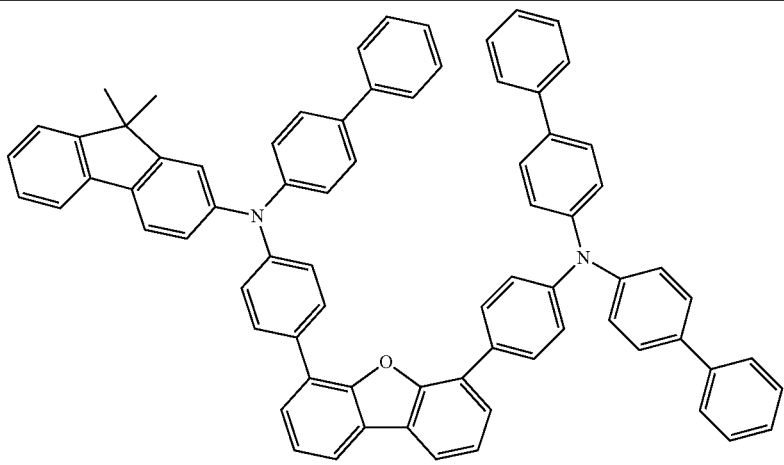
8m
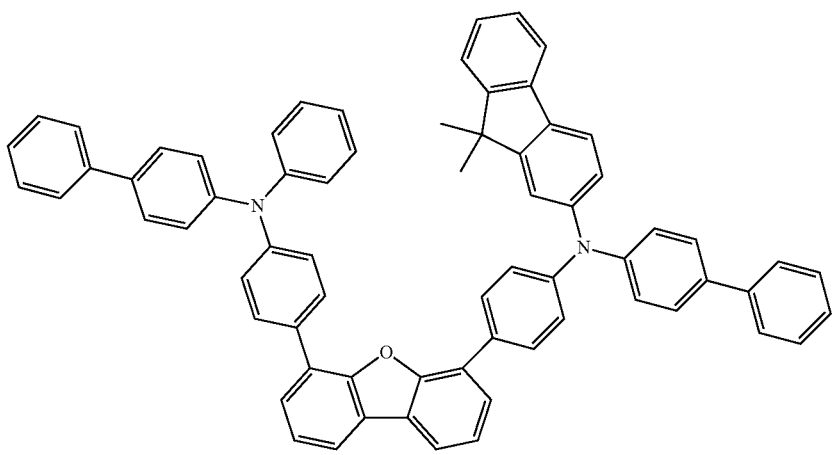 [SMILES: CC1(C)c2ccccc2-c2ccc(N(c3ccc(-c4ccccc4)cc3)c3ccc(-c4cccc5c4oc4c(-c6ccc(N(c7ccccc7)c7ccc(-c8ccccc8)cc7)cc6)cccc45)cc3)cc21]
|  | Yield |
|---|---|
| 8a | 68% |
| 8b | 73% |
| 8c | 86% |
| 8d | 65% |
| 8e | 63% |
| 8f | 79% |
| 8g | 62% |
| 8h | 64% |
-continued
|  | Yield |
|---|---|
| 8i | 65% |
| 8j | 64% |
| 8k | 66% |
| 8l | 62% |
| 8m | 65% |

Example 9: Bisbiphenyl-4-yl-[4-(9,9'-diphenyl-9H,9'H-[1,2']bicarbazolyl-8-yl)phenyl]amine

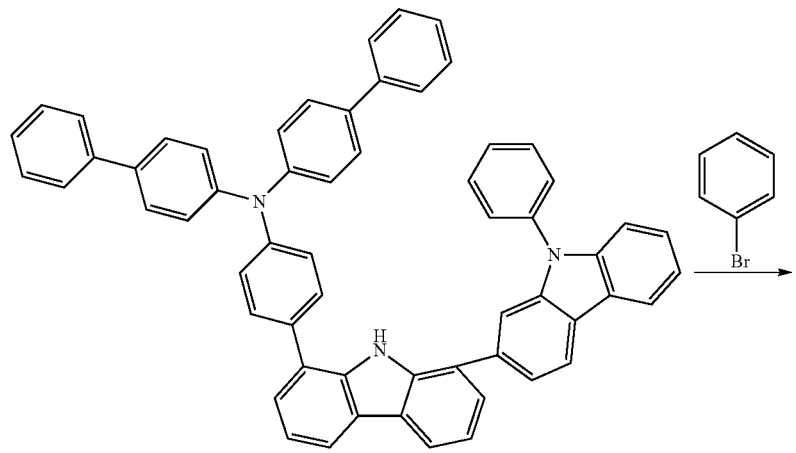

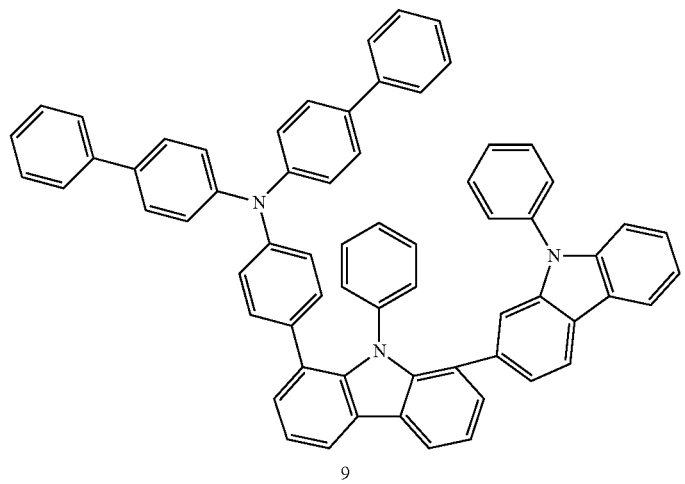

9

40 g (49.75 mmol) of bisbiphenyl-4-yl-[4-(9'-phenyl-9H,9'H-[1,2+]bicarbazolyl-8-yl)phenyl]amine and 16.7 g (74.62 mmol) of bromobenzene are dissolved in toluene and degassed by passing in a protective gas. 4.9 ml (4.9 mmol, 1 M solution in toluene) of tri-tert-butylphosphine, 633.7 mg (2.82 mmol) of Pd(OAc)$_2$ and 10.2 g (105.87 mmol) of t-BuONa are subsequently added. The solids are degassed in advance, the reaction mixture is degassed afterwards and subsequently stirred under reflux for 12 h. The warm reaction solution is filtered through aluminium oxide B (activity grade 1), washed with water, dried and evaporated. The yield is 29.9 g (33.98 mmol), corresponding to 68% of theory. The residue is recrystallised from toluene and finally sublimed in a high vacuum (p=5×10$^{-5}$ mbar). The purity is 99.9%.

The following compounds can be obtained analogously:
| | Starting material 1 | Starting material 2 |
|---|---|---|
| 9a | 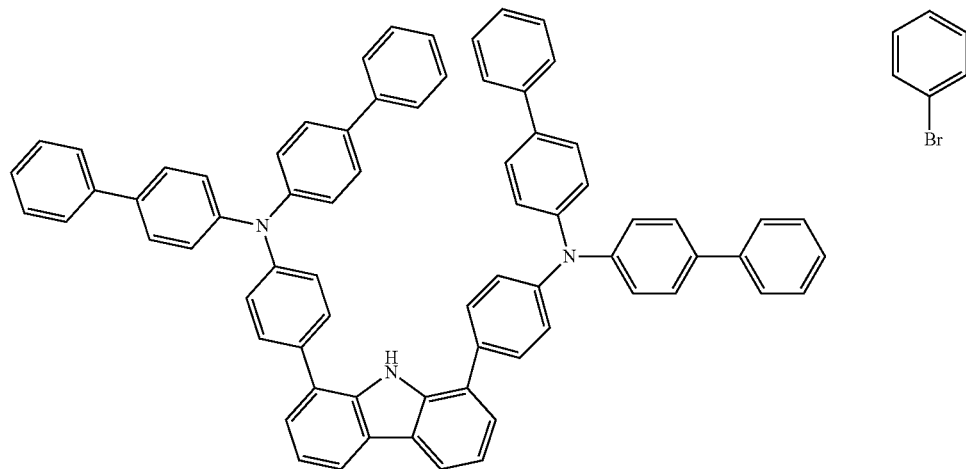 | 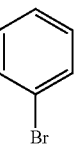 |
| 9b | 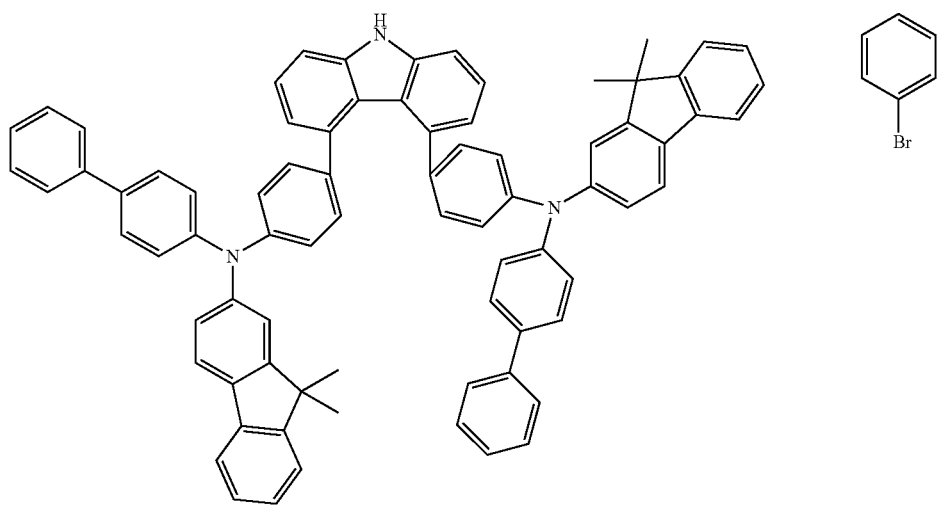 | 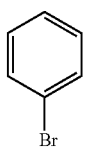 |
| 9c | 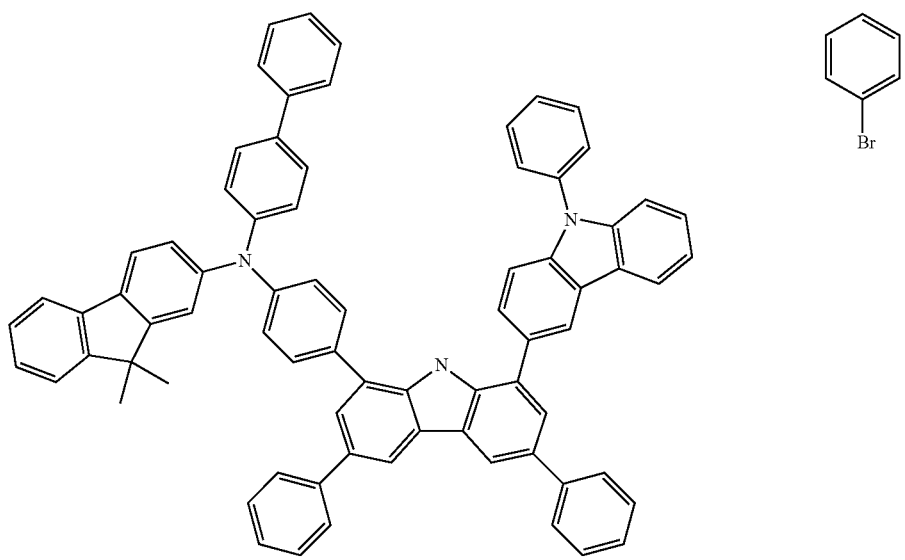 | 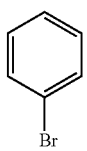 |

| | |
|---|---|
| 9d 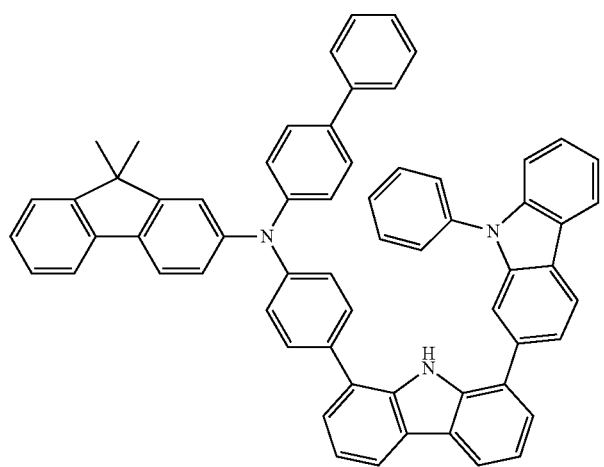 [SMILES: CC1(C)c2ccccc2-c2ccc(N(c3ccc(-c4ccccc4)cc3)c3ccc(-c4cccc5c4[nH]c4c(-c6ccc7c8ccccc8n(-c8ccccc8)c7c6)cccc45)cc3)cc21] | 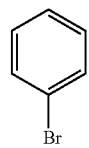 |
| 9e 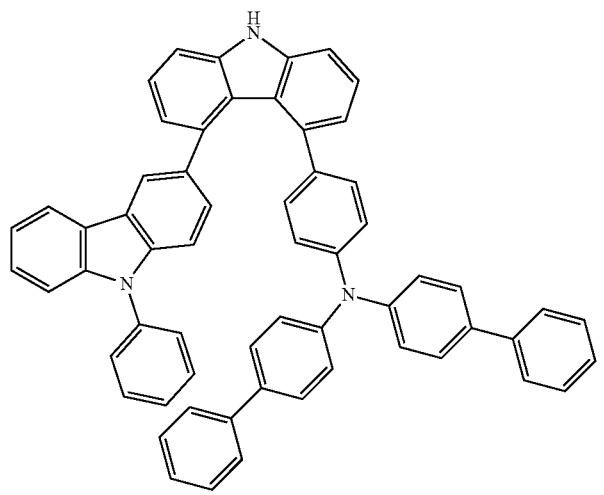 [SMILES: c1ccc(-c2ccc(N(c3ccc(-c4ccccc4)cc3)c3ccc(-c4cccc5[nH]c6cccc(-c7ccc8c(c7)c7ccccc7n8-c7ccccc7)c6c45)cc3)cc2)cc1] | 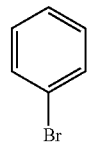 |
| Product |
|---|
| 9a 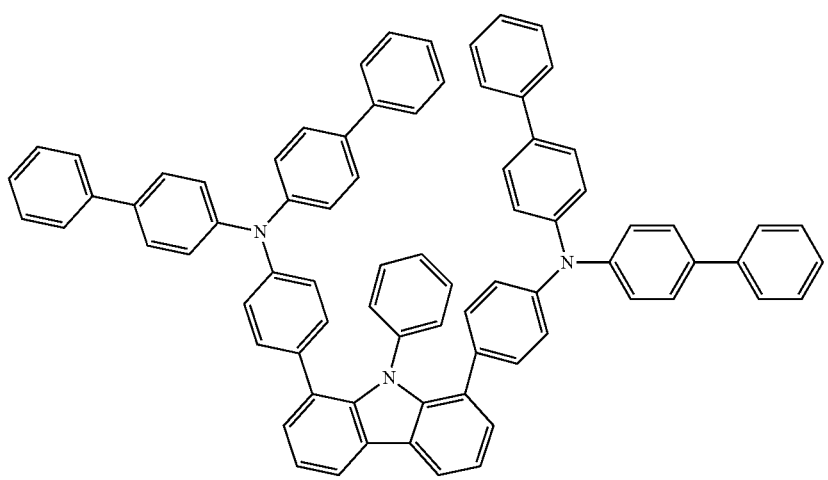 [SMILES: c1ccc(-c2ccc(N(c3ccc(-c4ccccc4)cc3)c3ccc(-c4cccc5c6cccc(-c7ccc(N(c8ccc(-c9ccccc9)cc8)c8ccc(-c9ccccc9)cc8)cc7)c6n(-c6ccccc6)c45)cc3)cc2)cc1] |

9b
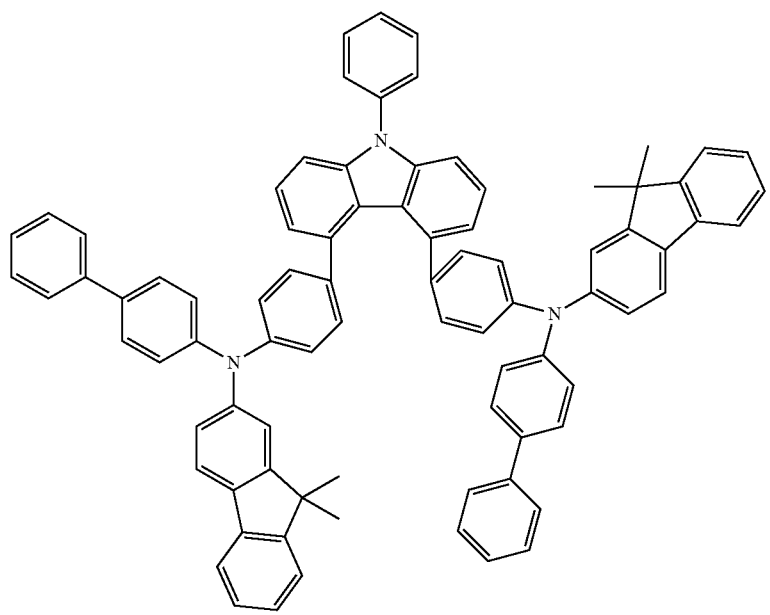 [SMILES: CC1(C)c2ccccc2-c2ccc(N(c3ccc(-c4ccccc4)cc3)c3ccc(-c4cccc5c4c4c(-c6ccc(N(c7ccc(-c8ccccc8)cc7)c7ccc8c(c7)C(C)(C)c7ccccc7-8)cc6)cccc4n5-c4ccccc4)cc3)cc21]
9c
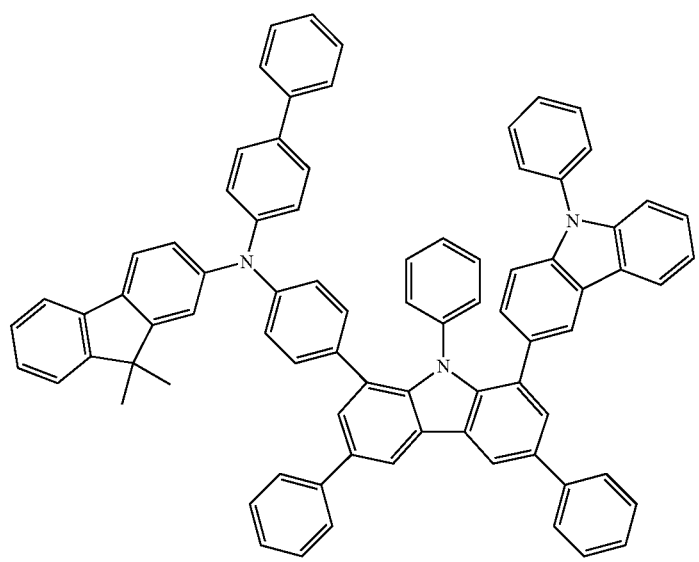 [SMILES: CC1(C)c2ccccc2-c2ccc(N(c3ccc(-c4ccccc4)cc3)c3ccc(-c4cc(-c5ccccc5)cc5c6cc(-c7ccccc7)cc(-c7ccc8c(c7)c7ccccc7n8-c7ccccc7)c6n(-c6ccccc6)c45)cc3)cc21]
9d
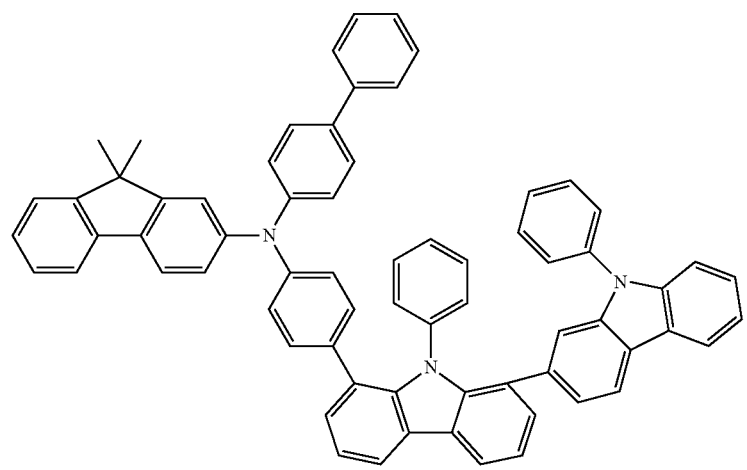 [SMILES: CC1(C)c2ccccc2-c2ccc(N(c3ccc(-c4ccccc4)cc3)c3ccc(-c4cccc5c6cccc(-c7ccc8c9ccccc9n(-c9ccccc9)c8c7)c6n(-c6ccccc6)c45)cc3)cc21]

9e

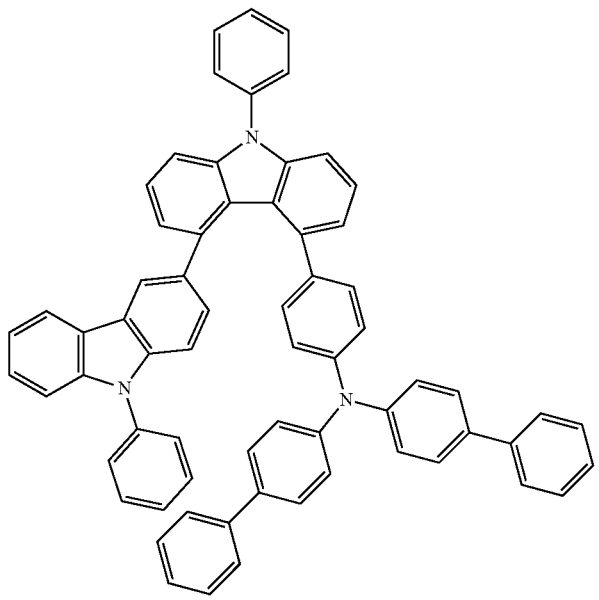 [SMILES: c1ccc(-c2ccc(N(c3ccc(-c4ccccc4)cc3)c3ccc(-c4cccc5c4c4c(-c6ccc7c(c6)c6ccccc6n7-c6ccccc6)cccc4n5-c4ccccc4)cc3)cc2)cc1]

| | Yield |
|---|---|
| 9a | 79% |
| 9b | 90% |
| 9c | 79% |
| 9d | 90% |
| 9e | 79% |

Synthesis of Precursors

Example Int-10:
Bisbiphenyl-4-yl-(6-bromodibenzofuran-4-yl)amine

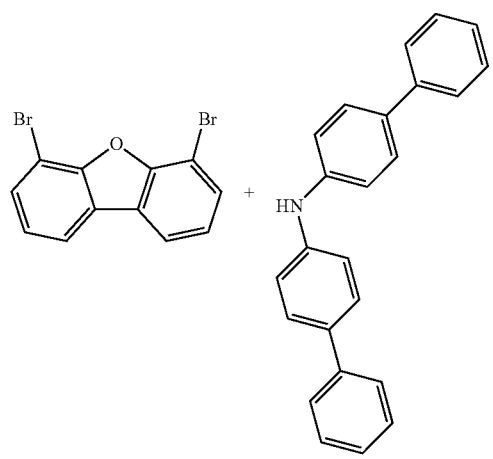

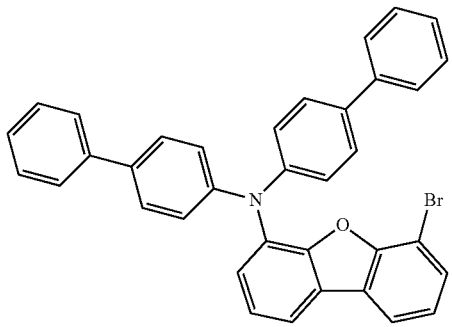

A mixture of 16.3 g (50 mmol) of 4,6-dibromodibenzofuran, 19.2 g (60 mmol) of bisbiphenyl-4-ylamine, 7.7 g (80 mmol) of sodium tert-butoxide, 1.4 g (5 mmol) of tricyclohexylamine, 561 mg (2.5 mmol) of palladium(II) acetate and 300 ml of mesitylene is heated under reflux for 24 h. After cooling, 200 ml of water are added, the mixture is stirred for a further 30 min., the org. phase is separated off, filtered through a short Celite bed, and the solvent is then removed in vacuo. The residue is recrystallised five times from DMF and finally subjected to fractional sublimation twice (p about $10^{-6}$ mbar). Yield: 22.9 g (40 mmol), 81%; purity: 99.9% according to HPLC.

The following compounds are obtained analogously:
| Ex. | Starting material | Product | | Yield |
|---|---|---|---|---|
| Int-10a | [201138-91-2] 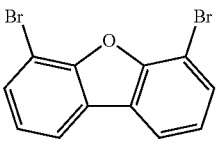 | 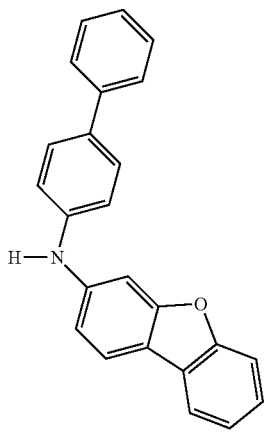 [1290039-85-8] | 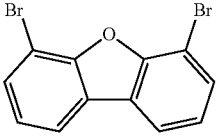 | 65% |
| Int-10b | [201138-91-2] | 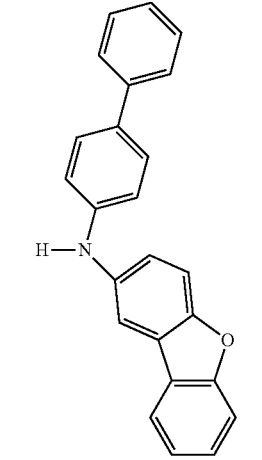 [1300028-94-7] | 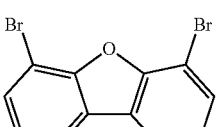 | 69% |
| Int-10c | [201138-91-2] | 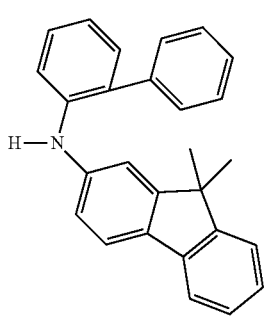 [1198395-24-2] | 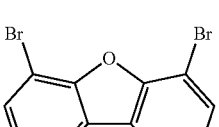 | 76% |
| Int-10d | [201138-91-2] | [86-74-8] | 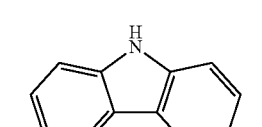 | 75% |

| Ex. | Starting material | Product | Yield |
|---|---|---|---|
| Int-10e | 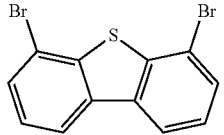 [669773-34-6] | 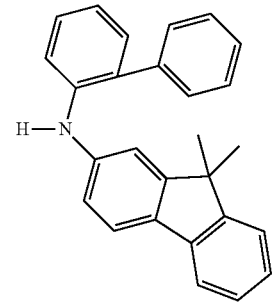 [1198395-24-2] | 71% |
Synthesis of Compounds According to the Invention:
The following compounds can be obtained analogously by second addition reaction with corresponding boro acids:
| Ex. | Starting material | Product |
|---|---|---|
| 10f | 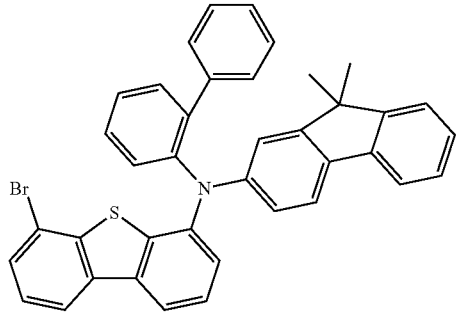 [SMILES: CC1(C)c2ccccc2-c2ccc(N(c3ccccc3-c3ccccc3)c3cccc4c3sc3c(Br)cccc34)cc21] | 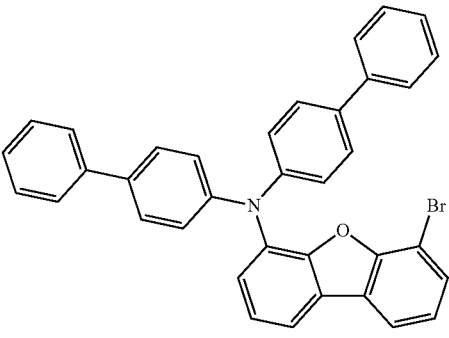 [SMILES: Brc1cccc2c1oc1c(N(c3ccc(-c4ccccc4)cc3)c3ccc(-c4ccccc4)cc3)cccc12] [1290039-85-8] |
| 10g | 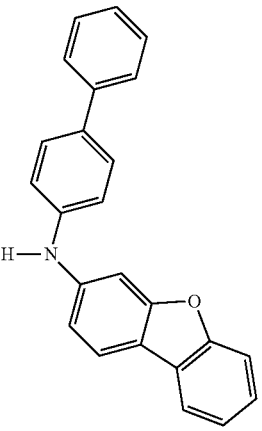 | 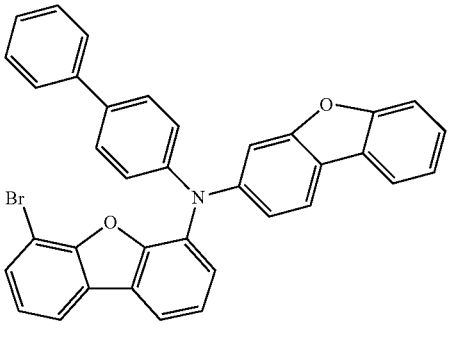 [SMILES: Brc1cccc2c1oc1c(N(c3ccc(-c4ccccc4)cc3)c3ccc4c(c3)oc3ccccc34)cccc12] [1300028-94-7] |

-continued
10h
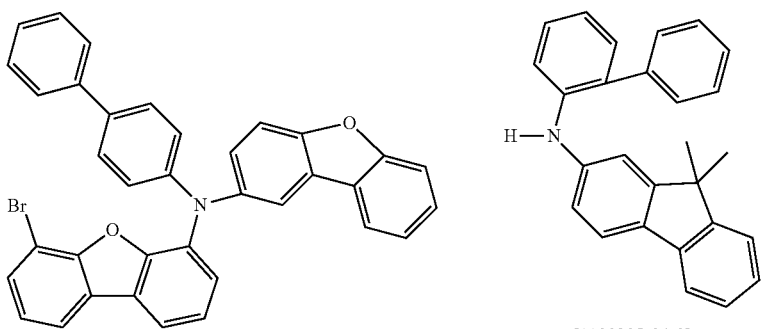
[1198395-24-2]
10i
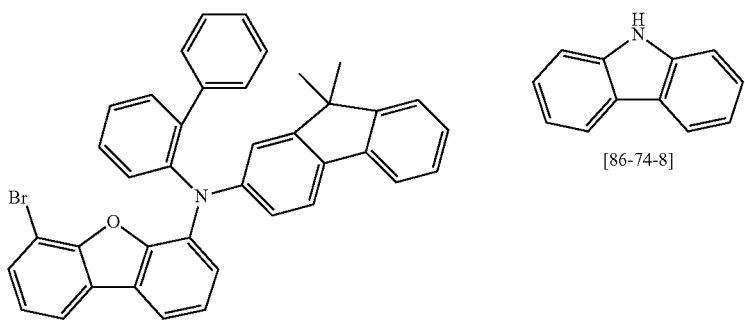
[86-74-8]
10j
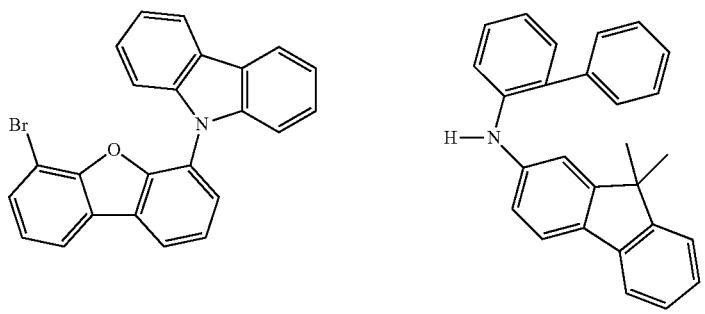
[1198395-24-2]
10f
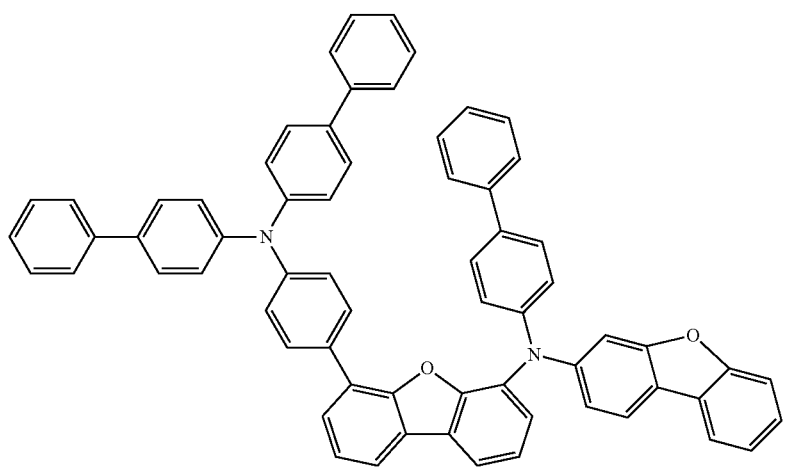 [SMILES: c1ccc(-c2ccc(N(c3ccc(-c4ccccc4)cc3)c3ccc(-c4cccc5c4oc4c(N(c6ccc(-c7ccccc7)cc6)c6ccc7c(c6)oc6ccccc67)cccc45)cc3)cc2)cc1]

-continued
10g
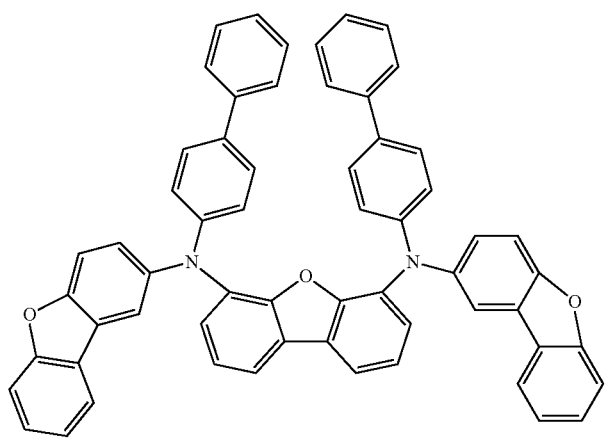 [SMILES: c1ccc(-c2ccc(N(c3ccc4oc5ccccc5c4c3)c3cccc4c3oc3c(N(c5ccc(-c6ccccc6)cc5)c5ccc6oc7ccccc7c6c5)cccc34)cc2)cc1]
10h
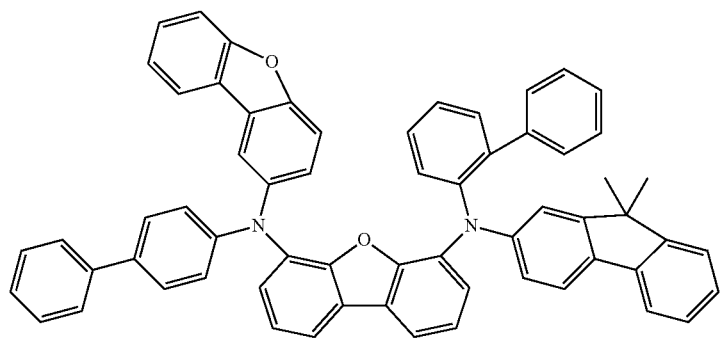 [SMILES: CC1(C)c2ccccc2-c2ccc(N(c3ccccc3-c3ccccc3)c3cccc4c3oc3c(N(c5ccc(-c6ccccc6)cc5)c5ccc6oc7ccccc7c6c5)cccc34)cc21]
10i
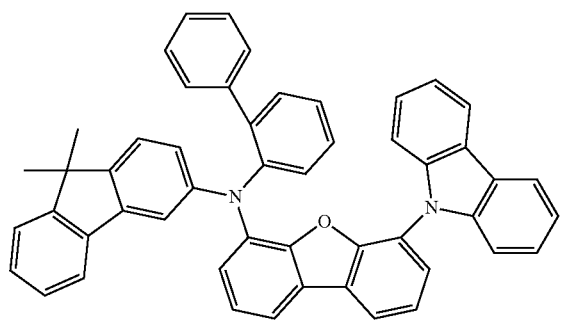 [SMILES: CC1(C)c2ccccc2-c2cc(N(c3ccccc3-c3ccccc3)c3cccc4c3oc3c(-n5c6ccccc6c6ccccc65)cccc34)ccc21]
10j
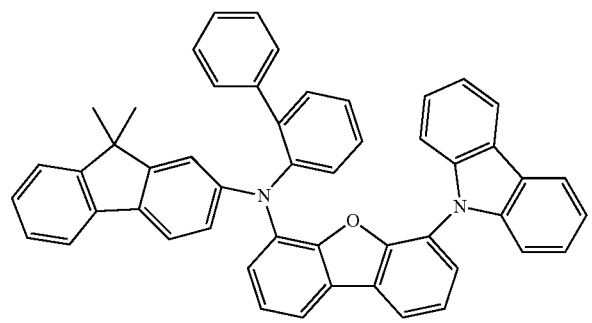 [SMILES: CC1(C)c2ccccc2-c2ccc(N(c3ccccc3-c3ccccc3)c3cccc4c3oc3c(-n5c6ccccc6c6ccccc65)cccc34)cc21]

| Ex. | Yield |
|---|---|
| 10f | 65% |
| 10g | 66% |
| 10h | 76% |
| 10i | 75% |
| 10j | 77% |

B) Device Examples: Production of the OLEDs

OLEDs according to the invention and OLEDs in accordance with the prior art are produced by a general process in accordance with WO 04/058911, which is adapted to the circumstances described here (layer-thickness variation, materials).

The data for various OLEDs are presented in the following Examples E1 to E5 according to the invention and in Reference Examples V1 to V3. The substrates used are glass plates coated with structured ITO (indium tin oxide) in a thickness of 50 nm. The OLEDs have in principle the following layer structure: substrate/p-doped hole-transport layer (HTL1)/hole-transport layer (HTL2)/p-doped hole-transport layer (HTL3)/hole-transport layer (HTL4)/emission layer (EML)/electron-transport layer (ETL)/electron-injection layer (EIL) and finally a cathode. The cathode is formed by an aluminium layer with a thickness of 100 nm.

The materials required for the production of the OLEDs are shown in Table 1, the various component structures are shown in Table 2.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as H1:SEB1 (95%:5%) here means that material H1 is present in the layer in a proportion by volume of 95% and SEB1 is present in the layer in a proportion of 5%. Analogously, the electron-transport layer or hole-injection layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The expression EQE @ 10 mA/cm$^2$ denotes the external quantum efficiency at a current density of 10 mA/cm$^2$. LT80 @ 50 mA/cm$^2$ (lifetime) is the time by which the luminance of the OLED has dropped to 80% of the initial intensity at an initial luminance at constant current of 50 mA/cm$^2$.

TABLE 1

Structures of the materials used

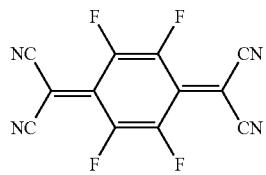

F4TCNQ

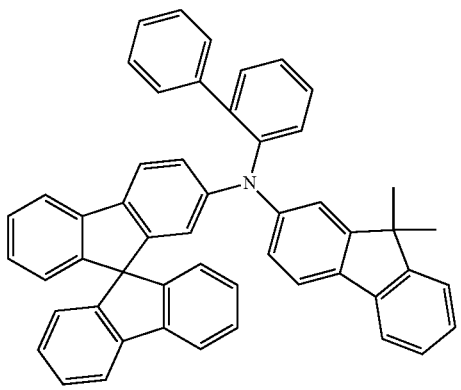 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

HIM1

TABLE 1-continued
Structures of the materials used
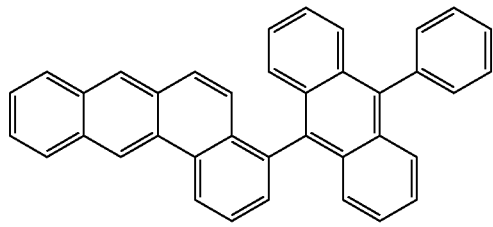 [SMILES: c1ccc(-c2c3ccccc3c(-c3cccc4c3ccc3cc5ccccc5cc34)c3ccccc23)cc1]
H1
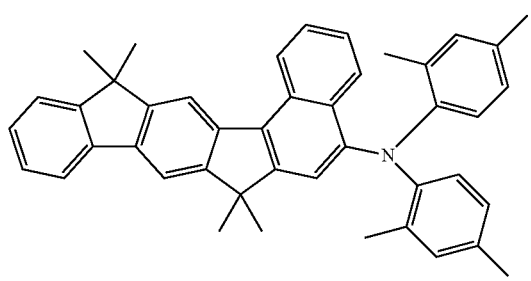 [SMILES: Cc1ccc(N(c2ccc(C)cc2C)c2cc3c(c4ccccc24)-c2cc4c(cc2C3(C)C)-c2ccccc2C4(C)C)c(C)c1]
SEB1
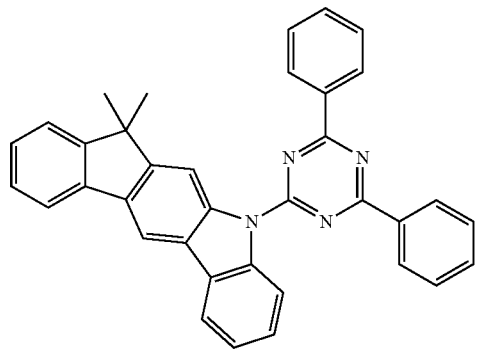 [SMILES: CC1(C)c2ccccc2-c2cc3c4ccccc4n(-c4nc(-c5ccccc5)nc(-c5ccccc5)n4)c3cc21]
H2
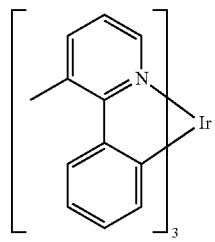
TEG TABLE 1-continued
Structures of the materials used
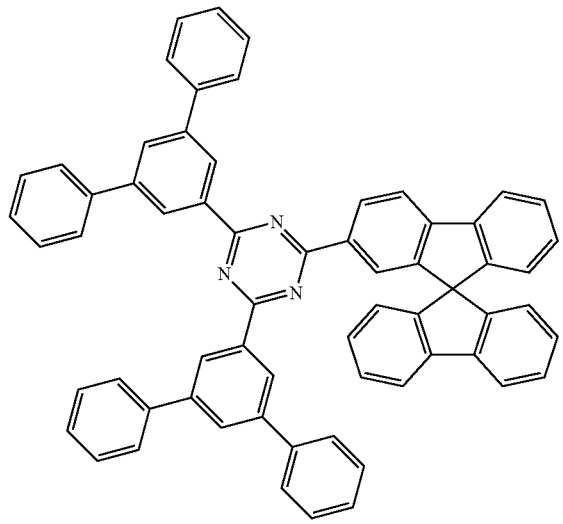 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM
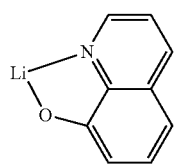
LiQ
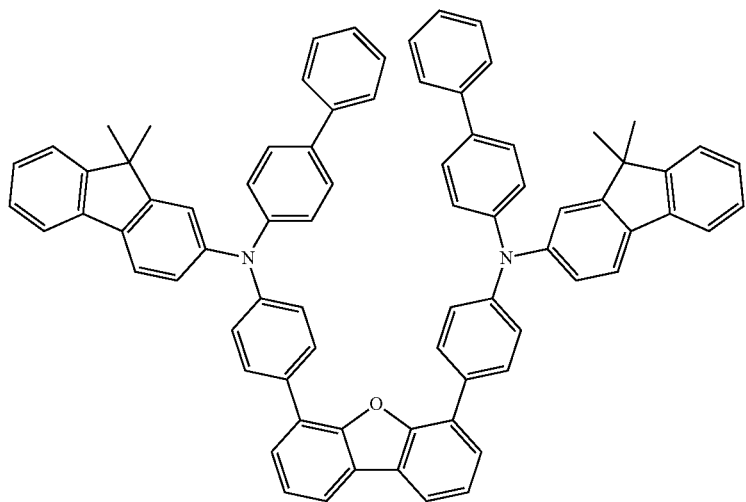 [SMILES: CC1(C)c2ccccc2-c2ccc(N(c3ccc(-c4ccccc4)cc3)c3ccc(-c4cccc5c4oc4c(-c6ccc(N(c7ccc(-c8ccccc8)cc7)c7ccc8c(c7)C(C)(C)c7ccccc7-8)cc6)cccc45)cc3)cc21]
HTM1

TABLE 1-continued
Structures of the materials used
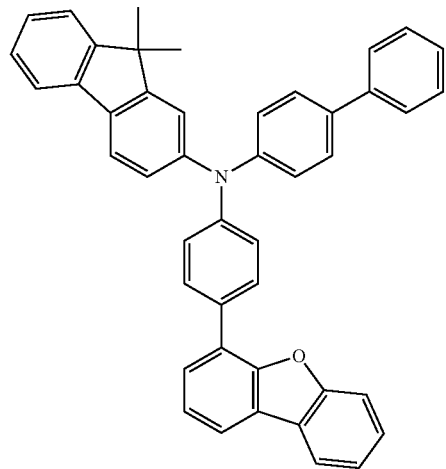 [SMILES: CC1(C)c2ccccc2-c2ccc(N(c3ccc(-c4ccccc4)cc3)c3ccc(-c4cccc5c4oc4ccccc45)cc3)cc21]
HTMV1
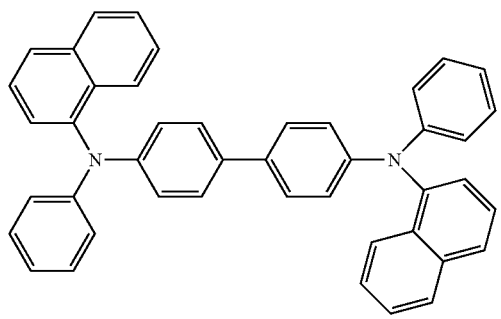 [SMILES: c1ccc(N(c2ccc(-c3ccc(N(c4ccccc4)c4cccc5ccccc45)cc3)cc2)c2cccc3ccccc23)cc1]
HTMV2
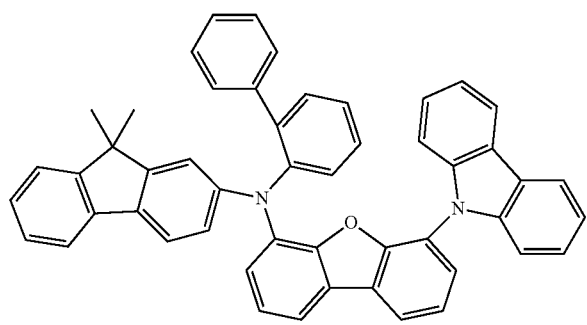 [SMILES: CC1(C)c2ccccc2-c2ccc(N(c3ccccc3-c3ccccc3)c3cccc4c3oc3c(-n5c6ccccc6c6ccccc65)cccc34)cc21]
HTM2

TABLE 1-continued

Structures of the materials used

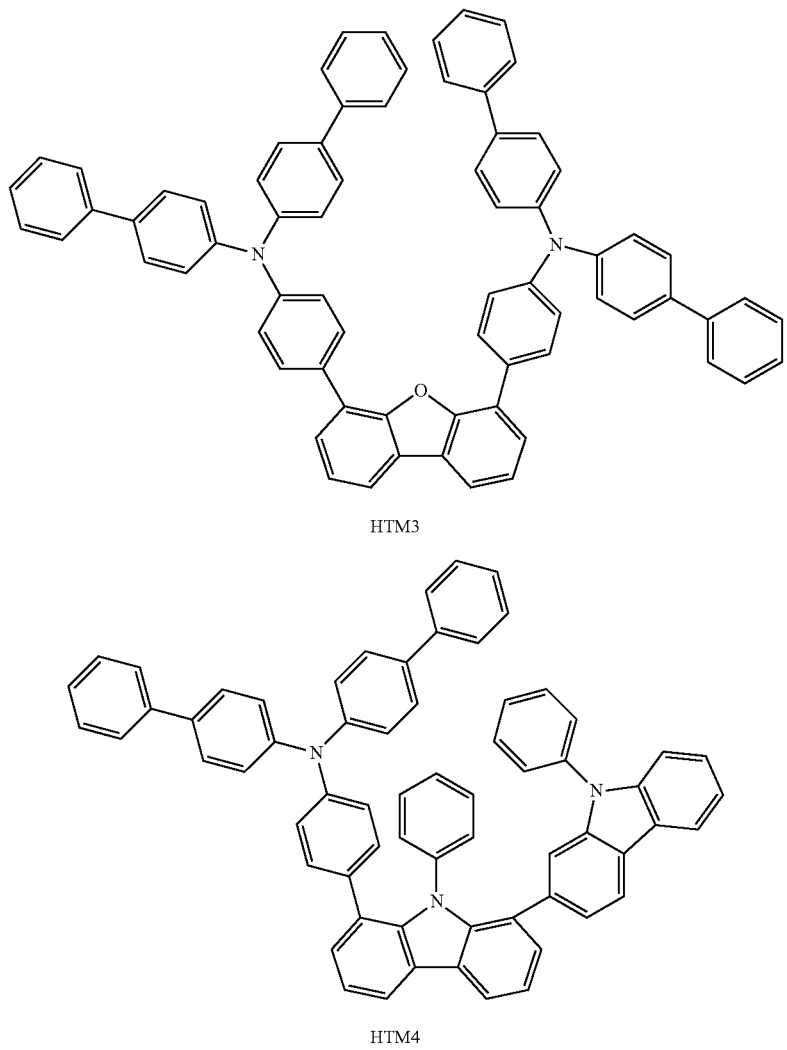

HTM3

HTM4

TABLE 2

Structure of the devices

| Ex. | HTL1 Thickness/ nm | HTL2 Thickness/ nm | HTL3 Thickness/ nm | HTL4 Thickness/ nm | EML Thickness/ nm | ETL Thickness/ nm | EIL Thickness/ nm |
|---|---|---|---|---|---|---|---|
| V1 | HIM1: F4TCNQ (3%) 20 nm | HIM1 155 nm | HTMV1: F4TCNQ (3%) 20 nm | HTMV1 20 nm | H1:SEB1 (5%) 20 nm | ETM (50%): LiQ (50%) 30 nm | LiQ 1 nm |
| E1 | HIM1: F4TCNQ (3%) 20 nm | HIM1 155 nm | HTM1: F4TCNQ (3%) 20 nm | HTM1 20 nm | H1:SEB1 (5%) 20 nm | ETM (50%): LiQ (50%) 30 nm | LiQ 1 nm |
| V2 | HIM1: F4TCNQ (3%) 20 nm | HIM1 160 nm | HTMV1: F4TCNQ (3%) 20 nm | HTMV1 70 nm | H2:TEG (10%) 30 nm | ETM (50%): LiQ (50%) 40 nm | LiQ 1 nm |
| E2 | HIM1: F4TCNQ (3%) 20 nm | HIM1 160 nm | HTM1: F4TCNQ (3%) 20 nm | HTM1 70 nm | H2:TEG (10%) 30 nm | ETM (50%): LiQ (50%) 40 nm | LiQ 1 nm |

TABLE 2-continued

Structure of the devices

| Ex. | HTL1 Thickness/nm | HTL2 Thickness/nm | HTL3 Thickness/nm | HTL4 Thickness/nm | EML Thickness/nm | ETL Thickness/nm | EIL Thickness/nm |
|---|---|---|---|---|---|---|---|
| V3 | HIM1:F4TCNQ (3%) 20 nm | HIM1 155 nm | HTMV2:F4TCNQ (3%) 20 nm | HTMV2 20 nm | H1:SEB1 (5%) 20 nm | ETM (50%):LiQ (50%) 30 nm | LiQ 1 nm |
| E3 | HIM1:F4TCNQ (3%) 20 nm | HIM1 155 nm | HTM2:F4TCNQ (3%) 20 nm | HTM2 20 nm | H1:SEB1 (5%) 20 nm | ETM (50%):LiQ (50%) 30 nm | LiQ 1 nm |
| E4 | HIM1:F4TCNQ (3%) 20 nm | HIM1 155 nm | HTM3:F4TCNQ (3%) 20 nm | HTM3 20 nm | H1:SEB1 (5%) 20 nm | ETM (50%):LiQ (50%) 30 nm | LiQ 1 nm |
| E5 | HIM1:F4TCNQ (3%) 20 nm | HIM1 155 nm | HTM4:F4TCNQ (3%) 20 nm | HTM4 20 nm | H1:SEB1 (5%) 20 nm | ETM (50%):LiQ (50%) 30 nm | LiQ 1 nm |

Results:

The examples show the use of compound HTM1 according to the invention as hole-transport material in a hole-transport layer.

A comparative device V1 is produced and compared with device E1 according to the invention. Device V1 has a compound in accordance with the prior art HTMV1 in the hole-transport layer HTL3, device E1 according to the invention has a compound HTM1 in accordance with the present invention as hole-transport material in the hole-transport layer HTL3. Both devices E1 and V1 have a fluorescent compound (SEB1) in the emitting layer.

Reference device V1 has an external quantum efficiency of 7.8% and a lifetime (LT80 @ 50 mA/cm$^2$) of 290 h at a current density of 10 mA/cm$^2$. By comparison, both the external quantum efficiency at a current density of 10 mA/cm$^2$ of 8.4% is higher and also the measured lifetime (LT80 @ 50 mA/cm$^2$) of 320 h is longer in the case of device E1 according to the invention.

A comparative device V2 is produced and compared with device E2 according to the invention. Device V2 has a compound in accordance with the prior art HTMV1 in the hole-transport layer HTL3, device E2 according to the invention has a compound HTM1 in accordance with the present invention as hole-transport material in the hole-transport layer HTL3. Both devices E1 and V1 have a phosphorescent compound (TEG) in the emitting layer.

Compared with a reference device V2, the corresponding device E2 according to the invention exhibits both a higher quantum efficiency (@ 2 mA/cm$^2$) of 20.4% compared with reference device V2 of 19.4% and also a longer lifetime (LT80 @ 20 mA/cm$^2$) of 180 h compared with reference device E2 of 120 h.

Compared with reference material HTMV2 (6.2%, 135 h)), the materials according to the invention HTM2 (7.4%, 270 h), HTM3 (8.2%, 300 h) and HTM4 (7.2%, 210 h) exhibit better external quantum efficiencies at 10 mA/cm$^2$ and a better lifetime (LT80 at 50 mA/cm$^2$) on use as hole-transport material in a blue-fluorescent OLED.

The examples show the surprising advantages on use of compounds HTM1 to HTM4 according to the invention containing two arylamino groups or one arylamino group and one carbazole group bonded "face to face" to a central linker group, compared with the use of a compound containing a single arylamino group HTMV1 or the use of the diamino compound HTMV2.

The examples show advantages on use of the materials as hole-transport material in combination with fluorescent and phosphorescent emitting layers. However, the invention is not restricted to this use. For example, the compounds can also be employed with comparably advantageous effect as matrix materials in the emitting layer.

C) Measurement of the Glass Transition Temperature $T_G$ measurements are carried out by standard methods (carried out on a TA-Instruments Q2000 series instrument for DSC measurement). The following results are obtained (Table 3).

TABLE 3

$T_G$ measurements

| Compound | Glass transition temperature $T_G$ |
|---|---|
| HTMV1 | 111° C. |
| HTM1 | 155° C. |
| HTM2 | 148° C. |
| HTM3 | 113° C. |
| HTM4 | 142° C. |

It was found that material HTM1 according to the invention has a high glass transition temperature of 155° C., which is very advantageous for use in OLEDs. Compounds HTM2 and HTM4 according to the invention also have high glass transition temperatures. By contrast, the glass transition temperature $T_G$ of comparative compound HTMV1 is significantly lower.

The invention claimed is:

1. An electronic device comprising anode, cathode and at least one organic layer, which comprises at least one compound of the formula (I) or (II)

formula (I)

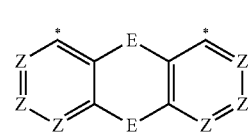

-continued formula (II)

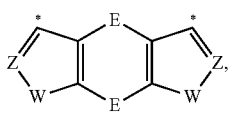

where a group selected from the groups of the formulae formula (A-1)

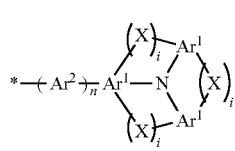

is bonded at the positions denoted by *, where:
E is selected on each occurrence, identically or differently, from a single bond, $C(R^1)_2$, $Si(R^1)_2$, C=O, O, S, S=O, $SO_2$ and $NR^1$;
Z is on each occurrence, identically or differently, $CR^1$ or N;
W is selected on each occurrence, identically or differently, from C=O, O, S, S=O, $SO_2$ and $NR^1$;
$Ar^1$ is selected on each occurrence, identically or differently, from aryl or heteroaryl groups having 6 to 13 aromatic ring atoms, which is optionally substituted by one or more radicals $R^1$;
$Ar^2$ is selected on each occurrence, identically or differently, from aryl or heteroaryl groups having 6 to 13 aromatic ring atoms, which is optionally substituted by one or more radicals $R^1$;
X is selected on each occurrence, identically or differently, from $C(R^1)_2$, $Si(R^1)_2$, C=O, O, S, S=O, $SO_2$ and $NR^1$;
Y is a single bond;
$R^1$ is on each occurrence, identically or differently, H, D, F, $C(=O)R^2$, CN, $Si(R^2)_3$, $N(R^2)_2$, $P(=O)(R^2)_2$, $S(=O)R^2$, $S(=O)_2R^2$, a straight-chain alkyl or alkoxy group having 1 to 20 C atoms or a branched or cyclic alkyl, or alkoxy group having 3 to 20 C atoms or an alkenyl or alkynyl group having 2 to 20 C atoms, where the above-mentioned groups may each be substituted by one or more radicals $R^2$ and where one or more $CH_2$ groups in the above-mentioned groups is optionally replaced by —$R^2C$=$CR^2$—, —C≡C—, $Si(R^2)_2$, C=O, C=S, C=$NR^2$, —C(=O)O—, —C(=O)$NR^2$—, $NR^2$, $P(=O)(R^2)$, —O—, —S—, SO or $SO_2$ and where one or more H atoms in the above-mentioned groups is optionally replaced by D, F or CN, or an aromatic or heteroaromatic ring system having 5 to 30 aromatic ring atoms, which is optionally substituted by one or more radicals $R^2$, or an aryloxy or heteroaryloxy group having 5 to 30 aromatic ring atoms, which is optionally substituted by one or more radicals $R^2$, where two or more radicals $R^1$ is optionally linked to one another and may form a ring;
$R^2$ is on each occurrence, identically or differently, H, D, F or an aliphatic, aromatic or heteroaromatic organic radical having 1 to 20 C atoms, in which, in addition, one or more H atoms is optionally replaced by D or F; two or more substituents $R^2$ here is optionally linked to one another and may form a ring;
n is on each occurrence, identically or differently, 0, 1, 2, 3 or 4;
i is on each occurrence, identically or differently, 0 or 1;
k is on each occurrence, identically or differently, 0 or 1, where at least one index k per group of the formula (C-1) must be equal to 1;
and where a group selected from groups of the formulae (A-1) and (A-2) must be bonded at at least one of the positions denoted by *,
and where furthermore no condensed aryl or heteroaryl group having 14 or more aromatic ring atoms is present in the compound.

2. The electronic device according to claim 1, wherein the group E is selected on each occurrence, identically or differently, from a single bond, $C(R^1)_2$, C=O, O, S and $NR^1$.

3. The electronic device according to claim 1, wherein the group $Ar^1$ is selected on each occurrence, identically or differently, from aryl or heteroaryl groups having 6 to 10 aromatic ring atoms, which is optionally substituted by one or more radicals $R^1$.

4. The electronic device according to claim 1, wherein the group $Ar^2$ is selected on each occurrence, identically or differently, from aryl or heteroaryl groups having 6 to 10 aromatic ring atoms, which is optionally substituted by one or more radicals $R^1$.

5. The electronic device according to claim 1, wherein $R^1$ is on each occurrence, identically or differently, H, D, F, CN, $Si(R^2)_3$, $N(R^2)_2$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^2$ and where one or more $CH_2$ groups in the above-mentioned groups is optionally replaced by —C≡C—, —$R^2C$=$CR^2$—, $Si(R^2)_2$, C=O, C=$NR^2$, —$NR^2$—, —O—, —S—, —C(=O)O— or —C(=O)$NR^2$—, or an aromatic or heteroaromatic ring system having 5 to 20 aromatic ring atoms, which is optionally substituted by one or more radicals $R^2$, where two or more radicals $R^1$ is optionally linked to one another and may form a ring.

6. The electronic device according to claim 1, wherein the index n is on each occurrence, identically or differently, 0 or 1.

7. The electronic device according to claim 1, wherein the index i is equal to 0.

8. The electronic device according to claim 1, wherein in compounds of the formulae (I) and (II), a group selected from groups of the formula (A-1) and (A-2) according to claim 1 is bonded at the positions denoted by *.

9. The electronic device according to claim 1, wherein the compounds of the formulae (I) and (II) contain no further arylamino groups in addition to the groups (A-1), (A-2), (C-1) and (C-2) according to claim 1.

10. The electronic device according to claim 1, wherein the compounds of the formulae (I) and (II) contain no further carbazole groups in addition to the groups (A-1), (A-2), (C-1) and (C-2) according to claim 1.

11. The electronic device according to claim 1, wherein the compounds of the formula (I) are compounds of the following formulae (I-1) to (I-4):

formula (I-1)

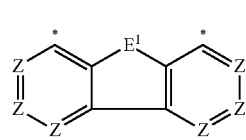

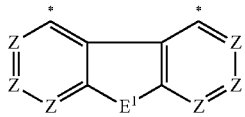
formula (I-2)

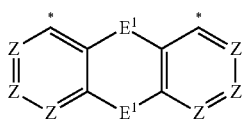
formula (I-3)

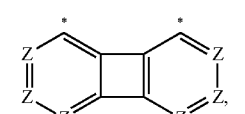
formula (I-4)

where $E^1$ is selected from $C(R^1)_2$, $Si(R^1)_2$, C=O, O, S, S=O, $SO_2$ and $NR^1$, where a group selected from the groups of the formulae (A-1), (A-2), (C-1) and (C-2) according to claim 1 is bonded at the positions denoted by *, and where a group selected from groups of the formulae (A-1) and (A-2) according to claim 1 is bonded at at least one of the positions denoted by *, and where all other groups are defined as in claim 1.

12. The electronic device according to claim 1, wherein the device is an organic integrated circuit (OIC), an organic field-effect transistor (OFET), an organic thin-film transistor (OTFT), an organic light-emitting transistor (OLET), an organic solar cell (OSC), an organic optical detector, an organic photoreceptor, an organic field-quench device (OFQD), an organic light-emitting electrochemical cell (OLEC), an organic laser diode (O-laser) or an organic electroluminescent device (OLED).

13. The electronic device according to claim 12, wherein the device is an organic electro-luminescent device comprising an organic layer which comprises the compound of the formula (I) or (II) is a layer having a hole-transporting function or an emitting layer.

14. A display and/or as light source in lighting applications and/or as light source in medical or cosmetic applications which comprises the electronic device according to claim 1.

15. An electronic device in a hole-transporting or in an emitting layer which comprises the compound of the formula (I) or (II)

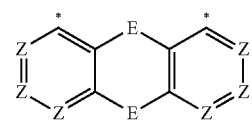
formula (I)

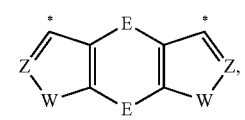
formula (II)

where a group selected from the groups of the formulae

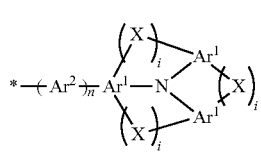
formula (A-1)

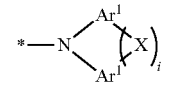
formula (A-2)

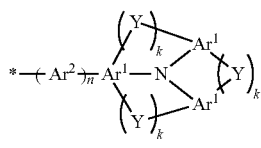
formula (C-1)

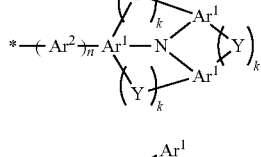
formula (C-2)

is bonded at the positions denoted by *, where:

E is selected on each occurrence, identically or differently, from a single bond, $C(R^1)_2$, $Si(R^1)_2$, C=O, O, S, S=O, $SO_2$ and $NR^1$;

Z is on each occurrence, identically or differently, $CR^1$ or N;

W is selected on each occurrence, identically or differently, from C=O, O, S, S=O, $SO_2$ and $NR^1$;

$Ar^1$ is selected on each occurrence, identically or differently, from aryl or heteroaryl groups having 6 to 13 aromatic ring atoms, which is optionally substituted by one or more radicals $R^1$;

$Ar^2$ is selected on each occurrence, identically or differently, from aryl or heteroaryl groups having 6 to 13 aromatic ring atoms, which is optionally substituted by one or more radicals $R^1$;

X is selected on each occurrence, identically or differently, from $C(R^1)_2$, $Si(R^1)_2$, C=O, O, S, S=O, $SO_2$ and $NR^1$;

Y is a single bond;

$R^1$ is on each occurrence, identically or differently, H, D, F, C(=O)$R^2$, CN, $Si(R^2)_3$, $N(R^2)_2$, P(=O)$(R^2)_2$, S(=O)$R^2$, S(=O)$_2R^2$, a straight-chain alkyl or alkoxy group having 1 to 20 C atoms or a branched or cyclic alkyl, or alkoxy group having 3 to 20 C atoms or an alkenyl or alkynyl group having 2 to 20 C atoms, where the above-mentioned groups may each be substituted by one or more radicals $R^2$ and where one or more $CH_2$ groups in the above-mentioned groups is optionally replaced by $-R^2C=CR^2-$, $-C\equiv C-$, $Si(R^2)_2$, C=O, C=S, C=$NR^2$, $-C(=O)O-$, $-C(=O)NR^2-$, $NR^2$, P(=O)$(R^2)$, $-O-$, $-S-$, SO or $SO_2$ and where one or more H atoms in the above-mentioned groups is optionally replaced by D, F or CN, or an aromatic or heteroaromatic ring system having 5 to 30 aromatic ring atoms, which is optionally substituted by one or more radicals $R^2$, or an aryloxy or heteroaryloxy group having 5 to 30 aromatic ring atoms, which is optionally substituted by one or more radicals $R^2$, where two or more radicals $R^1$ is optionally linked to one another and may form a ring;

$R^2$ is on each occurrence, identically or differently, H, D, F or an aliphatic, aromatic or heteroaromatic organic radical having 1 to 20 C atoms, in which, in addition, one or more H atoms is optionally replaced by D or F; two or more substituents $R^2$ here is optionally linked to one another and may form a ring;

n is on each occurrence, identically or differently, 0, 1, 2, 3 or 4;

i is on each occurrence, identically or differently, 0 or 1;

k is on each occurrence, identically or differently, 0 or 1, where at least one index k per group of the formula (C-1) must be equal to 1;

and where a group selected from groups of the formulae (A-1) and (A-2) must be bonded at at least one of the positions denoted by *, and where furthermore no condensed aryl or heteroaryl group having 14 or more aromatic ring atoms is present in the compound.

* * * * *